US010053725B2

(12) United States Patent
Liu et al.

(10) Patent No.: US 10,053,725 B2
(45) Date of Patent: *Aug. 21, 2018

(54) IN SITU INTERACTION DETERMINATION

(71) Applicant: President and Fellows of Harvard College, Cambridge, MA (US)

(72) Inventors: David R. Liu, Lexington, MA (US); Lynn Marie McGregor, Cambridge, MA (US); David Gorin, Cambridge, MA (US); Christoph Erich Dumelin, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 178 days.

This patent is subject to a terminal disclaimer.

(21) Appl. No.: 14/786,185

(22) PCT Filed: Apr. 23, 2014

(86) PCT No.: PCT/US2014/035177
§ 371 (c)(1),
(2) Date: Oct. 22, 2015

(87) PCT Pub. No.: WO2014/176355
PCT Pub. Date: Oct. 30, 2014

(65) Prior Publication Data
US 2016/0083786 A1 Mar. 24, 2016

Related U.S. Application Data

(60) Provisional application No. 61/815,029, filed on Apr. 23, 2013, provisional application No. 61/935,139, filed on Feb. 3, 2014.

(51) Int. Cl.
*C12P 19/34* (2006.01)
*C12Q 1/6841* (2018.01)
*C12Q 1/6804* (2018.01)
*C12N 15/10* (2006.01)

(52) U.S. Cl.
CPC ....... *C12Q 1/6841* (2013.01); *C12N 15/1065* (2013.01); *C12N 15/1068* (2013.01); *C12Q 1/6804* (2013.01)

(58) Field of Classification Search
CPC ............ C12N 15/1065; C12N 15/1068; C12Q 1/6841; C12Q 2563/179; C12Q 2525/125; C12Q 1/6804
USPC ...................................................... 435/91.2
See application file for complete search history.

(56) References Cited

U.S. PATENT DOCUMENTS

| | | | |
|---|---|---|---|
| 9,175,340 B2 | 11/2015 | Liu et al. | |
| 2009/0053710 A1 | 2/2009 | Fujihara et al. | |
| 2010/0267585 A1 | 10/2010 | Terbrueggen | |
| 2011/0039735 A1 | 2/2011 | Yamada et al. | |
| 2011/0183331 A1 | 7/2011 | Doi et al. | |
| 2016/0186238 A1 | 6/2016 | Liu et al. | |

FOREIGN PATENT DOCUMENTS

| WO | WO 2011/056185 A2 | 5/2011 |
|---|---|---|
| WO | WO 2014/176355 A1 | 10/2014 |

OTHER PUBLICATIONS

Invitation to Pay Additional Fees for PCT/US2010/002732, dated Mar. 1, 2011.
International Search Report and Written Opinion for PCT/US2010/002732, dated May 9, 2011.
International Preliminary Report on Patentability for PCT/US2010/002732, dated May 18, 2012.
International Search Report and Written Opinion for PCT/US2014/035177, dated Aug. 18, 2014.
International Preliminary Report on Patentability for PCT/US2014/035177, dated Nov. 5, 2015.
Agrawal et al., A pocket-sized convective PCR thermocycler. Angew Chem Int Ed Engl. 2007;46(23):4316-9.
Angenendt et al., Generation of high density protein microarrays by cell-free in situ expression of unpurified PCR products. Mol Cell Proteomics. Sep. 2006;5(9):1658-66. Epub Jul. 5, 2006.
Baker et al., An electronic, aptamer-based small-molecule sensor for the rapid, label-free detection of cocaine in adulterated samples and biological fluids. J Am Chem Soc. Mar. 15, 2006;128(10):3138-9.
Bartel et al., Isolation of new ribozymes from a large pool of random sequences. Science. Sep. 10, 1993;261(5127):1411-8.
Bowley et al., Libraries against libraries for combinatorial selection of replicating antigen-antibody pairs. Proc Natl Acad Sci U S A. Feb. 3, 2009;106(5):1380-5. Epub Jan. 12, 2009.
Breaker et al., A DNA enzyme that cleaves RNA. Chem Biol. Dec. 1994;1(4):223-9.
Chandra et al., DNA and RNA can be equally efficient catalysts for carbon-carbon bond formation. J Am Chem Soc. Mar. 12, 2008;130(10):2936-7. Epub Feb. 14, 2008.

(Continued)

*Primary Examiner* — Cynthia B Wilder
(74) *Attorney, Agent, or Firm* — Wolf, Greenfield & Sacks, P.C.

(57) ABSTRACT

Methods, reagents, compositions, and kits for in situ interaction determination (ISID) via interaction-dependent polymerase chain reaction (ID-PCR) are provided herein. ISID technology is useful for rapidly evaluating potential small molecule-target interactions from mixtures in a single solution. ISID is compatible with unpurified targets in biological samples and can be used to evaluate ligand-binding in DNA-encoded chemical libraries in cell lysates. ISID is also useful to screen ligand interactions of proteins or other molecules in their native state, including their native post-translational modifications and any interactions with accessory proteins and metabolites, in ways that better reflect their relevant biological environment. Because ISID is compatible with crude cell lysates, difficult-to-purify, poorly soluble, intrinsically unstable, and aggregation-prone targets may also be compatible with this method, without requiring truncation or other strategies used to promote heterologous expression.

42 Claims, 34 Drawing Sheets

(56) References Cited

OTHER PUBLICATIONS

Clark et al., Design, synthesis and selection of DNA-encoded small-molecule libraries. Nat Chem Biol. Sep. 2009;5(9):647-54.
Doyon et al., Highly sensitive in vitro selections for DNA-linked synthetic small molecules with protein binding affinity and specificity. J Am Chem Soc. Oct. 15, 2003;125(41):12372-3.
Dumelin et al., Selection of streptavidin binders from a DNA-encoded chemical library. Bioconjug Chem. Mar.-Apr. 2006;17(2):366-70.
Ellington et al., In vitro selection of RNA molecules that bind specific ligands. Nature. Aug. 30, 1990;346(6287):818-22.
Evans et al., Integrated, nontargeted ultrahigh performance liquid chromatography/electrospray ionization tandem mass spectrometry platform for the identification and relative quantification of the small-molecule complement of biological systems. Anal Chem. Aug. 15, 2009;81(16):6656-67.
Fredriksson et al., Protein detection using proximity-dependent DNA ligation assays. Nat Biotechnol. May 2002;20(5):473-7.
Gartner et al., The generality of DNA-templated synthesis as a basis for evolving non-natural small molecules. J Am Chem Soc. Jul. 18, 2001;123(28):6961-3.
Gartner et al., DNA-templated organic synthesis and selection of a library of macrocycles. Science. Sep. 10, 2004;305(5690):1601-5. Epub Aug. 19, 2004.
Gartner et al., Expanding the reaction scope of DNA-templated synthesis. Angew Chem Int Ed Engl. May 17, 2002;41(10):1796-800.
Gevaert et al., Exploring proteomes and analyzing protein processing by mass spectrometric identification of sorted N-terminal peptides. Nat Biotechnol. May 2003;21(5):566-9. Epub Mar. 31, 2003.
Gopinath, Methods developed for SELEX. Anal Bioanal Chem. Jan. 2007; 387(1):171-82. Epub Oct. 28, 2006. Review.
Gorin et al., Reactivity-dependent PCR: direct, solution-phase in vitro selection for bond formation. J Am Chem Soc. Jul. 8, 2009;131(26):9189-91.
Gorin et al., Reactivity-dependent PCR: direct, solution-phase in vitro selection for bond formation. J Am Chem Soc. Jul. 8, 2009;131(26):9189-91. Supporting Information: S1-S13.
Gorska et al., DNA-templated homo- and heterodimerization of peptide nucleic acid encoded oligosaccharides that mimick the carbohydrate epitope of HIV. Angew Chem Int Ed Engl. 2009;48(41):7695-700.
Green, Avidin and streptavidin. Methods Enzymol. 1990;184:51-67.
Gustafsdottir et al., Use of proximity ligation to screen for inhibitors of interactions between vascular endothelial growth factor A and its receptors. Clin Chem. Jul. 2008;54(7):1218-25.
Halpin et al., DNA display II. Genetic manipulation of combinatorial chemistry libraries for small-molecule evolution. Biol. 2004; 2:1022-30.
Hammond et al., Profiling cellular protein complexes by proximity ligation with dual tag microarray readout. PLoS One. 2012;7(7):e40405.
Hansen et al., A yoctoliter-scale DNA reactor for small-molecule evolution. J Am Chem Soc. Jan. 28, 2009;131(3):1322-7.
Haruki et al., Exploiting ligand-protein conjugates to monitor ligand-receptor interactions. PLoS One. 2012;7(5):e37598.
Heck, Palladium-catalyzed vinylation of organic halides. Org. React. 1928;27:345-90.
Hill et al., Nonenzymatic detection of bacterial genomic DNA using the bio bar code assay. Anal Chem. Dec. 1, 2007;79(23):9218-23. Epub Oct. 10, 2007.
Hill et al., The bio-barcode assay for the detection of protein and nucleic acid targets using DTT-induced ligand exchange. Nat Protoc.2006;1(1):324-36.
Himo et al., Copper(I)-catalyzed synthesis of azoles. DFT study predicts unprecedented reactivity and intermediates. J Am Chem Soc. Jan. 12, 2005;127(1):210-6.
Hinner et al., How to obtain labeled proteins and what to do with them. Curr Opin Biotechnol. Dec. 2010;21(6):766-76.
Höbartner et al., Site-selective depurination by a periodate-dependent deoxyribozyme. Chem Commun (Camb). Jun. 14, 2007;(22):2255-7.Epub May 10, 2007.
Hofstadler et al., Analysis of noncovalent complexes of DNA and RNA by mass spectrometry. Chem Rev. Feb. 2001;101(2):377-90. Review.
Inglese et al., High-throughput screening assays for the identification of chemical probes. Nat Chem Biol. Aug. 2007;3(8):466-79.
Jain et al., Identification of two hydrophobic patches in the active-site cavity of human carbonic anhydrase II by solution-phase and solid-state studies and their use in the development of tight-binding inhibitors. J Med Chem. Jun. 24, 1994;37(13):2100-5.
Jeffreys et al., Repeat unit sequence variation in minisatellites: a novel source of DNA polymorphism for studying variation and mutation by single molecule analysis. Cell. Feb. 9, 1990;60(3):473-85.
Johnston et al., RNA-catalyzed RNA polymerization: accurate and general RNA-templated primer extension. Science. May 18, 2001;292(5520):1319-25.
Joshi et al., A simple and sensitive color test for the detection of human chorionic gonadotropin. Obstet Gynecol. Feb. 1981;57(2):252-4.
Joyce, Directed evolution of nucleic acid enzymes. Annu Rev Biochem. 2004;73:791-836. Review.
Kanan et al., Reaction discovery enabled by DNA-templated synthesis and in vitro selection. Nature. Sep. 30, 2004;431(7008):545-9.
Kleiner et al., In vitro selection of a DNA-templated small-molecule library reveals a class of macrocyclic kinase inhibitors. J Am Chem Soc. Aug. 25, 2010;132(33):11779-91.
Kubista et al., The real-time polymerase chain reaction. Mol Aspects Med. Apr.-Jun. 2006;27(2-3):95-125. Epub Feb. 3, 2006. Review.
Kunishima et al., Synthesis and characterization of 4-(4,6-Dimethoxy-1,3,5-triazin-2-yl)-4methylmorpholinium chloride. Tetrahedron Lett. 1999;40:5327-30.
Li et al., DNA-templated organic synthesis: nature's strategy for controlling chemical reactivity applied to synthetic molecules. Angew Chem Int Ed Engl. Sep. 20, 2004;43(37):4848-70. Review.
Li et al., Translation of DNA into synthetic N-acyloxazolidines. J Am Chem Soc. Apr. 28, 2004;126(16):5090-2.
Lundberg et al., Homogeneous antibody-based proximity extension assays provide sensitive and specific detection of low-abundant proteins in human blood. Nucleic Acids Res. Aug. 2011;39(15):e102.
Mahrus et al., Global sequencing of proteolytic cleavage sites in apoptosis by specific labeling of protein N termini. Cell. Sep. 5, 2008;134(5):866-76. Epub Aug. 21, 2008.
Makrigiorgos, PCR-Based detection of minority point mutations. Human Mut. 2004;23(5):406.
Mannocci et al., High-throughput sequencing allows the identification of binding molecules isolated from DNA-encoded chemical libraries. Proc Natl Acad Sci U S A. Nov. 18, 2008;105(46):17670-5. Epub Nov. 10, 2008.
McDonald et al., Positional proteomics: selective recovery and analysis of N-terminal proteolytic peptides. Nat Methods. Dec. 2005;2(12):955-7. Epub Nov. 18, 2005.
McGregor et al., Identification of ligand-target pairs from combined libraries of small molecules and unpurified protein targets in cell lysates. J Am Chem Soc. Feb. 26, 2014;136(8):3264-70. With supporting information.
McGregor et al., Interaction-dependent PCR: identification of ligand-target pairs from libraries of ligands and libraries of targets in a single solution-phase experiment. J Am Chem Soc. Nov. 10, 2010;132(44):15522-4.
Melkko et al., Encoded self-assembling chemical libraries. Nat Biotechnol. May 2004;22(5):568-74. Epub Apr. 18, 2004.
Melkko et al., Isolation of high-affinity trypsin inhibitors from a DNA-encoded chemical library. Angew Chem Int Ed Engl. 2007;46(25):4671-4.
Mincione et al., Carbonic anhydrase inhibitors: 4-sulfamoyl benzenecarboxamides and 4-chloro-3-sulfamoyl-

(56) References Cited

OTHER PUBLICATIONS benzenecarboxamides with strong topical antiglaucoma properties. Bioorg Med Chem Lett. Jul. 9, 2001;11(13):1787-91.

Niemeyer, Semisynthetic DNA-protein conjugates for biosensing and nanofabrication. Angew Chem Int Ed Engl. Feb. 8, 2010;49(7):1200-16.

Ogawa et al., Aptazyme-based riboswitches as label-free and detector-free sensors for cofactors. Bioorg Med Chem Lett. Jun. 1, 2007;17(11):3156-60. Epub Mar. 15, 2007.

Otto et al., Cysteine Proteases and Their Inhibitors. Chem Rev. Feb. 5, 1997;97(1):133-171.

Pocker et al., The catalytic versatility of erythrocyte carbonic anhydrase. 3. Kinetic studies of the enzyme-catalyzed hydrolysis of p-nitrophenyl acetate. Biochemistry Mar. 1967;6(3):668-78.

Pradeepkumar et al., DNA-catalyzed formation of nucleopeptide linkages. Angew Chem Int Ed Engl. 2008;47(9):1753-7.

Robertson et al., Selection in vitro of an RNA enzyme that specifically cleaves single-stranded DNA. Nature. Mar. 29, 1990;344(6265):467-8.

Rose et al., Sensitivity gains in chemosensing by lasing action in organic polymers. Nature. Apr. 14, 2005;434(7035):876-9.

Rozenman et al., Development and initial application of a hybridization-independent, DNA-encoded reaction discovery system compatible with organic solvents. J Am Chem Soc. Dec. 5, 2007;129(48):14933-8. Epub Nov. 10, 2007.

Rozenman et al., DNA-templated synthesis in organic solvents. Chembiochem. Feb. 2006;7(2):253-6.

Rozenman et al., Solving chemical problems through the application of evolutionary principles. Curr Opin Chem Biol. Jun. 2007;11(3):259-68. Epub Jun. 4, 2007. Review.

Schwake et al., A carboxy-terminal domain determines the subunit specificity of KCNQ K+ channel assembly. EMBO Rep. Jan. 2003;4(1):76-81.

Seelig et al., A small catalytic RNA motif with Diels-Alderase activity.Chem Biol. Mar. 1999;6(3):167-76.

Shamah et al., Complex target SELEX. Acc Chem Res. Jan. 2008;41(1):130-8. Review.

Sharon et al., Impedimetric or ion-sensitive field-effect transistor (ISFET) aptasensors nanostructures. Electroanal. 2009;21:1291-6.

Sheppard et al., A DNA enzyme with N-glycosylase activity. Proc Natl Acad Sci U S A. Jul. 5, 2000;97(14):7802-7.

Silverman, Catalytic DNA (deoxyribozymes) for synthetic applications-current abilities and future prospects. Chem Commun (Camb). Aug. 14, 2008;(30):3467-85. Epub Jul. 1, 2008. Review.

Söderberg et al., Direct observation of individual endogenous protein complexes in situ by proximity ligation. Nat Methods. Dec. 2006;3(12):995-1000.

Sprinz et al., Self-assembly of bivalent protein-binding agents based on oligonucleotide-linked organic fragments. Bioorg Med Chem Lett. Sep. 1, 2005;15(17):3908-11.

Suebert et al., Isolation and quantification of soluble Alzheimer's beta-peptide from biological fluids. Naure. 1992;359:325-327.

Swensen et al., Continuous, real-time monitoring of cocaine in undiluted blood serum via a microfluidic, electrochemical aptamer-based sensor. J Am Chem Soc. Apr. 1, 2009;131(12):4262-6.

Tarasow et al., RNA-catalysed carbon-carbon bond formation. Nature. Sep. 4, 1997;389(6646):54-7.

Torreggiani et al., The binding of biotin analogues by streptavidin: a Raman spectroscopic study. Biospectroscopy. 1998;4(3):197-208.

Troutt et al., Ligation-anchored PCR: a simple amplification technique with single-sided specificity. Proc Natl Acad Sci U S A. Oct. 15, 1992;89(20):9823-5.

Tse et al., Translation of DNA into a library of 13,000 synthetic small-molecule macrocycles suitable for in vitro selection. J Am Chem Soc. Nov. 19, 2008;130(46):15611-26. Epub Oct. 29, 2008.

Tuerk et al., Systematic evolution of ligands by exponential enrichment: RNA ligands to bacteriophage T4 DNA polymerase. Science. Aug. 3, 1990;249(4968):505-10.

Vignali, Multiplexed particle-based flow cytometric assays. J Immunol Methods. Sep. 21, 2000;243(1-2):243-55. Review.

Vijayendran et al., A quantitative assessment of heterogeneity for surface-immobilized proteins. Anal Chem. Feb. 1, 2001;73(3):471-80.

West et al., Thermodynamic analysis of protein stability and ligand binding using a chemical modification- and mass spectrometry-based strategy. Anal Chem. Jun. 1, 2008;80(11):4175-85. Epub May 6, 2008.

Wilson et al., In vitro selection of functional nucleic acids. Annu Rev Biochem. 1999;68:611-47. Review.

Wlotzka et al., In vivo properties of an anti-GnRH Spiegelmer: an example of an oligonucleotide-based therapeutic substance class. Proc Natl Acad Sci U S A. Jun. 25, 2002;99(13):8898-902.

Wochner et al., A DNA aptamer with high affinity and specificity for therapeutic anthracyclines. Anal Biochem. Feb. 1, 2008;373(1):34-42. Epub Sep. 12, 2007.

Wrenn et al., Chemical evolution as a tool for molecular discovery. Annu Rev Biochem. 2007;76:331-49. Review.

Wrenn et al., Synthetic ligands discovered by in vitro selection. J Am Chem Soc. Oct. 31, 2007;129(43):13137-43. Epub Oct. 6, 2007.

Zhu et al., Review article: high-throughput affinity-based technologies for small-molecule drug discovery. J Biomol Screen. Dec. 2009;14(10):1157-64. Epub. Review.

Extended European Search Report for EP 14788205.4, dated Nov. 25, 2016.

Brindley et al., Chemical speed-dating even faster. Chemistry World. 2009. https://www.chemistryworld.com/news/ chemical-speed-dating-even-faster/3000856.article.

EP 14788205.4, Nov. 25, 2016, Extended European Search Report.

U.S. Appl. No. 13/505,872, filed Jul. 16, 2012, Liu et al.

U.S. Appl. No. 14/931,782, filed Nov. 3, 2015, Liu et al.

PCT/US2010/002732, Mar. 1, 2011, Invitation to Pay Additional Fees.

PCT/US2010/002732, May 9, 2011, International Search Report and Written Opinion.

PCT/US2010/002732, May 18, 2012, International Preliminary Report on Patentability.

PCT/US2014/035177, Aug. 18, 2014, International Search Report and Written Opinion.

PCT/US2014/035177, Nov. 5, 2015, International Preliminary Report on Patentability.

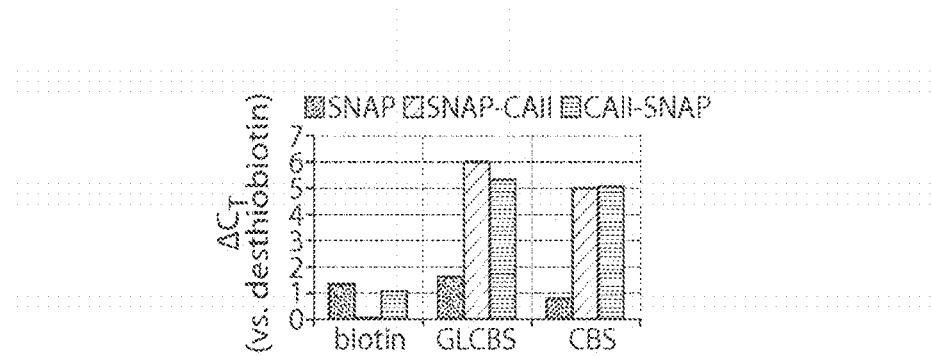
Fig. 10B
Fig. 10C
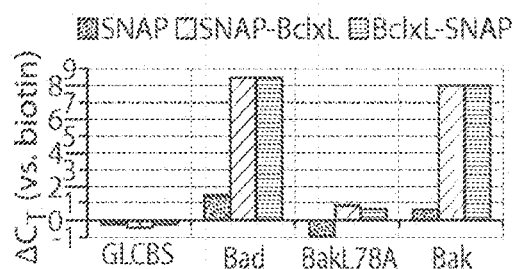
Fig. 10D
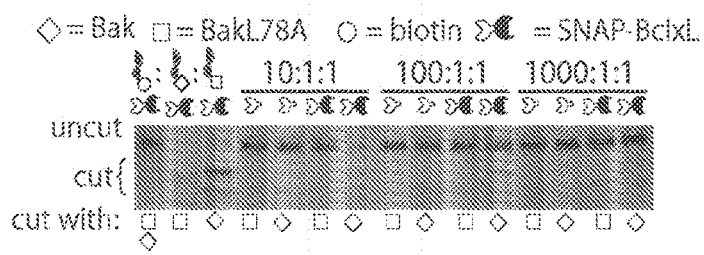
Fig. 10E

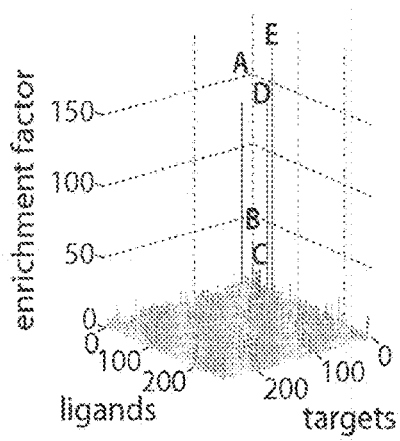
Fig. 23A
| interaction | enrichment factor |
|---|---|
| A: BclxL + Bad | 150.4 |
| B: BclxL + Bak | 47.8 |
| BclxL + BakL78A | 7.2 |
| C: FRB + rapamycin | 23.4 |
| D: CAII + GLCBS | 132.2 |
| E: CAII + CBS | 173.6 |
| mean | 1.4 |
| enrichment factor | presumed false positives |
|---|---|
| 1.43 | 22168 |
| 5 | 2565 |
| 10 | 312 |
| 20 | 9 |
| 23 | 3 |
Fig. 23B
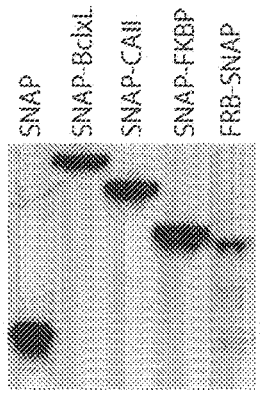
Fig. 23C

IN SITU INTERACTION DETERMINATION

RELATED APPLICATIONS

This application is a national stage filing under 35 U.S.C. § 371 of international PCT application, PCT/US2014/035177, filed Apr. 23, 2014, which claims priority under 35 U.S.C. § 119(e) to United States provisional patent applications, U.S. Ser. No. 61/935,139, filed Feb. 3, 2014, and U.S. Ser. No. 61/815,029, filed Apr. 23, 2013, the entire contents of each of which are incorporated herein by reference.

GOVERNMENT SUPPORT

This invention was made with Government support under grant R01GM065865 awarded by the National Institute of General Medical Sciences and the National Institutes of Health. The Government has certain rights in this invention.

BACKGROUND OF THE INVENTION

Advances in genomic and proteomic studies continue to reveal new targets for therapeutic intervention. The identification of ligands for such targets remains a major opportunity and challenge. To this end, a variety of target-oriented ligand-binding assays have been developed, including affinity selections on DNA-encoded chemical libraries,[1,2] selection-like methods such as interaction-dependent PCR,[3] and a wide variety of screening platforms.[4]

Selections offer substantially improved throughput and decreased time, cost, and material consumption compared to screens, but generally rely on purified, heterologously expressed proteins in an artificial context that includes an immobilized[1] or DNA-linked[3] protein, the compound library, and buffer. Selections conducted in this manner can be incompatible with poorly soluble, aggregation-prone, difficult-to-purify, intrinsically disordered, or membrane-bound targets. Moreover, the results of selections on immobilized targets may lack biological relevance for proteins that adopt non-native conformations or lack binding partners or co-factors essential for their function when taken out of the cellular context.[5] Although a number of successful selections have been conducted using purified proteins,[1] increasing the biological relevance of selection methods will significantly increase their effectiveness.

SUMMARY OF THE INVENTION

This disclosure provides strategies, systems, methods, reagents, and kits for in situ interaction determination (ISID), which is useful to rapidly identify ligand:target interactions from one-pot mixtures of polynucleotide-linked ligands and protein targets. The strategies, systems, methods, reagents, and kits provided herein are particularly useful for identifying such ligand:target interactions in unpurified protein solutions or in complex solutions comprising a significant amount of non-binding molecules, such as, for example, crude biological samples, e.g., cell lysates.

ISID technology is similar in principle to previously-developed PCR-based strategies for detecting chemical reactions or molecular interactions (see PCT application PCT/US2010/002732, filed Oct. 13, 2010; and US Provisional application 61/257,983, filed Nov. 4, 2009, the entire contents of each of which are incorporated herein by reference. Some aspects of this disclosure are based on the recognition that the sensitivity of previous reaction- or interaction-dependent PCR-based strategies can be improved under certain circumstances, e.g., in some embodiments, where ligand:target interactions are screened in particularly complex mixtures, such as crude protein extracts or cell lysates. Some aspects of this disclosure provide strategies for improving the sensitivity of interaction- or reaction-dependent PCR strategies without increasing the number of false positives. These improvements over previous technologies render ISID technology particularly useful for screening ligand:target interactions in samples that are not highly processed or purified, e.g., in samples that contain ligands and/or target molecules (such as target proteins) in their native state. This native state may include, for example, native post-translational modifications and the availability of any interactions with accessory proteins and/or metabolites. By removing the requirement for purified protein targets, the ISID approach enables ligand-binding "selections" to be performed on proteins that are free to undergo post-translational modification, interact with endogenous accessory proteins and metabolites, and access physiologically relevant conformational states.[5]

ISID is triggered by the formation of a ternary complex or a covalent bond involving a polynucleotide-linked ligand, a target molecule (e.g., a target protein), and an oligonucleotide that identifies the target molecule. The association of the target molecule with its corresponding oligonucleotide can be established either non-covalently, e.g., using a polynucleotide-linked binding agent (such as an antibody), or covalently, e.g., using a reactive moiety (such as a self-labeling protein tag that reacts with a polynucleotide-linked small molecule). Formation of this ternary complex is dependent on ligand-target binding and promotes hybridization of short complementary regions on the target- and ligand-linked oligonucleotides. A polymerase can then extend this hybridized region to generate a double-stranded product that contains sequences identifying both the target and its bound ligand. This extension product contains two primer-binding sites and therefore can be amplified by PCR.[3]

Some aspects of this disclosure provide methods for in situ interaction determination (ISID). In some embodiments, the method comprises (i) providing a plurality of nucleic acid templates; (ii) contacting the nucleic acid templates with a target molecule and with a first primer; (iii) incubating the nucleic acid templates contacted with the target molecule and the first primer under conditions suitable for the candidate ligand and the binding moiety to bind to the target molecule; (iv) incubating the nucleic acid templates contacted with the target molecule and the first primer under conditions suitable for the first primer bound to the nucleic acid template via a [candidate ligand]:[target molecule]:[binding moiety] interaction to hybridize with the first primer hybridization site of the nucleic acid template it is bound to for primer extension; (v) contacting the nucleic acid templates contacted with the target molecule and the first primer with a PCR primer complementary to the second primer hybridization site and a PCR primer complementary to the third primer hybridization site, or a PCR primer complementary to the second and the third primer hybridization site; and (vi) performing a polymerase chain reaction (PCR) to amplify a nucleic acid template sequence tag identifying a candidate ligand able to bind to the target molecule. In some embodiments, each nucleic acid template of step (i) comprises a first primer hybridization site; a sequence tag; a second primer hybridization site; and a candidate ligand, wherein the candidate ligand of any specific nucleic acid template is identified by its sequence tag.

In some embodiments, the first primer of step (ii) comprises a sequence complementary to the first primer hybridization site; a third primer hybridization site; and a binding moiety that binds to the target molecule.

In some embodiments, the target molecule of step (ii) is contacted with the nucleic acid templates of step (i) in the presence of accessory molecules and metabolites that are present in a cell expressing the target molecule. In some embodiments, the target molecule of step (ii) is contacted with the nucleic acid templates of step (i) in a biological sample or in the presence of a biological sample. In some embodiments, the biological sample is a crude biological sample, such as a cell lysate, a tissue or biopsy homogenate, a body fluid sample (e.g., a blood, serum, plasma, urine, or saliva sample), or an environmental sample (e.g., a water or soil sample). In some embodiments, the target molecule is a protein. In some embodiments, the target protein comprises a post-translational modification. In some embodiments, the binding moiety of step (ii) binds to the target molecule via a non-covalent interaction. In some embodiments, the binding moiety of step (ii) comprises an antibody or an antigen-binding antibody fragment. In some embodiments, the binding moiety of step (ii) comprises a ligand or a receptor domain. In some embodiments, the binding moiety covalently binds the target molecule. In some embodiments, the target molecule comprises a reactive tag, and wherein the binding moiety reacts with the reactive tag thus covalently binding the first primer to the target molecule. In some embodiments, the reactive tag is a self-labeling tag, e.g., a SNAP-tag, a CLIP-tag, or a Halo-tag.

In some embodiments, the method further comprises contacting the nucleic acid templates contacted with the target molecule and the first primer with a 3'-exonuclease. In some embodiments, the contacting with the 3'-exonuclease is effected before or simultaneously with primer extension. For example, in some embodiments, step (iv) comprises contacting the nucleic acid templates contacted with the target molecule and the first primer with a polymerase. In some embodiments, the polymerase is a DNA polymerase. In some embodiments, the polymerase exhibits 3'-exonuclease activity.

In some embodiments, the method further comprises (vii) identifying the nucleic acid template sequence tag amplified in step (vi). In some embodiments, the identifying comprises sequencing. In some embodiments, the method further comprises (viii) identifying the candidate ligand associated with the sequence tag identified in step (vii) by the nucleic acid sequence of the sequence tag. In some embodiments, the method further comprises (ix) identifying the first primer sequence tag amplified in step (vi). In some embodiments, the identifying comprises sequencing. In some embodiments, the method further comprises (x) identifying the candidate binding molecule associated with the sequence tag identified in step (ix).

In some embodiments, the first primer hybridization site is between about 5 and about 16 nucleotides long. In some embodiments, the first primer hybridization site is 5, 6, 7, 8, 9, or 10 nucleotides long. In some embodiments, the second and the third primer hybridization site are the same nucleic acid sequence. In some embodiments, the PCR primer complementary to the second primer hybridization site and the PCR primer complementary to the third primer hybridization site are the same nucleic acid sequence. In some embodiments, the second and the third primer hybridization site are different nucleic acid sequences. In some embodiments, the first primer hybridization site and the third primer hybridization site overlap or are identical. In some embodiments, the sequence tag is about 5 to about 30 nucleotides long. In some embodiments, the candidate ligand is selected from the group consisting of a peptides, nucleic acids, and small organic compounds.

In some embodiments, the binding between the candidate ligand and the target molecule is characterized by a $K_D<10^{-5}$. In some embodiments, the binding between the candidate ligand and the target molecule is characterized by a $K_D<10^{-6}$. In some embodiments, the binding between the candidate ligand and the target molecule is characterized by a $K_D<10^{-8}$. In some embodiments, the binding between the candidate ligand and the target molecule is characterized by a $K_D<10^{-10}$. In some embodiments, the conditions suitable for hybridization of the nucleic acid sequence complementary to the first primer hybridization site to the first primer hybridization site and primer extension are conditions not allowing for efficient primer site hybridization and primer extension of first primer not connected to a nucleic acid template by a candidate ligand:target molecule interaction characterized by a $K_D<10^{-5}$. In some embodiments, the conditions suitable for hybridization of the nucleic acid sequence complementary to the first primer hybridization site to the first primer hybridization site and primer extension are conditions not allowing for efficient primer site hybridization and primer extension of first primer not connected to a nucleic acid template by a candidate ligand:target molecule interaction characterized by a $K_D<10^{-6}$.

In some embodiments, the PCR is quantitative, real-time PCR. In some embodiments, the PCR comprises 15-32 cycles, wherein each cycle comprises: a denaturation step of 0.1-20 minutes incubation at 85-110° C.; an annealing step of 0.1-20 minutes incubation at 37-78° C.; and an elongation step of 0.1-20 minutes incubation at 62-85° C. In some embodiments, the PCR comprises 15-32 cycles, wherein each cycle comprises a denaturation step of 0.5 minutes incubation at 95° C.; an annealing step of 0.5 minutes incubation at 58° C.; and an elongation step of 0.5 minutes incubation at 72° C.

Some aspects of this disclosure provide kits for in situ interaction determination (ISID). In some embodiments, the kit comprises (i) a first primer, comprising a sequence complementary to a first primer hybridization site of a nucleic acid template; a second primer hybridization site, and a binding moiety; (ii) a second primer complementary to the second primer hybridization site; and (iii) a third primer complementary to a third priming site of the nucleic acid template. In some embodiments, the binding moiety comprises a ligand, an antibody or antibody fragment, or a reactive moiety. In some embodiments, the reactive moiety reacts with a self-labeling tag to form a covalent bond between the first primer and the tag. In some embodiments, the kit further comprises (iv) a 3' exonuclease, for example, a DNA polymerase having 3'-exonuclease activity. In some embodiments, the kit further comprises a PCR buffer; a nucleotide mix; and/or a thermophilic polymerase.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

Figure 1:
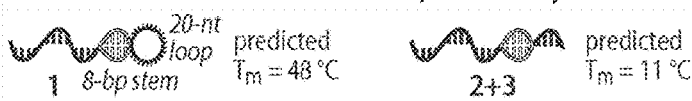
FIG. 1. Reactivity-dependent (RD) and interaction-dependent (ID)-PCR uses differences in intermolecular vs. intramolecular duplex stability to selectively amplify nucleic acids encoding binding ligand:target pairs.
Figure 1:
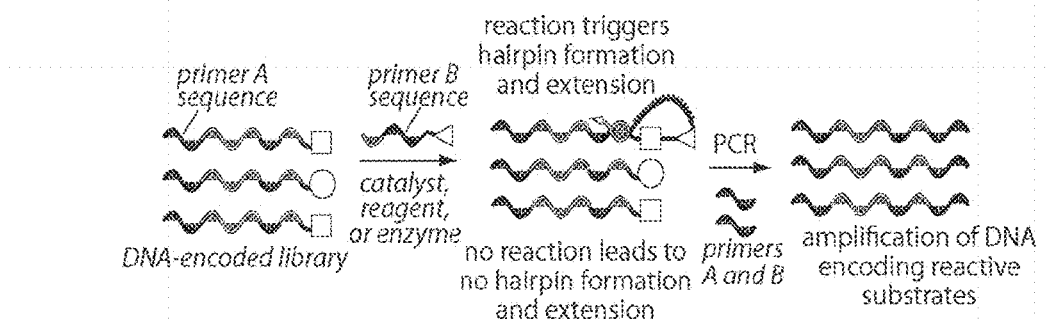
Figure 1:
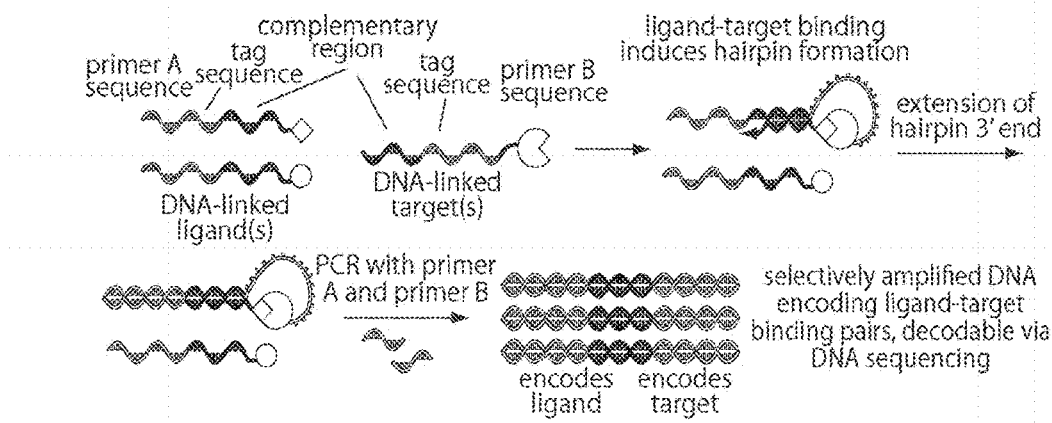

E) ISID on a mock library containing mixtures of DNA-GLCBS and DNA-desthiobiotin shows ~10-fold enrichment of a sequence corresponding to CAII:GLCBS. CBS: 4-carboxy benzene sulfonamide; CA: carbon anhydrase; and GLCBS: Gly-Leu-CBS.

FIG. 9. A) ISID using DNA-αHis and genetically encoded $His_6$-tagged target proteins. B) ISID using DNA-αHis with 293T cell lysate expressing CAII-$His_6$ shows rapid amplification of sequences corresponding to CA:GLCBS and CA:CBS but not CA:desthiobiotin ($\Delta C_T$=5-6). D) ISID using a mock library shows ~10-fold enrichment of the sequence corresponding to CAII:GLCBS, and (F) ~100-fold enrichment of a sequence corresponding to CAII:CBS. E) When the transfected lysate was diluted 1:10 into untransfected lysate, the enrichment of the CAII:GLCBS sequence increased to ~100-fold. C) ISID using DNA-αHis with 293T cell lysate expressing $His_6$-BclxL shows rapid amplification of DNA-Bad but not DNA-GLCBS or DNA-biotin ($\Delta C_T$=8) and (G) ~100-fold enrichment of a sequence corresponding to Bcl-xL:Bad.

FIG. 10. A) ISID in cell lysate expressing a SNAP-tagged target protein. DNA in samples corresponding to known interactions were rapidly amplified in ISID (B: SNAP/CAII: (GL)CBS ($\Delta C_T$=5-6), C: SNAP/Bcl-xL:Bad or Bak ($\Delta C_T$=8-9), F: SNAP-FRB:rapamycin ($\Delta C_T$=6), G: FKBP-SNAP: rapamycin ($\Delta C_T$=6). D) A sequence corresponding to CAII: CBS was enriched ~100-fold in a sample expressing either SNAP-CAII (lane 7) or CAII-SNAP (lane 8). E) In samples expressing SNAP-Bcl-xL, a sequence corresponding to the interaction between Bcl-xL:Bak was enriched ~100-fold (lane 11), but no enrichment was observed for a sequence corresponding to BclxL:BakL78A, a weakly binding mutant of the Bak peptide (lane 9). H) Overexpression of FKBP with SNAP-FRB increased the enrichment of a sequence encoding FRB:rapamycin by 10-fold compared to a sample transfected with SNAP-FRB alone. I) Overexpression of FRB with FKBP-SNAP also increased the enrichment of a sequence corresponding to FKBP:rapamycin by 10-fold compared to a sample transfected with FKBP-SNAP alone.

Figures 1, 5:
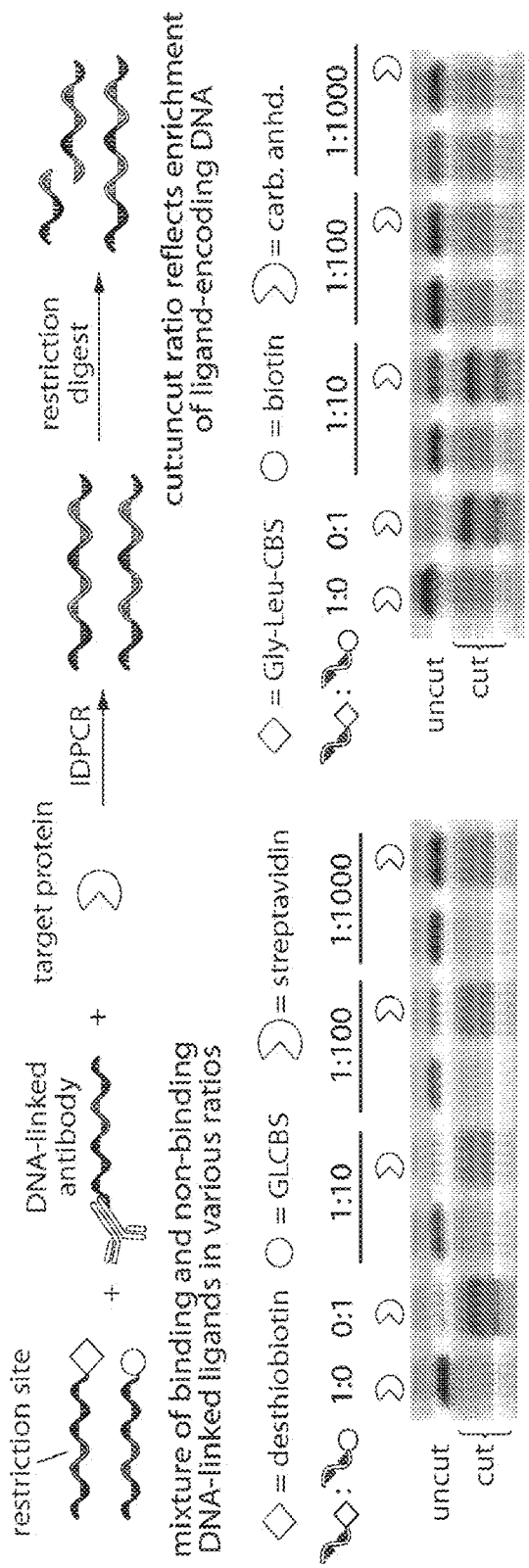
FIG. 5. Antibody ISID enriches known ligands for targets spiked into HeLa lysates. Unmodified streptavidin and carbonic anhydrase were spiked into HeLa lysate at 0.01% w/w. ISID with a mock library of DNA-linked ligands and DNA-linked antibodies for the target proteins allowed good enrichment of their known ligands. For cases in which antibodies are not available or compete with ligand binding, protein affinity tags can be used as a handle for antibody-based IS ID.
Figures 2, 5:
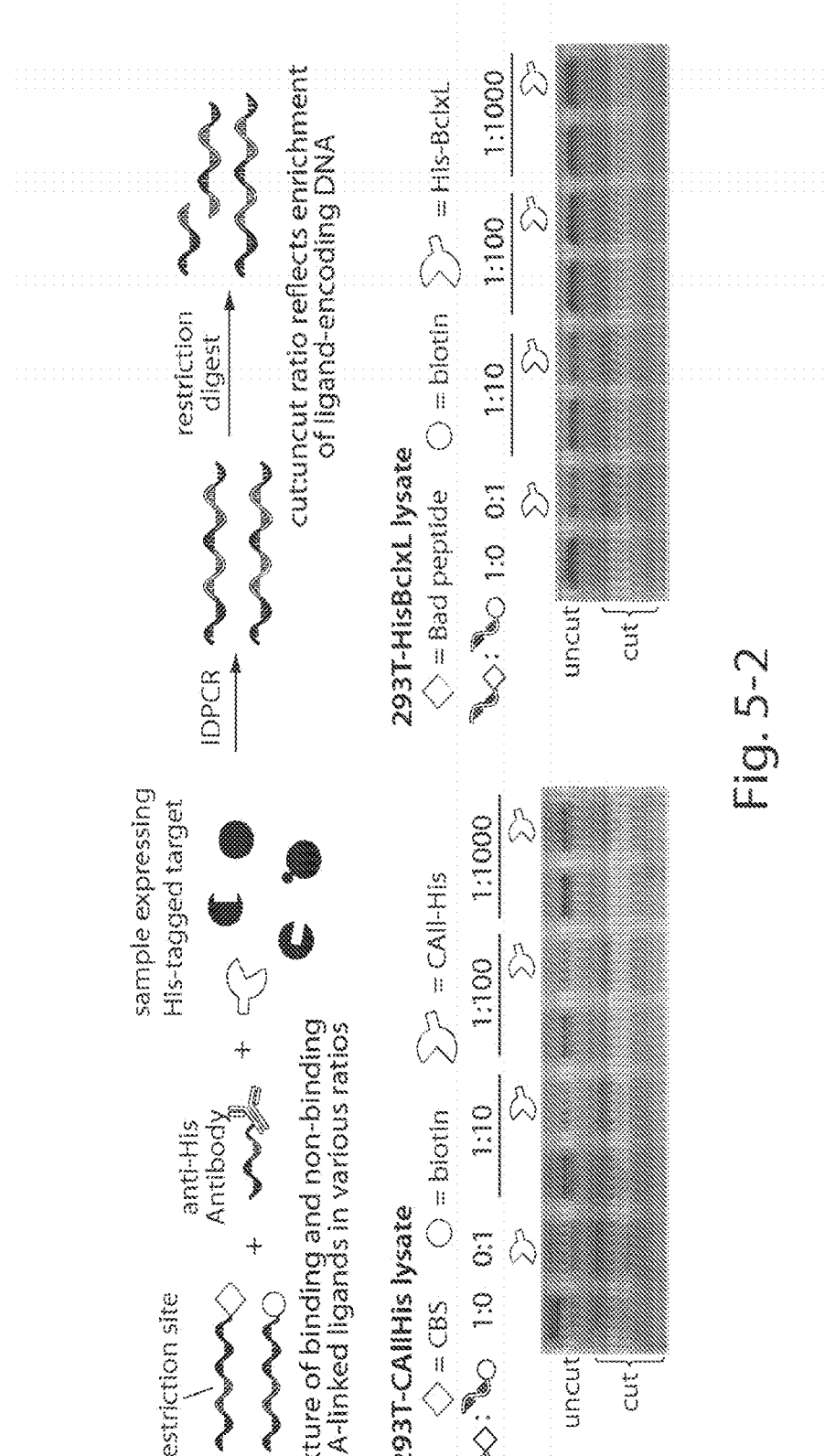

FIG. 5. Selectivity of RD-PCR in a library-format mock selection. PCR conditions: 19 fmol of 12 and 13 in 60 μL, 25-35 cycles.

Figure 11A:
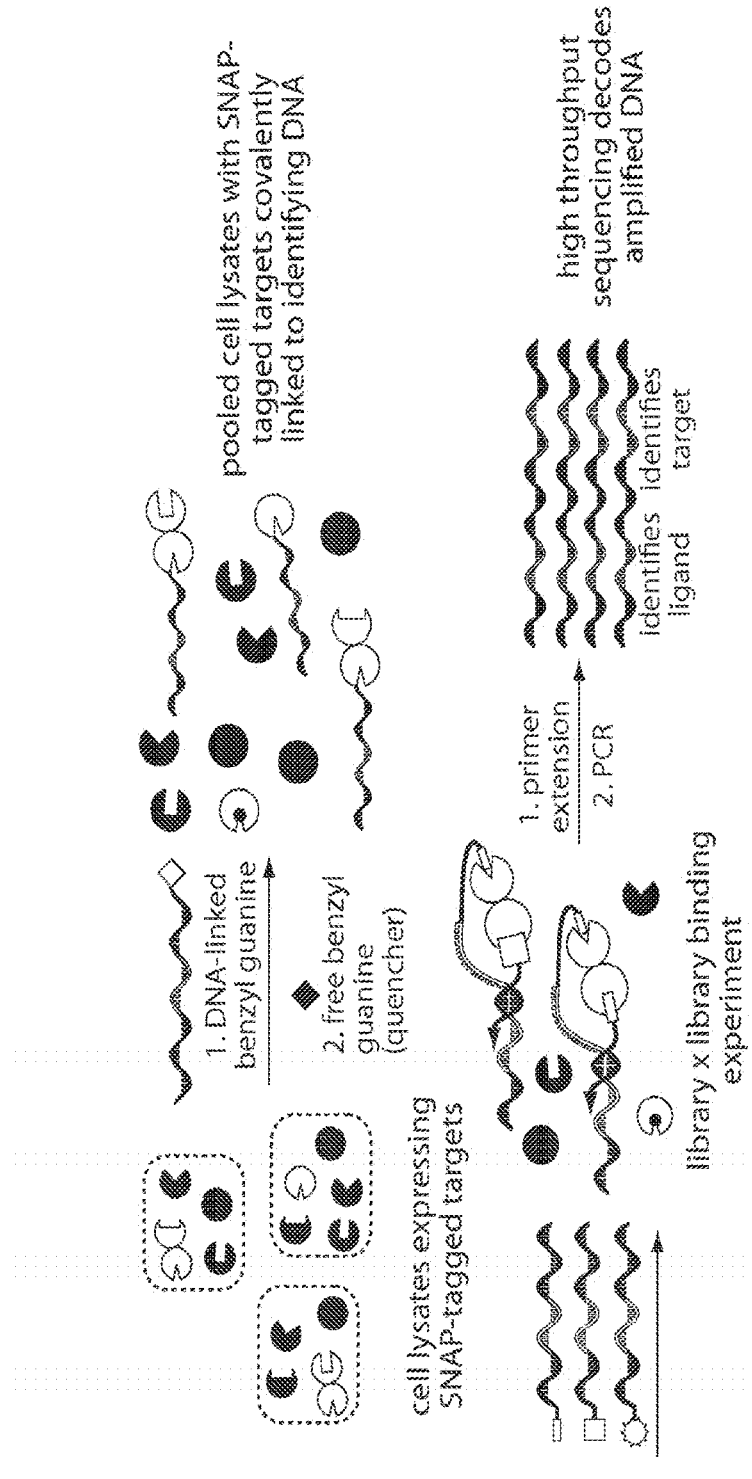
Figure 11B:
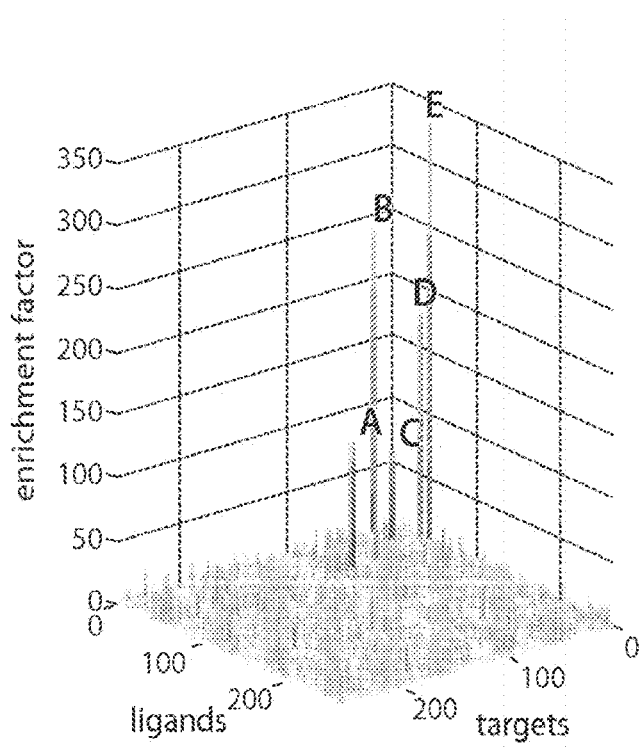

FIG. 11. A) Cell lysates expressing a SNAP-CA, SNAP-Bcl-xL, and SNAP-FKBP were individually labeled with one of three DNA sequences and combined with a cell lysate expressing SNAP and labeled with 256 DNA sequences. The pooled lysates were combined with a library of 262 DNA-linked small molecules, including DNA-linked GLCBS, CBS, Bad, Bak, BakL78A, and rapamycin, for a model library×library ISID "selection." B) ISID using a library of cell lysates expressing SNAP-target fusions identified all five known target:ligand pairs including A: FKBP:rapamycin, B: Bcl-xL:Bad, C: Bcl-xL:Bak, D: CAII:GLCBS, and E: CAII:CBS, despite having affinities from 0.2 nM-3.2 μM. C) For interactions with $K_d$=40 nM to 26 μM, a strong relationship between the log of target-ligand $K_d$ and the number of sequence counts after selection was observed.

Figure 12A:
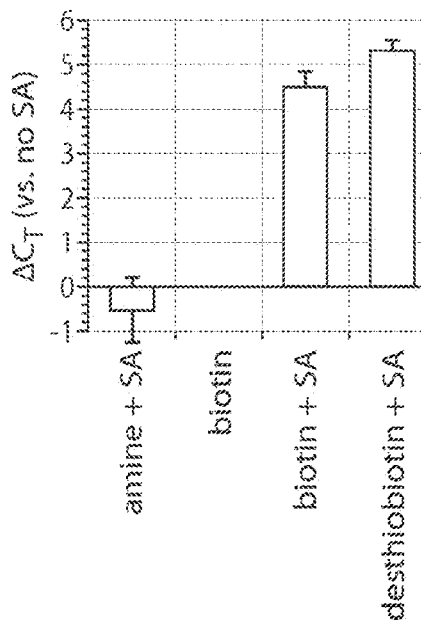
Figure 12B:
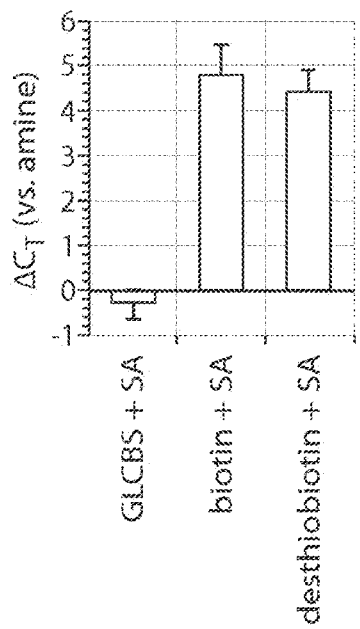
Figure 12C:
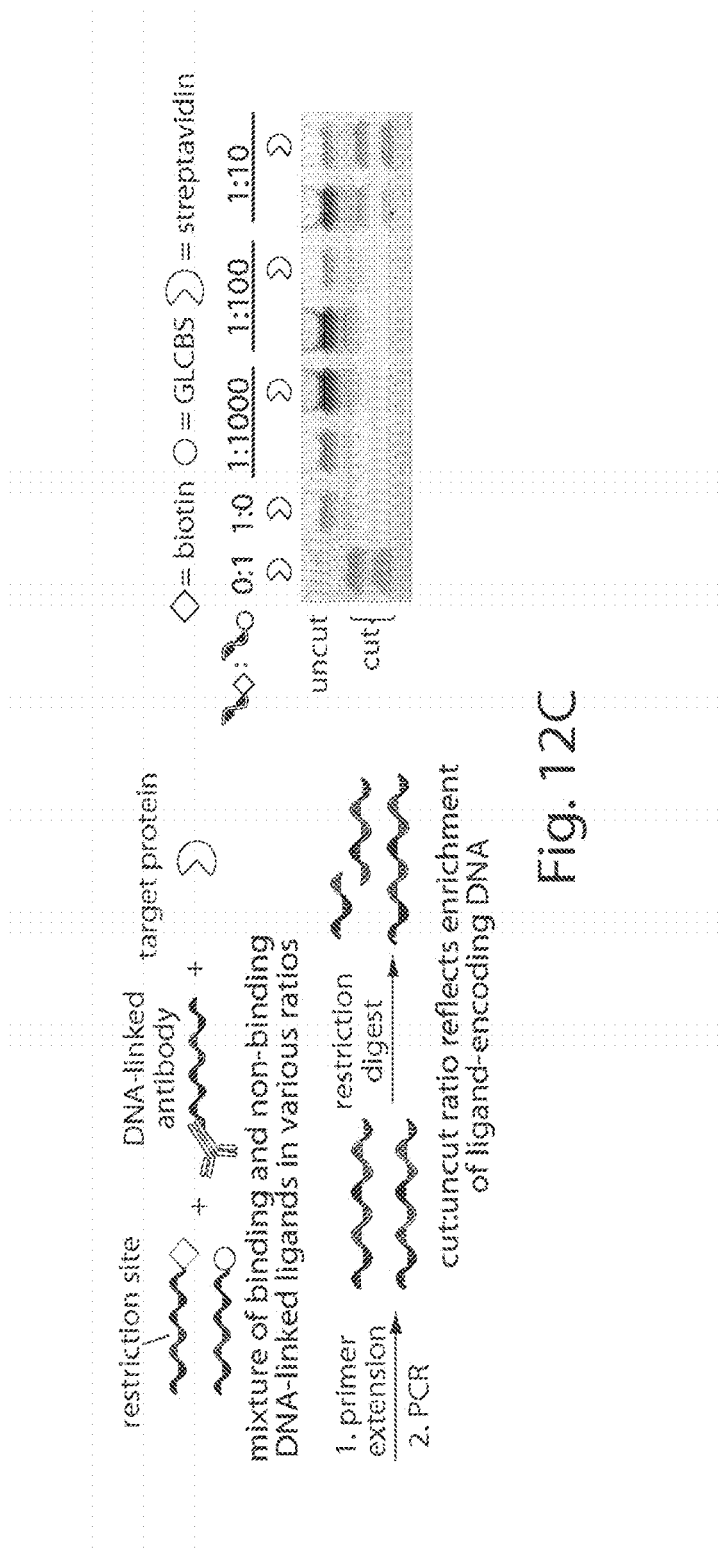
Figure 13A:
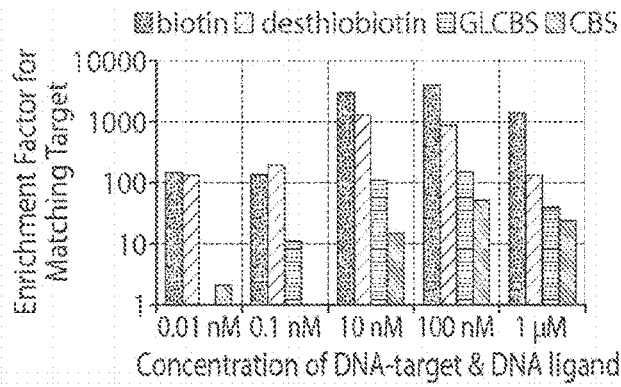
Figure 13B:
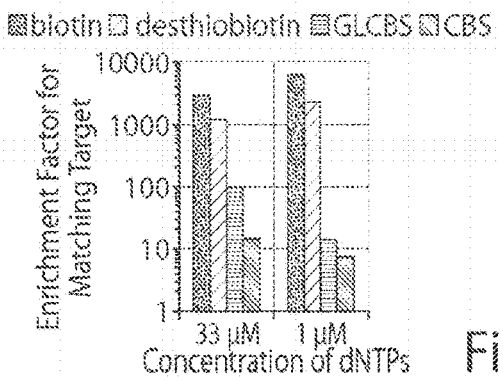
Figure 13C:
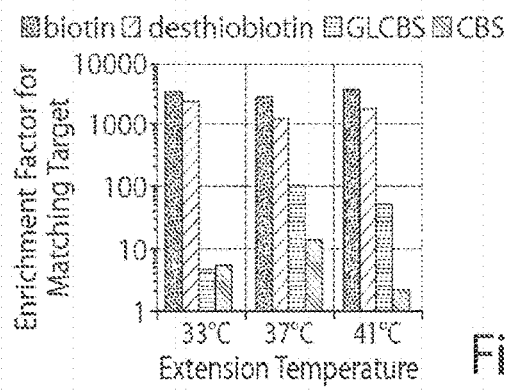
Figure 13D:
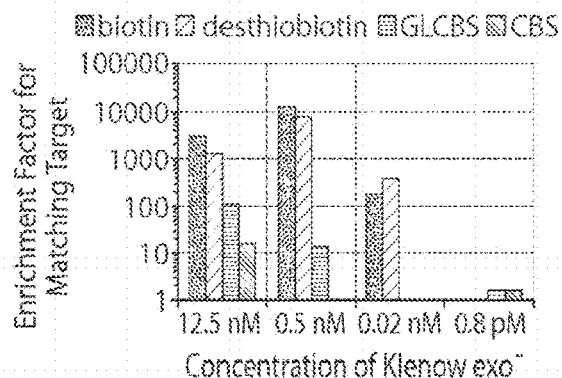

FIG. 12. In Situ Interaction Determination with Klenow exo⁻ and Anti-Streptavidin.

FIG. 13. Model Library×Library Selections with Varied Primer Extension Conditions.

Figure 14:
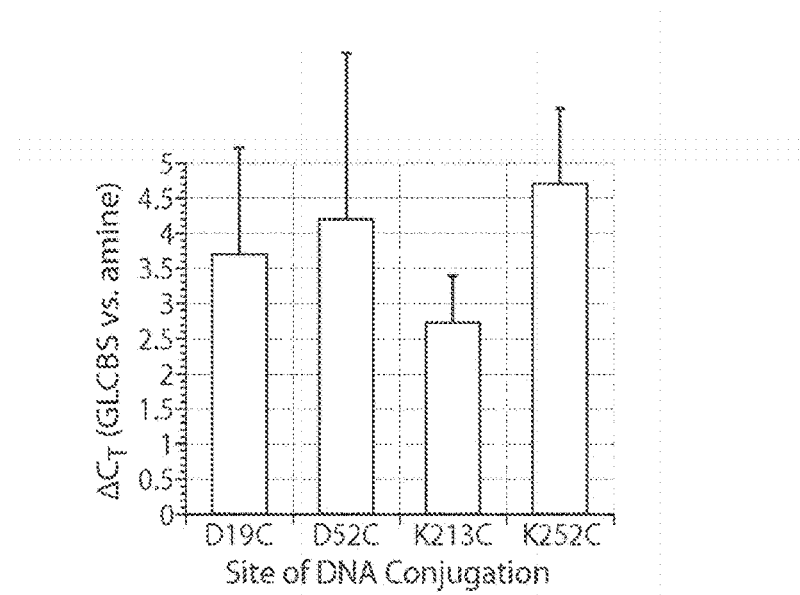

FIG. 14. Effect of Site of Target Labeling on IDPCR.

Figure 15A:
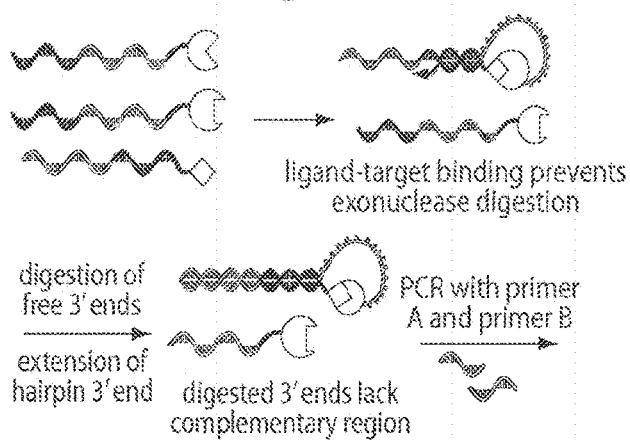
Figure 15B:
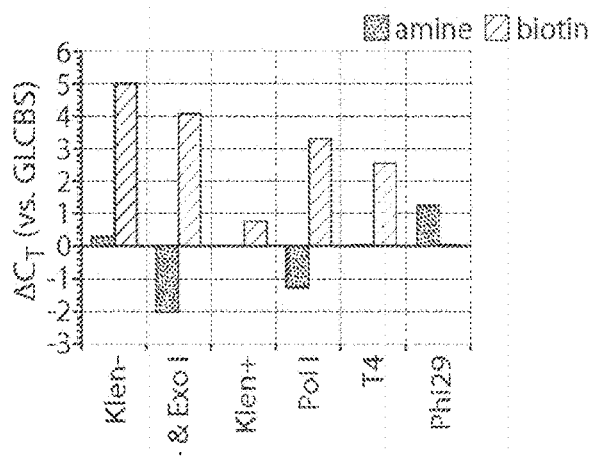
Figure 16A:
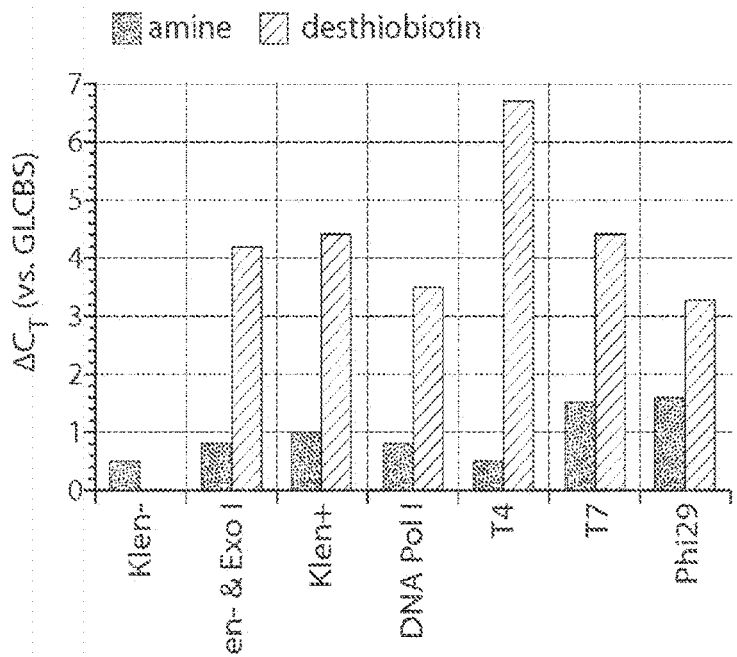
Figure 16B:
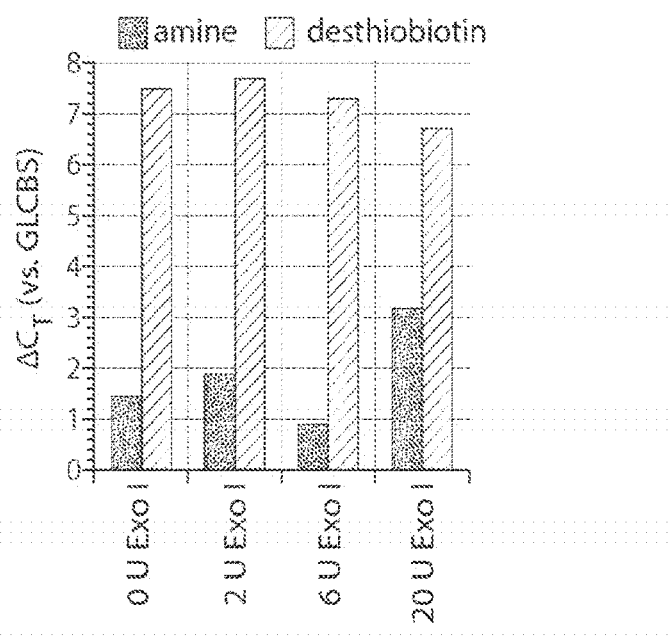
Figure 16C:
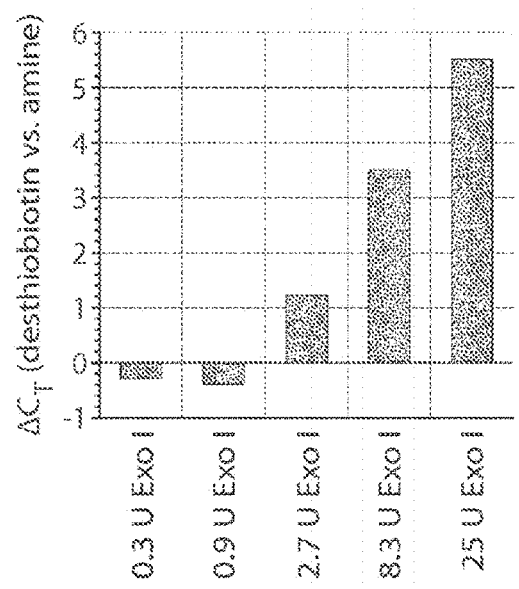
Figure 16D:
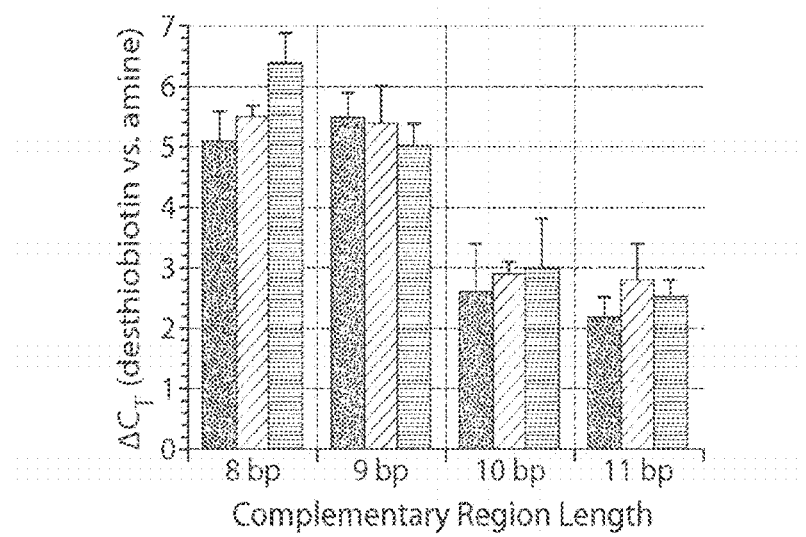

FIG. 15. IS ID with 6 nt complementary region and Various Polymerases.

FIG. 16. Optimization of ISID with 8 nt Complementary Region.

Figure 17:
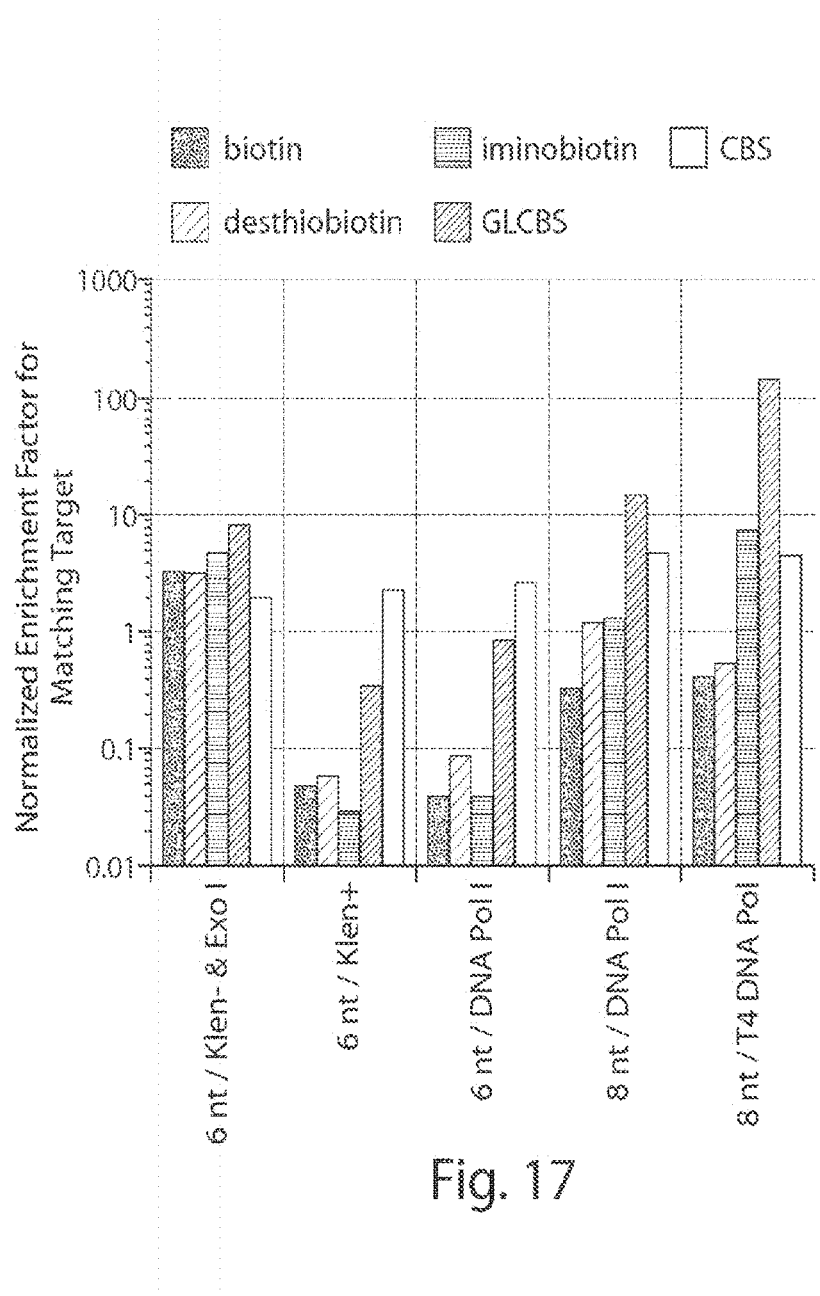

FIG. 17. IDPCR Library×Library Experiments with Various Polymerases.

Figure 18A:
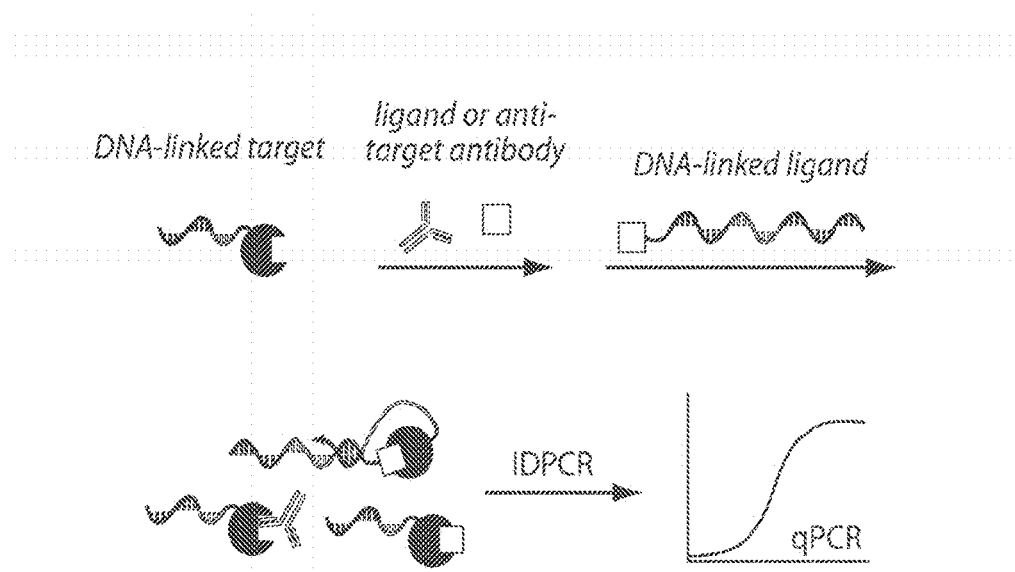
Figure 18B:
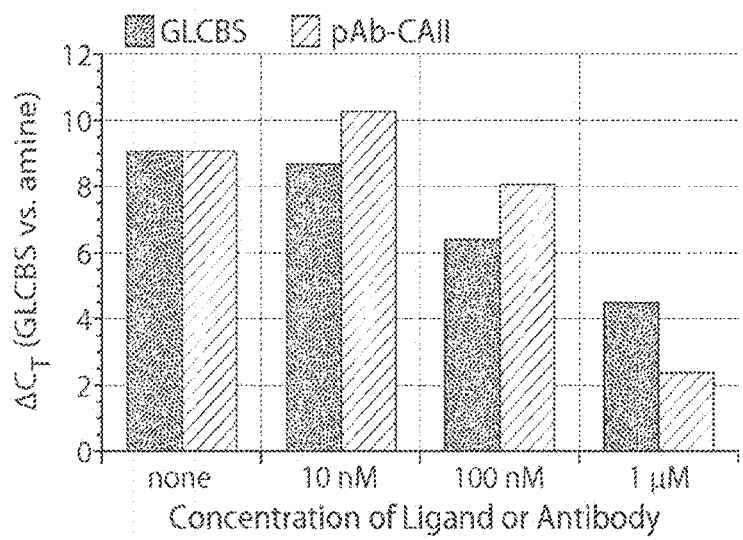

FIG. 18. Polyclonal CAII Antibody Competes with Ligand Binding.

Figure 19A:
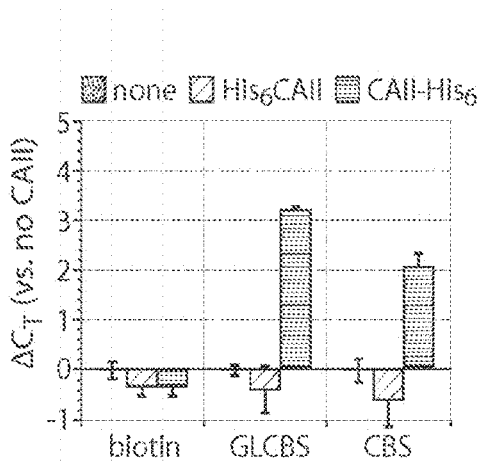
Figure 19B:
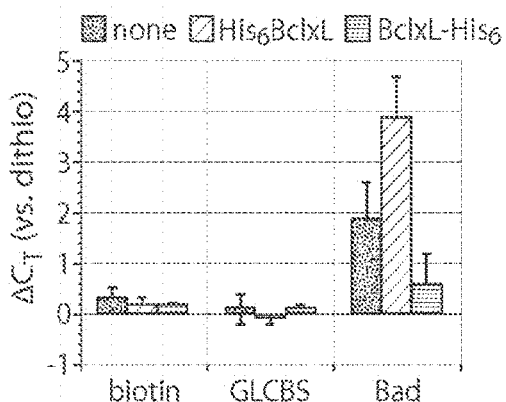
Figure 19C:
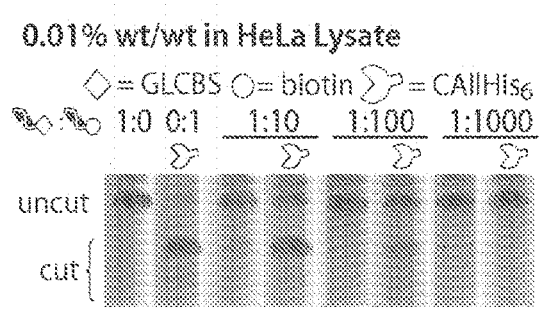

FIG. 19. ISID with DNA-linked αHis and purified CAII-His$_6$ and His$_6$-BclxL.

Figure 20A:
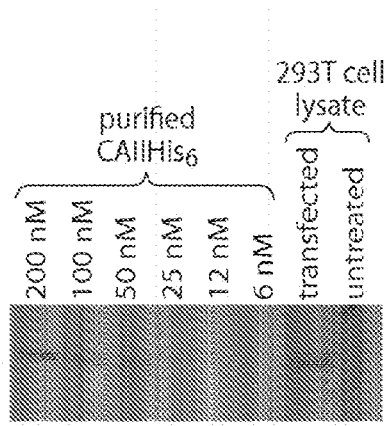
Figure 20B:
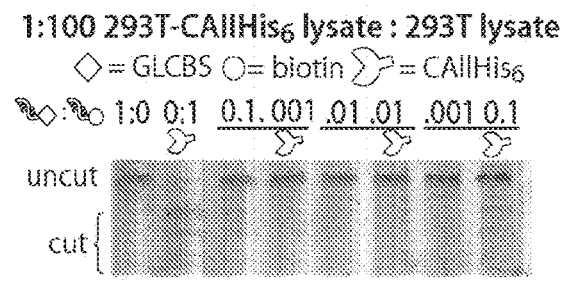
Figure 20C:
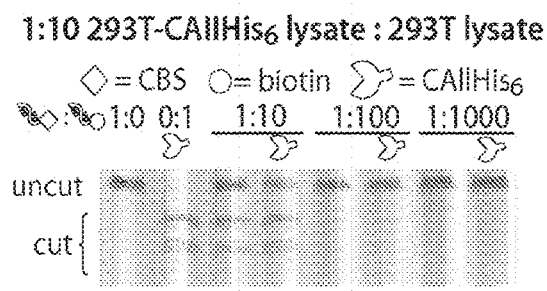
Figure 21A:
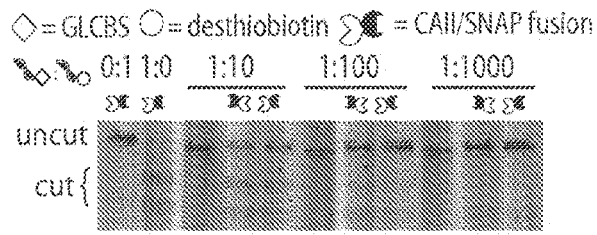
Figure 21B:
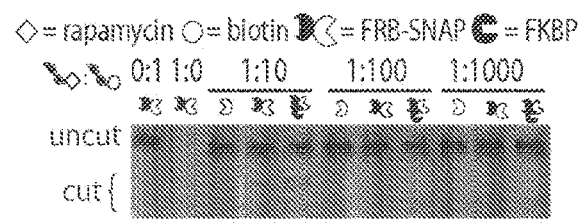
Figure 21C:
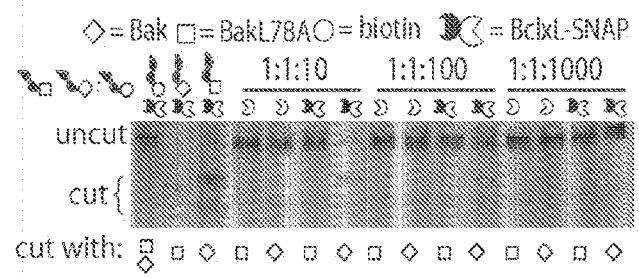
Figure 21D:
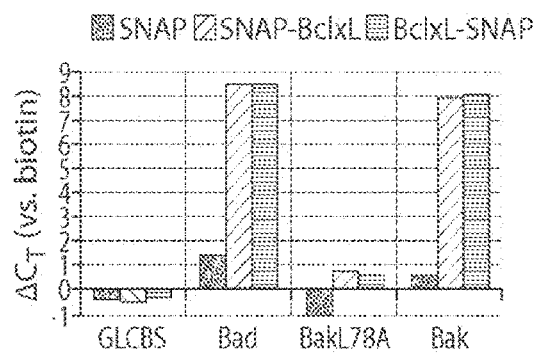

FIG. 20. Expression Level of CAII-His$_6$ in 293T Cell Lysates.

FIG. 21. Target Compatibility with N- and C-terminal SNAP-tag Fusions.

Figure 22A:
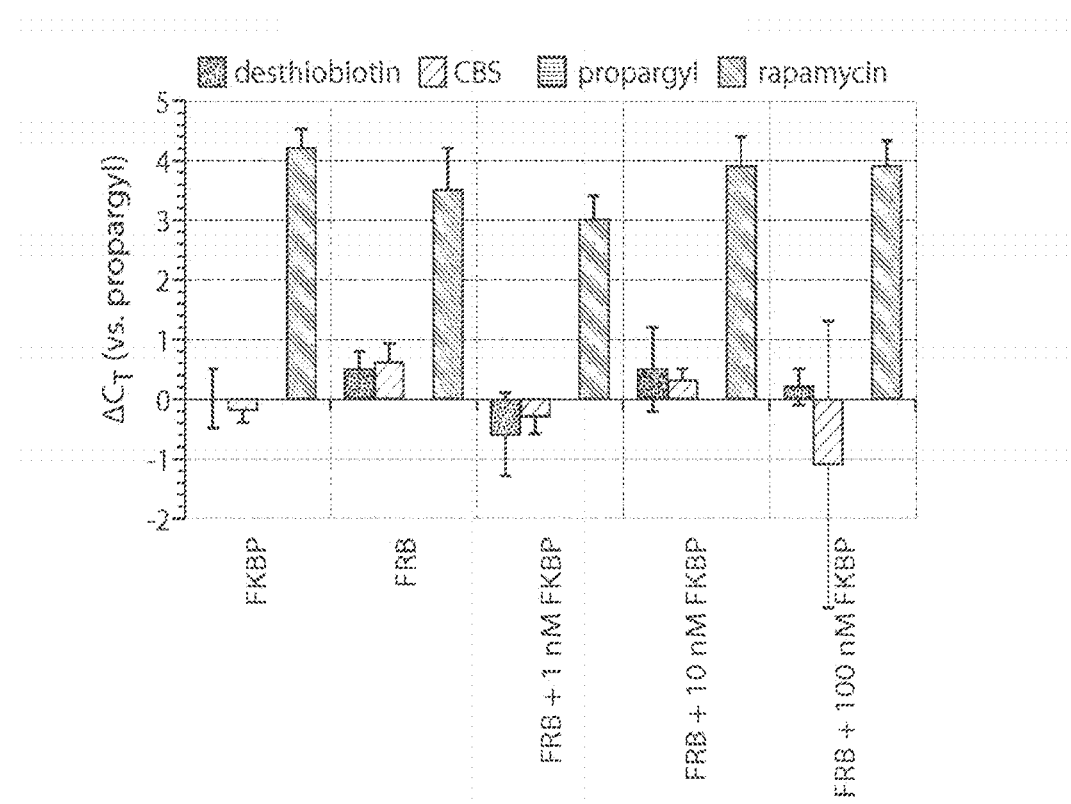
Figure 22B:
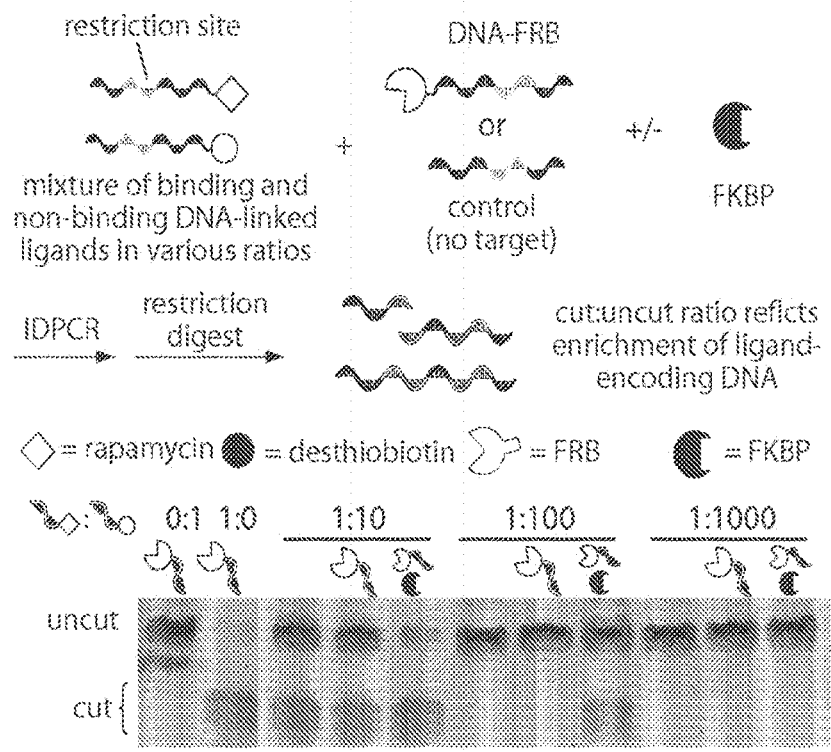

FIG. 22. Preincubating DNA-linked Small Molecules with FKBP Increases Enrichment for DNA-FRB.

FIG. 23. Library×Library Experiment Including FRB-SNAP.

FIG. 24. Library×Library Raw Sequence Counts and Relationship to $K_D$.

DEFINITIONS

As used herein and in the claims, the singular forms "a," "an," and "the" include the plural reference unless the context clearly indicates otherwise. Thus, for example, a reference to "an agent" includes a plurality of such agents.

As used herein, the term "amplicon" refers to a nucleic acid molecule that is amplified in a polymerase chain reaction. In ISID PCR reactions, an amplicon is typically the nucleic acid template or a portion thereof. In library screening ISID PCR reactions, the amplicon typically includes the sequence tag of the nucleic acid template.

As used herein, the term "contacting" refers to bringing a first molecule, for example, a nucleic acid molecule (e.g., a nucleic acid template including a reactive moiety), and a second molecule, for example, a second nucleic acid molecule (e.g. a primer), optionally including a second reactive moiety, together in a manner that the molecules can bind, hybridize, and/or react. Contacting may be accomplished in a cell-free system, for example, by adding a second molecule to a solution including a first molecule under suitable conditions. Conditions suitable for nucleic acid hybridization and various chemical reactions are well known in the art.

As used herein, the term "covalent bond" refers to a form of chemical bonding that is characterized by the sharing of one or more pairs of electrons between atoms. Reactions forming a covalent bond between two reactive moieties are well known in the art, and include, for example, acylation reactions, addition reactions, nucleophilic substitution reactions, cycloaddition reactions, carbonyl chemistry reactions, "non aldol"-type carbonyl chemistry reactions, carbon-carbon bond forming reactions, and addition reactions to carbon-carbon double or triple bonds. A covalent bond formed between two reactive moieties may, for example, be an amide bond, an acyl bond, a disulfide bond, an alkyl bond, an ether bond, or an ester bond. A covalent bond formed between two reactive moieties may be, for example, a carbon-carbon bond, a carbon-oxygen bond, a carbon-nitrogen bond, a carbon-sulfur bond, a sulfur-sulfur bond, a carbon-phosphorus bond, a phosphorus-oxygen bond, or a phosphorus-nitrogen bond.

As used herein the term "enzyme" refers to a molecule, for example, a peptide, a protein, or a nucleic acid (for example, a ribozyme or DNAzyme) that catalyzes a chemical reaction. An enzyme may be a biomolecule (a molecule made by a living organism), a derivative of a biomolecule (e.g., a mutated biomolecule, a fragment of a biomolecule, and/or a fusion product of a biomolecule, or fragment thereof, with a second molecule), or an artificially made molecule (e.g., a synthetic protein or nucleic acid). An enzyme may be an oxidoreductase, transferase, polymerase, hydrolase lyase, synthase, isomerase, or ligase. Accordingly, a protease and a nuclease are non-limiting examples of enzymes. In certain embodiments, the enzyme is a protein. In certain embodiments, the enzyme is a nucleic acid. In certain embodiments, the enzyme is RNA. In certain embodiments, the enzyme is DNA.

As used herein, the term "enzyme substrate" is a molecule upon which an enzyme acts. An enzyme substrate is bound by an enzyme and transformed into one or more products in a chemical reaction catalyzed by the enzyme. The reaction product or products are usually released from the enzyme. For example, a protease catalyzes the hydrolysis of an amide bond in a protease substrate peptide or protein. The substrate peptide of a protease is generally bound specifically, meaning that only a peptide of a certain amino acid sequence or with a sequence similar to a consensus sequence is bound by the protease and cleaved into two or more fragments in a hydrolysis reaction.

As used herein, the term "interaction-dependent polymerase chain reaction" (ID-PCR) refers to a PCR assay in which amplification of a nucleic acid template depends upon the nucleic acid template having a non-covalent association with a PCR primer. The non-covalent association is preferably a high-affinity association, for example, characterized by a $K_D$ of $10^{-6}$ or less. The non-covalent association may be formed between a ligand attached to the nucleic acid template and a binding molecule attached to the primer.

The term "ligand" as used herein, refers to a binding molecule that binds non-covalently to a second binding molecule with high affinity. In some embodiments, a high-affinity bond is characterized by a $K_D<10^{-5}$, a $K_D<10^{-6}$, a $K_D<10^{-7}$, a $K_D<10^{-8}$, a $K_D<10^{-9}$, a $K_D<10^{-10}$, a $K_D<10^{-11}$, or a $K_D<10^{-12}$. In some embodiments, the ligand is a small molecule. In some embodiments, the ligand is a peptide or protein. In some embodiments, the ligand is a nucleic acid.

As used herein, the term "library of nucleic acid templates" refers to a plurality of nucleic acid templates. In some embodiments, each nucleic acids template of a library of nucleic acid templates is bound to one of various reactive moieties. In some embodiments, a library of nucleic acid templates includes nucleic acid templates bound to the same type of reactive moiety, for example, a library of polypeptide-associated nucleic acid templates may include only nucleic acid templates bound to polypeptides. In some embodiments, each nucleic acid template is bound to a specific reactive moiety, wherein the specific reactive moiety a nucleic acid template is bound to can be identified by the nucleic acid template's sequence tag. For example, a specific sequence tag may identify a peptide-associated nucleic acid template to be bound to the peptide Ala-Pro-Gly-Phe-Ala (SEQ ID NO: 32), whereas a different nucleic acid template of the same library with a different sequence tag is bound to a different peptide.

The term "melting temperature" ($T_m$) is an art-recognized term and refers to the temperature at which hybridization of two nucleotide strands is destabilized so that the two nucleotide strands separate (or dissociate). In PCR, the melting temperature is the temperature at which a primer hybridized to a template dissociates from the template.

As used herein, the term "non-covalent bond", interchangeably used with the term "non-covalent interaction" herein, refers to a type of interaction between two molecules that does not involve the sharing of electrons between the molecules, but involves variations of electromagnetic, electrostatic, or hydrophobic interactions.

As used herein, the term "nucleic acid," interchangeably used with the terms "nucleic acid template," "nucleic acid molecule," "polynucleotide," and "oligonucleotide," refers to a polymer of nucleotides. Typically, a polynucleotide comprises at least two nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, 2'-methoxyribose, 2'-aminoribose, ribose, 2'-deoxyribose, arabinose, and hexose), and/or modified phosphate groups (e.g., phosphorothioates and 5'-N phosphoramidite linkages). Enantiomers of natural or modified nucleosides may also be used. Nucleic acids also include nucleic acid-based therapeutic agents, for example, nucleic acid ligands, siRNA, short hairpin RNA, antisense oligonucleotides, ribozymes, aptamers, and SPIEGELMERS™, oligonucleotide ligands described in Wlotzka, et al., *Proc. Natl. Acad. Sci. USA*, 2002, 99(13): 8898, the entire contents of which are incorporated herein by reference. A nucleic acid may further include a non-nucleic acid moiety or molecule, for example, a reactive moiety or a binding molecule, such as a ligand.

As used herein, the term "nucleic acid linker" refers to a nucleic acid molecule including a primer hybridization site. A nucleic acid linker may be single-stranded or double-stranded. A double-stranded nucleic acid linker may include a nucleic acid overhang compatible with a specific restriction site in a ligation reaction. Alternatively, a double-stranded nucleic acid linker may be blunt-ended. A nucleic acid linker may be ligated to a nucleic acid molecule in order to add a primer hybridization sites or a restriction site.

The term "polymerase chain reaction" (PCR) is an art recognized term and refers to a method of amplifying a nucleic acid molecule. PCR uses thermal cycling, consisting of cycles of repeated heating and cooling of a PCR sample including the nucleic acid molecule to be amplified. A typical PCR cycle includes a denaturation (or melting) step, an annealing step, and an elongation (or extension) step. A typical PCR includes between 12 and 40 cycles. A PCR may further include an initialization step, for example, if each activation of a hot start polymerase is performed, a hold step, a final extension or hold step, and a final cooling step. PCR reagents include a buffer, for example, a buffer including $Mg^{2+}$ ions, one or more primers, nucleotides, and a thermophilic polymerase, for example, Taq, Pfu, Pwo, Tfl, rTth, Tli, Tma, Bst, 9° $N_m$, Vent, or Phusion polymerase. A PCR product is a nucleic acid generated as a result of a PCR. PCR protocols are well known in the art, for example, as described in Chapter 8 ("In vitro amplification of DNA by the polymerase chain reaction") of Sambrook et al., *Molecular Cloning: A laboratory Manual, Volumes* 1-3, Cold Spring Harbor Laboratory Press, 2001. Reagents and reagent kits for PCR are available from numerous commercial suppliers.

The term "quantitative PCR" (qPCR) refers to a method used to measure the quantity of a PCR product. If the quantity of a PCR product is measured in real time, the method is referred to as "quantitative, real-time PCR".

A "polypeptide", "peptide", or "protein" comprises a string of at least three amino acids linked together by peptide bonds. The terms "polypeptide", "peptide", and "protein", may be used interchangeably. Peptide may refer to an individual peptide or a collection of peptides. Inventive peptides preferably contain only natural amino acids, although non natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In one embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

As used herein, the term "primer" refers to a nucleic acid molecule that can hybridize to a primer hybridization site of a nucleic acid template via base pairing and that can be elongated by a polymerase, for example, Taq, Pfu, Pwo, Tfl, rTth, Tli, Tma, Bst, 9° $N_m$, Vent, or Phusion polymerase during a PCR. A primer, accordingly, includes a free 3'-OH group or other group amenable to the addition of nucleotide monomers by a polymerase. In some embodiments, only a 3' portion of the primer hybridizes to the primer hybridization site. In other embodiments, the whole primer hybridizes to the primer hybridization site. A primer includes a nucleotide sequence complementary to that of the primer hybridization site it hybridizes to. It should be noted, that primer hybridization may tolerate nucleotide-nucleotide mismatches, and, therefore, "complementary" does not require complete complementarity, but only a degree of complementarity sufficient for hybridization. Typically, a primer includes between 18 to 35 nucleotides. However, a primer may be longer or shorter than that, for example, ranging in length from 5-100 nucleotides. In a PCR, a primer hybridizes with a primer hybridization site of a nucleic acid template during the annealing step, is elongated by nucleotide addition in the elongation step, and the hybridization of elongated primer and template are broken during the denaturing step. If a primer is covalently bound to the nucleic acid molecule including the primer hybridization site, the sequence hybridizing with the nucleic acid template may be as short as 5-10 nucleotides, for example, the hybridizing sequence of the primer may be 5, 6, 7, 8, 9, or 10 nucleotides long.

As used herein, the term "primer extension," interchangeably used with the term "primer elongation", refers to the extension of a primer that hybridizes to a nucleic acid template by the addition of nucleotides complementary to the nucleic acid sequence of the template. In a PCR, this primer extension is usually performed by a thermophilic polymerase, for example, Taq, Pfu, Pwo, Tfl, rTth, Tli, Tma, Bst, 9° $N_m$, Vent, or Phusion polymerase.

As used herein, the term "primer hybridization site" refers to a nucleotide sequence that a primer can hybridize to. A primer hybridization sites may be part of a nucleic acid template. The primer hybridization site may be 100% homologous to the primer sequence, or may be less than 100% homologous (e.g., 99.9%, 99%, 98%, 97%, 96%, 95%, 90%, 85% homologous). The length and sequence of a primer hybridization site is dependent on the specific application. Length and nucleotide sequence can impact PCR parameters such as annealing temperature and cycle length. Usually, a primer hybridization site is between 10-40 bases long. In some embodiments, a primer hybridization site may be shorter than that, depending on primer sequence and intended hybridization parameters. Methods to design primers for annealing and extension in view of hybridization and extension parameters and methods of adapting hybridization and extension conditions in view of specific primer length and/or sequence are well known in the art.

The term "protein," used interchangeably with the term "polypeptide" herein, refers to a molecule including a polymer of amino acid residues linked together by peptide bonds. The term, as used herein, refers to proteins, polypeptides, and peptide of any size, structure, or function. Typically, a protein or polypeptide will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. A protein may be just a fragment of a naturally occurring protein or peptide. A protein may be naturally occurring, recombinant, or synthetic, or any combination thereof.

As used herein, the term "reactive moiety" refers to a molecular entity or functional group able to form a covalent bond with another reactive moiety. Accordingly, a reactive moiety may include a reactive functional group, for example, an alkenyl, alkynyl, phenyl, benzyl, halo, hydroxyl, thiol, carbonyl, aldehyde, carbonate ester, carboxylate, carboxyl, ether, ester, carboxyamide, amine, ketimine, aldimine, imide, azido, diimide, cyanate, isocyanide, isocyanate, isothiocyanate, nitrile, sulfide, or disulfide group. A reactive moiety may be part of a compound. The term "compound" refers to any molecule that is to be tested, for example, for the ability of a reactive moiety of a compound to form a covalent bond with a second reactive moiety. A reactive moiety or a compound containing such a moiety can be randomly selected or rationally selected or designed.

As used herein, the term "reactivity-dependent polymerase chain reaction" (RD-PCR) refers to a PCR assay in which amplification of a nucleic acid template depends upon the nucleic acid template forming a covalent bond with a primer. The covalent bond may be formed between a reactive moiety of the nucleic acid template and a reactive moiety of the primer.

As used herein, the term "sequence tag" refers to a nucleotide sequence used to identify a candidate reactive moiety bound to a nucleic acid molecule or nucleic acid template. For example, in a library screening experiment, a nucleic acid template with a specific first sequence tag may include a specific candidate reactive moiety, while a nucleic acid template with a different sequence tag may include a different candidate reactive moiety. This way, a specific reactive moiety that forms a covalent bond with a target reactive moiety, for example, in a library screen, in which the nucleic acid templates of the library are contacted in parallel, can be identified by sequencing the sequence tag of an RD-PCR product obtained in the screen. Depending on the complexity of the library to be screened, the length of the sequence tag may vary. A single nucleotide in a DNA sequence tag including naturally occurring nucleotides can represent one out of four bases A, C, G and T. Thus, a sequence tag will allow for the identification of 4' nucleic acid templates with n being the number of nucleotides of the sequence tag. For example, a sequence tag including 4 nucleotides could theoretically identify 256 different nucleic acid templates/reactive moieties, a sequence tag including 10 nucleotides could theoretically identify 1,048,576 nucleic acid templates/reactive moieties. In practice, some theoretically possible sequence tags, for example, an all-G tag, may interfere with RD-PCR template amplification. Sequence tags with very high (>80%) or very low (<20%) GC content may cause problems in nucleic acid amplification during RD-PCR or ID-PCR, as may sequence tags showing self-complementarity or complementarity to any part of the nucleic acid template or other nucleic acids used in the RD-PCR or ID-PCR reaction. It is well known to those in the art how to design sequence tags and how to avoid high and low GC-content in designing nucleic acid components, for example, primers and templates, for PCR. As a result, the practical amount of useful tags for a given sequence tag length is lower than the theoretical number of possible sequence tags. Sequence tag length may be determined, for example, by the number of reactive moieties to be tagged and/or the sequencing technology to be used in RD-PCR product sequencing. A library of nucleic acid molecules including sequence tags may include sequence tags of different length, thus increasing the number of usable sequence tags at any given maximum sequence tag length. The term "identifying a sequence tag" refers to determining the nucleotide sequence of a sequence tag.

As used herein, the term "small molecule" is used to refer to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and/or other functional groups (e.g., amines, hydroxyl, carbonyls, heterocyclic rings, etc.). In some embodiments, small molecules are monomeric and have a molecular weight of less than about 1500 g/mol. In certain embodiments, the molecular weight of the small molecule is less than about 1000 g/mol or less than about 500 g/mol. Preferred small molecules are biologically active in that they produce a biological effect, for example, a kinase inhibitor produces inhibition of a kinase, in animals, preferably mammals, more preferably humans. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

As used herein, the term "suitable conditions," interchangeably used with the term "conditions suitable," refers to conditions that are suitable for a specific reaction, interaction, or other event to take place. For example, conditions suitable to form a covalent bond between two reactive moieties may include both reactive moieties, a suitable medium allowing both reactive moieties to interact, for example, an aqueous solution, a reaction cofactor or catalyst, if necessary, a buffering agent, a certain temperature, pH, or osmolarity. The suitable conditions for any given reaction or interaction will, of course, depend on the specific reaction or interaction. Suitable conditions for the reactions or interactions described herein are well known to those in the relevant chemical and molecular biological arts. For example, suitable conditions for nucleic acid hybridization, primer extension, restriction digestion, and linker ligation are described herein and in Sambrook et al., *Molecular Cloning: A Laboratory Manual, Volumes* 1-3, Cold Spring Harbor Laboratory Press, 2001, incorporated herein by reference. Further, suitable conditions for various chemical reactions are described herein and, for example, in Smith and March, *March's Advanced Organic Chemistry: Reactions, Mechanisms, and Structure*, Wiley-Interscience, 6$^{th}$ edition, 2007, incorporated herein by reference. Suitable conditions for covalent bond formation, enzymatic catalysis, and PCR are described herein and well known to those of skill in the art. In some embodiments, suitable conditions for hybridization of a nucleic acid template's primer hybridization site and a primer including a complementary nucleic acid sequence and/or primer extension are conditions allowing for efficient primer site hybridization and/or primer extension if the primer is covalently bound to the nucleic acid template, but not allowing for efficient primer site hybridization and/or primer extension if the primer is not covalently bound to the nucleic acid template.

The term "template," as used herein, refers to a nucleic acid molecule including a primer hybridization site. A template may also include (e.g., be coupled to) a candidate reactive moiety and may include a tag, such as a sequence tag, identifying the attached candidate reactive moiety. A template is typically a DNA molecule.

DETAILED DESCRIPTION

Introduction

Some aspects of this disclosure describe in situ interaction determination (ISID), a method that selectively amplifies polynucleotide sequences identifying ligand:target pairs from a mixture of polynucleotide-linked ligand molecules, e.g., small molecules, and unpurified target molecules, such as target proteins. ISID is a solution-phase technology that is particularly useful for identifying ligand:target binding partners in complex mixtures, such as biological samples, e.g., crude cell, tissue, or biopsy homogenates or lysates, or minimally processed (e.g., unpurified) samples obtained from tissues, cells, biopsies, body fluid samples (e.g., blood, serum, plasma, urine, saliva), or environmental samples (e.g., water or soil samples). Nucleic acid sequences including unique, identifiable sequences, are linked to both the ligand and the target molecule, thus allowing the identification of molecules involved in ligand:target complex formation after amplification and sequencing of the sequence tags. In addition to identifying sequences, the nucleic acid molecules attached to ligand and target molecule comprise short complementary regions that hybridize efficiently only upon formation of a ligand:target complex, but not in the absence of such a complex.

In contrast to conventional ligand:target binding screens that require purified target preparations, ISID can be performed in situ, e.g., by using crude cell lysates or minimally purified lysates or preparations obtained from biological samples, such as, for example, cells, tissues, biopsies, or environmental samples. ISID thus overcomes some of the limitations associated with conventional interaction-detection technologies, for example, in that it allows for the detection of multiple ligand:target interactions in a single screen, it minimizes the risk of denaturing or otherwise altering the target molecule during purification or processing steps, including the alteration of post-translational modifications in target proteins, and it allows for the screening of target molecules, e.g., target proteins, in their native state, including their native conformations, native post-translational modifications, and their native binding partners, substrates, and metabolites. Embodiments of ISID in which the target molecule is a protein and the protein is used in unpurified form are also sometimes referred to as "interaction determination using unpurified proteins" (IDUP) embodiments.

Similar to reactivity-dependent and interaction-dependent PCR methods (RD-PCR and ID-PCR, respectively), e.g., as described in international PCT application PCT/US2010/002732, the entire contents of which are incorporated herein by reference, ISID features identification of ligand:target pairs based on the isolation and amplification of nucleic acid sequences linked to the respective ligand and to the respective target molecule. The nucleic acid sequence comprises a unique sequence tag that identifies, or "encodes," the linked ligand or the linked target. In addition to these unique sequence tags that identify the respective ligand or target, the linked nucleic acids also comprise short complementary regions that can hybridize efficiently to each other only upon formation of a ligand:target complex (see FIG. 1.) The complementary regions are designed such that the melting temperature ($T_m$) of an intramolecular hairpin formed by two complementary regions connected to each other via ligand:target interaction is much higher than that of the corresponding intermolecular duplex in the absence of connecting ligand:target interactions.

ISID thus uses the increased Tm of an intramolecular hairpin to translate ligand:target interactions into a nucleic acid signal encoding the respective ligand and target. As shown in the lower panel of FIG. 1, an intramolecular hairpin triggered by ligand:target interaction can be extended, resulting in a template for PCR that incorporates codes identifying the ligand and the target in a single sequence. The identity of the ligand and the target involved in the ligand:target complex can be decoded by DNA sequencing.

Figure 2:
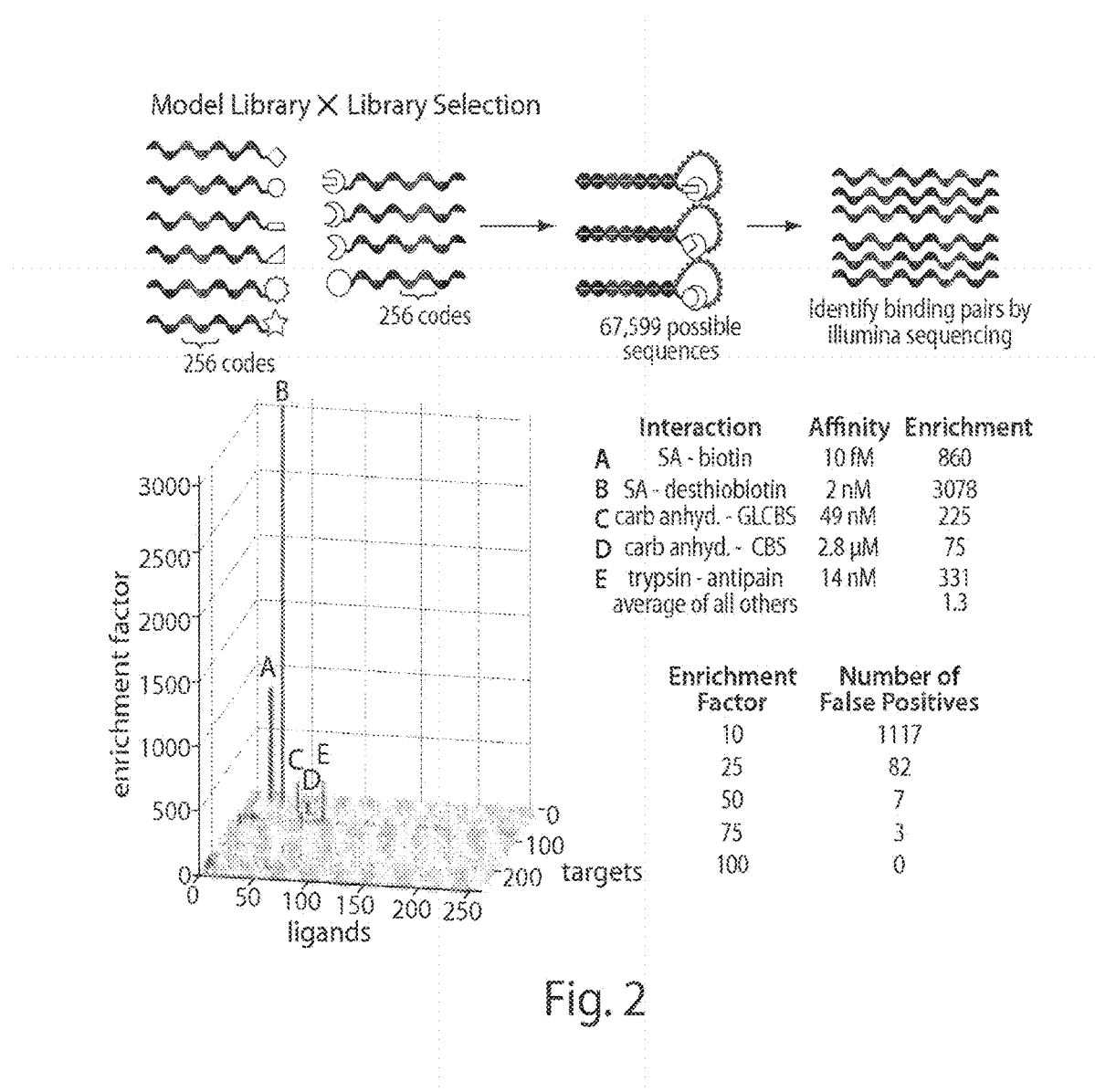
FIG. 2. Model ISID library×library selection. A model library of DNA-encoded ligands mixed with a model library of DNA-encoded targets allows multiplexed detection of binding pairs in a single, solution-phase experiment. A 261-membered DNA-ligand library and a 259-membered DNA-protein library containing five known protein:ligand interactions out of 67,599 possible sequences were exposed to Klenow extension followed by PCR and high-throughput DNA sequencing. For each target protein, the most highly enriched sequence, relative to a control lacking proteins, correspond to known binding ligands.

While ISID technology can be applied in a variety of experimental contexts, it is particularly suitable for library×library selections, in which a library of DNA-linked ligands is screened against a library of DNA-linked target molecules. For example, ISID can be used for processing a library of polynucleotide-linked small molecules and a library containing potential ligands, e.g., a library of cell lysates expressing self-labeling fusion proteins, combined in a single sample. FIG. 2 provides an overview over an exemplary library×library selection scheme, in which ISID allowed the multiplexed detection of binding pairs in a single, solution-phase screening of a 261-membered DNA-ligand library against a 259-membered DNA-protein library. The libraries were mixed and incubated under conditions allowing for ligand:target binding and intramolecular primer duplex formation, followed by exposure to Klenow fragment-mediated extension, PCR, and high-throughput DNA sequencing. For each target protein, the most highly enriched sequence, relative to a control lacking proteins, correspond to known binding ligands. ISID was able to identify five known protein:ligand interactions against a background of 67,599 possible combinations. In another exemplary model "library×library" experiment, ISID resulted in enrichment of sequences corresponding to five known ligand:target pairs ranging in binding affinity from $K_d$=0.2 nM to 3.2 µM out of 67,858 possible combinations, with no false positive signals enriched to the same extent as that of any of the bona fide ligand:target pairs.

Typically, ISID technology involves the identification of ligand:target interactions based on the formation of a ternary complex or a covalent bond between a polynucleotide-linked ligand (e.g., a small molecule ligand) and a polynucleotide-linked target molecule (e.g., a target protein) in situ, e.g., in a crude cell lysate or in an unprocessed or minimally processed sample, such as a cell or tissue culture sample, a tissue sample, a biopsy, or an environmental sample. In some embodiments, target molecules, e.g., target proteins, are associated with oligonucleotide tags in situ either noncovalently using a polynucleotide-linked antibody, or covalently using a reactive tag, such as a self-labeling protein tag (e.g., a SNAP-tag).

ISID technology can be used for identifying ligand:target interactions in complex samples, for example, in crude cell lysates or in other samples in which the target molecule is provided in an unprocessed or only minimally processed form. One advantage of screening for ligand:target interactions in situ, e.g., in crude cell lysates or in unprocessed or minimally processed samples is that a given target molecule can be evaluated in a state that closely resembles its native state in vivo, e.g., in its native environment. For example, analyzing ligand:target protein interactions in cell lysates allows for the provision of the target protein(s) with intact secondary modifications, such as glycosylations, and also for interactions with accessory molecules, such as accessory proteins, and metabolites to occur. Some ISID embodiments thus preserve the native state of a target molecule, such as post-translational modifications and interactions with endogenous binding partners, thereby enabling the study of difficult-to-purify targets and increasing the potential biological relevance of detected interactions compared with methods that require purified proteins.

The detection of ligand:target molecule interaction in situ can be challenging, because of the complexity of the unpurified or minimally processed samples involved, which may result in an abundance of false positives. Some aspects of this disclosure relate to the surprising discovery that the instantly disclosed improvements to previously known interaction- and reaction-dependent PCR technologies (see, e.g., PCT application PCT/US2010/002732, the entire contents of which are incorporated herein by reference) significantly improves the performance of such technologies regarding the identification of ligand:target molecule interactions in samples that have not been purified, including in crude cell lysates.

For example, some aspects of this disclosure are based on the discovery that a reduction of false positive PCR amplicons that are typically associated with complex samples, such as crude cell lysates and other minimally processed samples, can be achieved by digesting unprimed nucleotide sequences with a 3' exonuclease before or during the first primer extension step, as explained in more detail elsewhere herein. Accordingly, some aspects of this disclosure provide strategies and methods for the reduction of background or false positives, thus removing the requirement for purified protein targets that limits the application of some of the previously known methods for the detection of ligand:target molecule interactions in complex samples such as cell lysates or unpurified, unprocessed or minimally processed samples. The ISID approach thus enables ligand-binding "selections" to be performed on proteins that are free to undergo post-translational modification, interact with endogenous accessory proteins and metabolites, and access physiologically relevant conformational states.[5]

Figure 3:
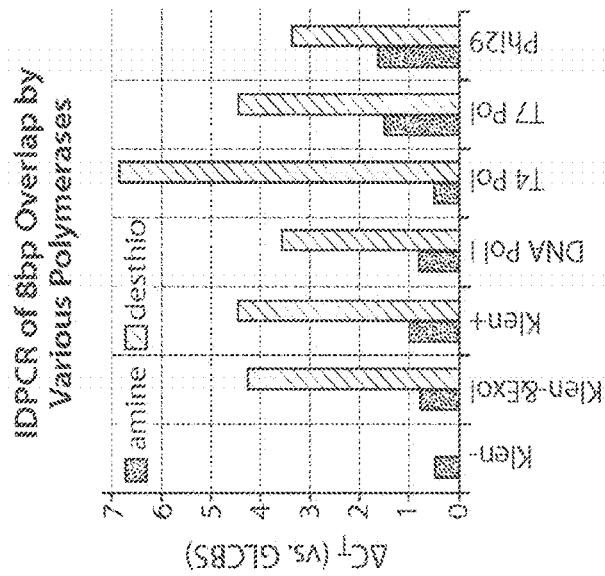
FIG. 3. Exonuclease exposure reduces background signal. Hybridized sequences resulting from ligand:target binding are polymerase substrates. In contrast, single-stranded sequences conjugated to unbound protein are substrates for 3' exonucleases. Digestion of their 3' ends will remove the complementary region, reducing background signal.
Figure 3:
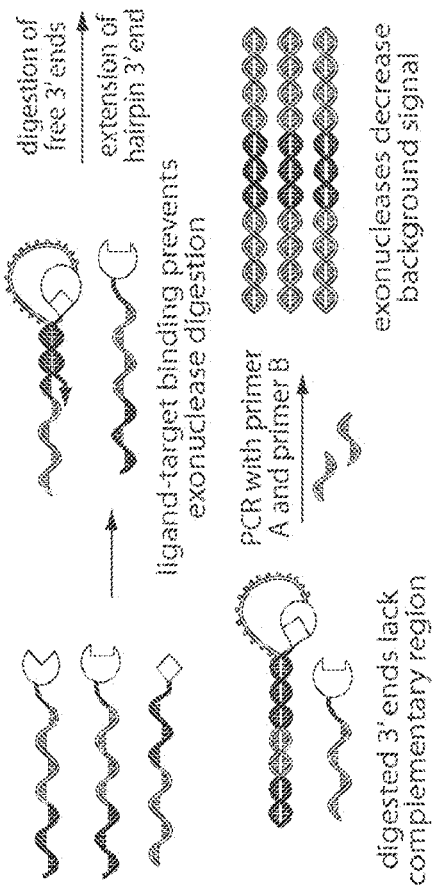

Some aspects of this disclosure relate to the discovery that the use of exonucleases before or during the primer extension step in ISID methods reduces the occurrence of false positives, thus reducing the background signal. As illustrated in FIG. 3, hybridized sequences resulting from ligand: target binding are polymerase substrates that can be extended into double-stranded PCR templates. In contrast, single-stranded sequences conjugated to unbound protein are substrates for 3' exonucleases. Digestion of their 3' ends removes the respective complementary regions, which avoids their contribution in primer extension and PCR procedures, thus reducing background signal.

Another improvement over previous technologies is that ISID can respond to the effect of affinity-modulating adaptor proteins or metabolites in cell lysates that would be absent in ligand screening or selection methods using a purified target, e.g., a purified protein target. The observation detection and analysis of ligand:target molecule interactions in the presence of such affinity-modulating agents is useful for identifying interactions of high relevance to in vivo settings, e.g., in the context of drug development. This capability of ISID is exemplified by the 100-fold amplification of DNA sequences encoding FRB:rapamycin or FKBP:rapamycin in samples overexpressing both FRB and FKBP (FRB•rapamycin:FKBP Kd=~100 fM; FKBP•rapamycin: FRB $K_d$=12 nM). In contrast, these sequences were amplified 10-fold less efficiently in samples overexpressing either FRB or FKBP alone (rapamycin:FKBP Kd=0.2 nM; rapamcyin:FRB $K_d$=26 µM).

Figure 4:
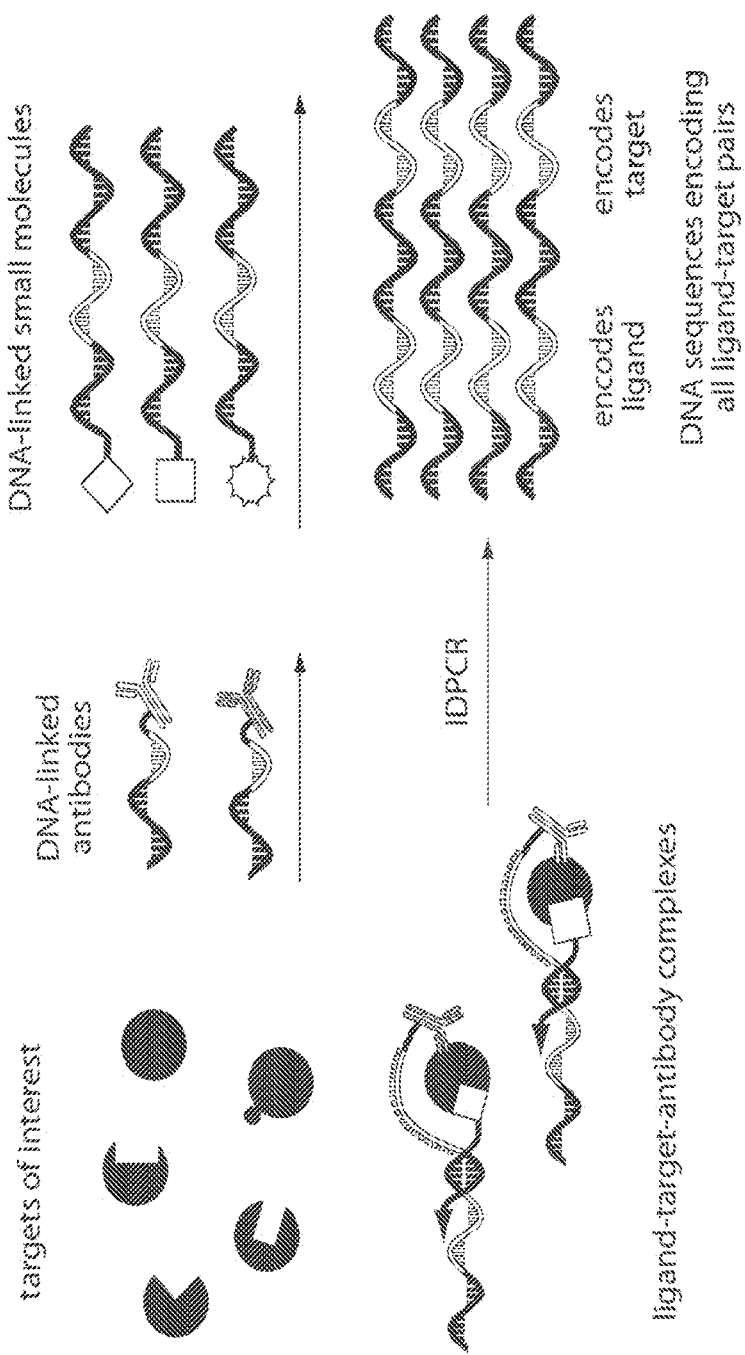
FIG. 4. Schematic of ISID for unmodified protein targets in complex samples.

While ISID can be performed with pre-labeled ligand and target molecules, ISID can also be extended to interaction screens in which only one or none of the binding partners has been linked to an identifying DNA beforehand. For example, ISID can be used to screen a mixture of unmodified protein targets for binding partners to a ligand of interest. FIG. 4 illustrates an exemplary scheme for such a screening approach, in which a plurality of small molecule ligands is linked to DNA tags and contacted with a mixture of unmodified target proteins. In order to link potential ligand-binding proteins to DNA-tags, DNA-linked antibodies against the respective proteins are employed. Upon ligand:protein binding, the antibody-linked nucleic acid tag hybridizes with the respective ligand-linked nucleic acid tag, resulting in an intramolecular hairpin that can be extended, amplified, and sequenced. One advantage of using ISID to screen unmodified protein targets for potential ligand-binding molecules is that such approaches allow an observation of ligand-binding behavior of the respective protein in its native state, e.g., in the presence of accessory proteins, substrates, and metabolites. Such approaches also allow for a direct comparison of target proteins that can bind to a specific ligand (or vice versa) in samples, e.g., in crude cell lysates, obtained from healthy and from diseased cells or tissues. The use of DNA-linked antibodies further allows for in situ ligand-binding assessment of membrane-bound proteins. In addition, DNA-linked antibodies avoid the requirement for recombinant technologies to generate and express tagged fusions of proteins of interest by making native, non-modified proteins directly accessible to DNA-linkage via antibody binding.

An illustration of how antibody ISID enriches ligands in crude cell lysates is provided in FIG. 5. Known ligands for various targets were spiked into crude HeLa cell lysates. Unmodified streptavidin and carbonic anhydrase were spiked into HeLa lysate at 0.01% w/w. ISID with a mock library of DNA-linked ligands and DNA-linked antibodies for the target proteins allowed good enrichment of their known ligands. For cases in which antibodies are not available or compete with ligand binding, protein affinity tags can be used as a handle for antibody-based IS ID.

Figure 6:
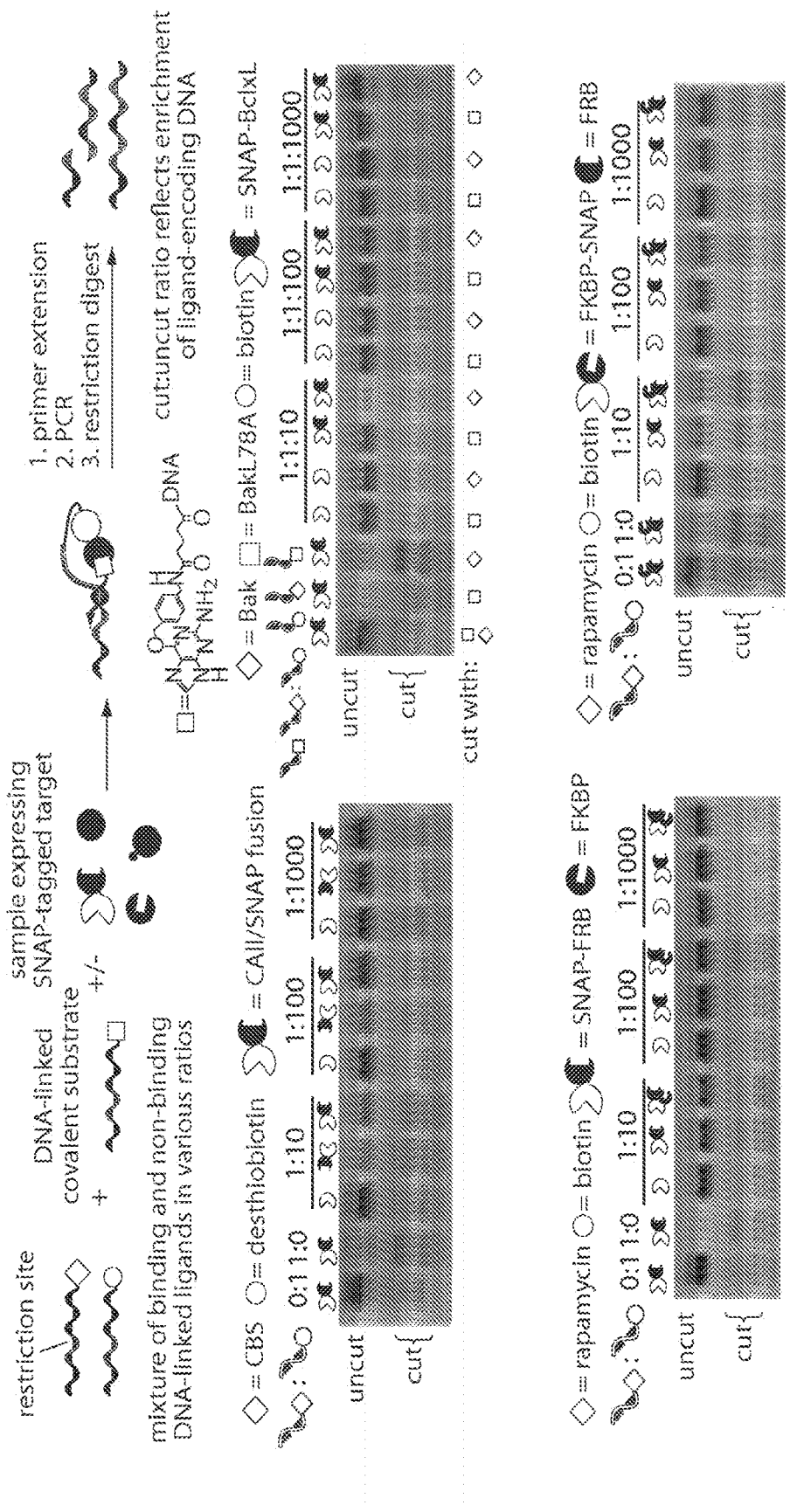
FIG. 6. ISID with self-labeling, e.g., SNAP-tagged, target proteins enables response to protein complex. The SNAP-tag reacts with O-benzylguanine derivatives, relaeasing guanine and covalently labeling itself with the rest of the substrate. The covalent bond between the SNAP-tagged protein and its DNA tag leads to several advantages for ISID, including increased sensitivity for low affinity ligands, and decreased dependence on target protein concentration since formation of a ternary complex is not required. Since the tag is also smaller than the antibody:epitope tag complex, it is also less likely to interfere with binding interactions between targets and their effector proteins.

In embodiments, where an antibody is not available to link a target molecule of interest to a nucleic acid, recombinant techniques can be used to express proteins or libraries of proteins that are fused to self-labeling tags. Such self-labeling tags typically comprise a reactive moiety that can form a covalent bond with specific reaction partners, e.g., reactive small molecules. Contacting a protein comprising a reactive tag with a nucleic acid conjugated to a suitable reactive moiety under appropriate conditions will result in the formation of a covalent bond between the reactive moiety and the reactive tag, thus linking the nucleic acid to the protein. FIG. 6 illustrates an exemplary embodiment of ISID with self-labeling target proteins. Here, the use of SNAP-tagged target proteins enables the detection and identification of ligand:protein complex formation. The SNAP-tag reacts with O-benzylguanine derivatives, releasing guanine and covalently labeling itself with the rest of the substrate. The covalent bond between the SNAP-tagged protein and its DNA tag can be employed in various ways to improve ISID sensitivity. For example, such self-labeling strategies can be used to increase sensitivity for low affinity ligands in complex samples, as only specific proteins are labeled. In addition, even low-abundance targets can be reliably detected, since the use of self-labeling protein tags decreases the dependence on target protein concentration, as formation of a ternary complex is not required. Typical self-labeling tags also have the advantage of being generally smaller than the antibody:epitope tag complex, and thus unlikely to interfere with binding interactions between targets and their effector proteins.

ISID thus enables the discovery of ligand:target pairs in unpurified samples, e.g., for targets that can be linked to nucleic acid tags via antibodies or for targets that can be expressed as fusions with reactive moieties such as self-labeling protein tags using nucleic acid-linked covalent tag substrates. Ligands can be provided either as nucleic acid-linked individual ligands or ligand libraries, or can be linked to nucleic acid sequences in situ as well via antibodies or reactive tags.

Methods for In-Situ Interaction Determination (ISID)

Some aspects of this disclosure provide methods for in situ interaction determination (ISID). In general, the ISID methods provided herein involve the identification of ligand:target interactions based on the formation of a ternary complex or a covalent bond between a polynucleotide-linked ligand (e.g., a small molecule ligand) and a polynucleotide-linked target molecule (e.g., a target protein) in situ. ISID is a versatile technology that can be adapted to various assay formats, including, but not limited to, single-ligand screening, ligand library screening, and ligand library×target library screening. For example, in some embodiments, the method involves providing a ligand associated with a nucleic acid molecule (e.g., a polynucleotide) and identifying molecules interacting with the ligand, e.g., molecules present in a cell lysate, a tissue, cell, biopsy, or environmental sample. In some embodiments, the method involves providing a plurality of polynucleotide-linked ligands, e.g., a library of polynucleotide-linked ligands, and identifying molecules interacting with the different ligands. In some embodiments, the method involves contacting a library of polynucleotide-linked ligands with a library of candidate target molecules and identifying ligand:target interactions in the resulting two-library mixture.

Typically, the ISID methods provided herein comprise contacting a ligand with a target molecule under conditions that are suitable for ligand:target interactions. The ligand and the target molecule are typically associated to a nucleic acid molecule that allows for the identification of ligand and target molecule in a ligand:target complex. The association of the target molecule with its corresponding oligonucleotide can be established either non-covalently, e.g., using a polynucleotide-linked binding agent (such as an antibody, see FIG. 7a), or covalently, e.g., using a reactive moiety (such as a self-labeling protein tag that reacts with a polynucleotide-linked small molecule, see FIG. 7b). In some embodiments, a ligand, such as a small molecule, may be synthesized with an attached nucleic acid molecule. In other embodiments, recombinant technologies may be used to generate a respective nucleic acid-associated ligand and/or target molecule. In yet other embodiments, the ligand and/or the target molecule may be conjugated with a nucleic acid tag in situ, e.g., using the labeling methods provided herein. Exemplary suitable methods for the generation of nucleic acid-associated ligands and target molecules are described herein, and additional suitable methods will be apparent to the skilled artisan based on this disclosure.

Ligand:target binding promotes hybridization of short complementary regions on the target- and ligand-linked nucleic acid tags (FIG. 7). A polymerase can then extend this hybridized region to generate a double-stranded product that contains sequences identifying both the target and its bound ligand. This extension product also contains two primer-binding sites and therefore can be amplified by PCR (FIG. 7).[3] By using antibodies or reactive protein tags, ISID avoids the requirement for purified protein targets, thus enabling ligand-binding screens to be performed on proteins that are free to undergo post-translational modification, interact with endogenous accessory proteins and metabolites, and access physiologically relevant conformational states.[5]

In some embodiments, the ISID methods provided herein comprise (i) providing a plurality of nucleic acid templates, wherein each nucleic acid template comprises a first primer hybridization site; a sequence tag; a second primer hybridization site; and a candidate ligand, wherein the candidate ligand of any specific nucleic acid template is identified by its sequence tag. In some embodiments, the ISID methods provided herein also comprise (ii) contacting the nucleic acid templates with a target molecule and with a first primer, wherein the first primer of step (ii) comprises a sequence complementary to the first primer hybridization site; a third primer hybridization site; and a binding moiety that binds to the target molecule, e.g., a target protein. In some embodiments, the ISID methods provide herein also comprise (iii) incubating the nucleic acid templates contacted with the target molecule and the first primer under conditions suitable for the candidate ligand and the binding moiety to bind to the target molecule. In some embodiments, the ISID methods provided herein also comprise (iv) incubating the nucleic acid templates contacted with the target molecule and the first primer under conditions suitable for the first primer bound to the nucleic acid template via a [candidate ligand]:[target molecule]:[binding moiety] interaction to hybridize with the first primer hybridization site of the nucleic acid template it is bound to for primer extension. In some embodiments, the ISID methods provided herein also comprise (v) contacting the nucleic acid templates contacted with the target molecule and the first primer with a PCR primer complementary to the second primer hybridization site and a PCR primer complementary to the third primer hybridization site, or a PCR primer complementary to the second and the third primer hybridization site. In some embodiments, the ISID methods provided herein also comprise (vi) performing a polymerase chain reaction (PCR) to amplify a nucleic acid template sequence tag identifying a candidate ligand able to bind to the target molecule.

In some embodiments, ISID is used to identify target molecules, e.g., target proteins, binding to a single ligand of interest, e.g., a single small molecule ligand. In such embodiments, it may not be necessary to link the ligand to a nucleic acid tag that identifies the ligand by a unique sequence, since only a single ligand is used. In some embodiments where a plurality of target molecules is screened in parallel, however, it will be necessary to link the respective target molecules to nucleic acid tags that comprise unique sequences identifying the respective target molecule. In some such embodiments, a single ligand is contacted with a plurality of potential target molecules in parallel, e.g., with at least 2, at least 3, at least 4, at least 5, at least 6, at least 7, at least 8, at least 9, at least 10, at least 15, at least 20, at least 30, at least 40, at least 50, at least 100, at least 200, at least 250, at least 300, at least 400, at least 500, at least 600, at least 700, at least 750, at least 800, at least 900, at least 1000, at least 2000, at least 2500, at least 3000, at least 4000, at least 5000, at least 6000, at least 7000, at least 7500, at least 8000, at least 9000, at least 10000, at least 20000, at least 25000, at least 50000, or at least 100000 potential target molecules.

In some embodiments, ISID is used to identify ligands that bind to a specific target molecule, e.g., a specific target protein of interest. In such embodiments, it may not be necessary to link the target molecule to a nucleic acid tag that identifies the target molecule by a unique sequence, since only a single target molecule is used. In some embodiments where a plurality of ligands molecules is screened in parallel, however, it will be necessary to link the respective ligands to nucleic acid tags that comprise unique sequences identifying the respective ligand. If the ligands are small molecules, they can be linked to sequence tags during or after synthesis. In some such embodiments, a single target molecule is contacted with a plurality of candidate ligands in parallel, e.g., with at least 2, at least 3, at least 4, at least 5, at least 6, at least 7, at least 8, at least 9, at least 10, at least 15, at least 20, at least 30, at least 40, at least 50, at least 100, at least 200, at least 250, at least 300, at least 400, at least 500, at least 600, at least 700, at least 750, at least 800, at least 900, at least 1000, at least 2000, at least 2500, at least 3000, at least 4000, at least 5000, at least 6000, at least 7000, at least 7500, at least 8000, at least 9000, at least 10000, at least 20000, at least 25000, at least 50000, or at least 100000 candidate ligands. In some embodiments, the target molecule is contacted with the plurality of ligands in a cell lysate or in otherwise physiological conditions that allow for the target molecule to maintain its native conformation, post-translational modification status (if any), and/or that allow the target molecule to interact with or bind to any accessory binding partners, e.g., accessory proteins, substrates or metabolites that may be present in its native environment.

In some embodiments, ISID is used to screen a library of candidate ligands against a library of target molecules. In such embodiments, it is typically necessary to link both the candidate ligands and the target molecule to nucleic acid tags that identify the respective ligand and target molecule in any given ligand:target complex. In some such "library× library" embodiments, a library of candidate ligands comprising at least 2, at least 3, at least 4, at least 5, at least 6, at least 7, at least 8, at least 9, at least 10, at least 15, at least 20, at least 30, at least 40, at least 50, at least 100, at least 200, at least 250, at least 300, at least 400, at least 500, at least 600, at least 700, at least 750, at least 800, at least 900, at least 1000, at least 2000, at least 2500, at least 3000, at least 4000, at least 5000, at least 6000, at least 7000, at least 7500, at least 8000, at least 9000, at least 10000, at least 20000, at least 25000, at least 50000, or at least 100000 candidate ligands, is contacted with a library of target molecules comprising at least 2, at least 3, at least 4, at least 5, at least 6, at least 7, at least 8, at least 9, at least 10, at least 15, at least 20, at least 30, at least 40, at least 50, at least 100, at least 200, at least 250, at least 300, at least 400, at least 500, at least 600, at least 700, at least 750, at least 800, at least 900, at least 1000, at least 2000, at least 2500, at least 3000, at least 4000, at least 5000, at least 6000, at least 7000, at least 7500, at least 8000, at least 9000, at least 10000, at least 20000, at least 25000, at least 50000, or at least 100000 target molecules. In some embodiments, the candidate ligands are small molecules. In some embodiments, the target molecules are proteins. In some embodiments, the target molecules are expressed in a cell. In some embodiments, the contacting of the target molecules with the ligands is carried out without purification of the target molecules, e.g., in a crude cell lysate. In some embodiments, the library of target molecules is contacted with the library of ligands in a cell lysate or in otherwise physiological conditions that allow for the target molecules to maintain their native conformation, post-translational modification status (if any), and/or that allow the target molecules to interact with or bind to any accessory binding partners, e.g., accessory proteins, substrates or metabolites that may be present in their native environment.

In some embodiments, the target molecule of (ii) is contacted with the nucleic acid templates of (i) in the presence of accessory molecules and metabolites that are present in a cell expressing the target molecule. This may, for example, be achieved by contacting the target molecule in a crude cell lysate. For example, the target molecule may be natively or recombinantly expressed in a cell and a crude lysate of the expressing cell(s) may be used to contact the target molecule with a ligand. As explained elsewhere herein, contacting target molecules in a cell lysate has the advantage that the conditions in the lysate closely resemble the environment of the target molecule in its native state. A lysate of cells that natively express a target molecule will most closely resemble the native state of such a target molecule. The native state includes native conformation status, native configuration of post-translational modifications, native tendency to dimerize or multimerize, and the presence of interaction partners, such as accessory proteins, substrates, and metabolites that are present in the target molecule's native environment. In situ interaction screening under conditions that closely resemble the native environment of a target molecule yields results of high relevance to in vivo applications. In situ interaction screening is thus particular useful in the context of drug development, where the binding of a ligand drug to its intended target may be modulated or inhibited by factors such as the target's conformation, post-translational modifications, di- or multimerization status, and the presence of competing or modulating interaction partners.

In the context of this disclosure, a native state or environment, e.g., of a target protein, refers to a natural state or environment, for example, a state or environment that the target protein can be observed in without human intervention. Such a native state or environment would thus include cells that express or comprise the respective target protein naturally, e.g., without the use of recombinant technologies or other treatment of the cells. For example, a native state of an oncogenic target protein may be observed in cells that naturally express the protein, whether malignant or not, which would include naturally-occurring tumor cells expressing the oncogene. In the case of secreted target molecules, or of molecules that are in contact with the intercellular space, such as receptor molecules on the surface of cells, a native state or environment may include conditions typically present in the space they are secreted into or that they are in contact with. Typically, a cell lysate, a tissue or cell sample, a biopsy, or an environmental sample, will provide a native environment for a target molecule comprised therein, particularly, if the lysate, sample, or biopsy is not excessively processed before the target molecule is contacted with a candidate ligand. In this context, unprocessed or minimally processed samples are preferred to more extensively processed samples, as each additional processing step may remove a sample further from its original, or native, state, which may in turn affect the status or the binding characteristics of a given target molecule comprised within a sample.

In this context, an unprocessed sample refers to a sample that has not undergone any purification procedures. A crude cell lysate, obtained by isolating cells expressing or comprising a target molecule, disrupting the integrity of the cell membranes and, optionally, homogenizing the resulting lysate, is considered an unprocessed or minimally processed sample for purposes of this disclosure. Minimal processing refers to processing steps that do not significantly alter the physiological environment or the binding characteristics of a target protein in a given sample. Minimal processing steps include, for example, the homogenization of samples, the clarification of samples from insoluble matter, such as inorganic matter or cells and cell wall fragments, the freezing and thawing of samples. While unprocessed or minimally processed samples are preferred in certain ISID embodiments, it will be understood that the disclosure is not limited to such embodiments, and that ISID technology can also be applied to more extensively processed samples, such as partially purified or purified target molecules.

In some embodiments, the target molecule is a protein. In some embodiments, the target molecule is a human protein. In some embodiments, the protein is a therapeutically important protein, e.g., a protein that is associate with a disease or disorder or a protein the functional modulation of which is associated with an improvement or a worsening of a pathological state in a subject. In some embodiments, the protein is a potential target for a therapeutic intervention, e.g., an identified or validated drug target.

In some embodiments, the target protein comprises a post-translational modification. Such a post-translational modification may include one or more of the following: phosphorylation, acetylation, glycosylation (e.g., N-linked glycosylation, C-linked glycosylation, or O-linked glycosylation), amidation, methylation, hydroxylation, ubiquitylation, pyrrolidone carboxylic acid modifications, sulfation, sumoylation, gamma-carboxyglutamic acid modification, palmitoylation, myristoylation, ADP-ribosylation, citrullination, farnesylation, S-nitrosylation, geranyl-geranylation, deamidation, formylation, nitration, GPI anchoring, and bromination. Additional post-translational modifications will be apparent to those of skill in the art.

In some embodiments, the target molecule is conjugated to a nucleic acid tag via non-covalent interaction. For example, in some embodiments, the binding moiety of the first primer binds to the target molecule via a non-covalent interaction. In some embodiments, the target molecule comprises a binding agent, such as an affinity tag, and the binding moiety binds to the binding agent of the target molecule. The term "binding agent", as used herein, refers to an agent that interacts with a binding partner to form a non-covalent bond. Examples of suitable binding agents that may be attached to target molecules are affinity tags, heterologous epitopes, aptamers, and adnectins.

In embodiments, where the target is a protein and comprises an affinity tag, the target is typically expressed as a fusion with the respective affinity tag from a recombinant expression construct. Suitable affinity tags and moieties binding to affinity tags are well known to those of skill in the art and include, for example, AviTags (allowing biotinylation by the enzyme BirA and binding to streptavidin moieties (GLNDIFEAQKIEWHE, SEQ ID NO: 1)); calmodulin-tags (bound by calmodulin (KRRWKKNFIAVSAANRFKKISSSGAL, SEQ ID NO:2)); FLAG-tags (recognized by antiFLAG antibodies (DYKDDDDK, SEQ ID NO: 3)); HA-tag, (recognized by anti-HA antibodies (YPYDVPDYA, SEQ ID NO: 4)); Myc-tag (recognized by anti-Myc antibodies (EQKLISEEDL, SEQ ID NO: 5)); S-tags (KETAAAKFERQHMDS, SEQ ID NO: 6); SBP-tags (bind to streptavidin (MDEKTTGWRGGHVVEGLAGELEQLRARLEHHPQGQREP, SEQ ID NO: 7)); Softags (e.g., Softag 1 (SLAELLNAGLGGS, SEQ ID NO: 8) or Softag 3 (TQDPSRVG, SEQ ID NO: 76)); Strep-tags (bind to streptavidin or streptactin (e.g., Strep-tag II: WSHPQFEK, SEQ ID NO: 9)); and V5 tags (recognized by anti-V5 antibodies (GKPIPNPLLGLDST, SEQ ID NO: 10). Additional suitable affinity tags will be apparent to those of skill in the art based on the instant disclosure.

In some embodiments, the binding moiety of the first primer comprises an antibody or an antigen-binding antibody fragment. The term "antibody," as used herein, refers to an immunoglobulin, whether natural or wholly or partially synthetically produced. All derivatives thereof which maintain specific binding ability are also included in the term. The term also covers any protein having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. Derivatives of the IgG class, however, are preferred in the present invention.

The term "antibody fragment," as used herein, refers to any derivative of an antibody which is less than full-length. Preferably, the antibody fragment retains at least a significant portion of the full-length antibody's specific binding ability. Examples of antibody fragments include, but are not limited to, Fab, Fab', F(ab')$_2$, scFv, Fv, dsFv, diabody, and Fd fragments. The antibody fragment may be produced by any means. For instance, the antibody fragment may be enzymatically or chemically produced by fragmentation of an intact antibody or it may be recombinantly produced from a gene encoding the partial antibody sequence. Alternatively, the antibody fragment may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

Single-chain Fvs (scFvs) are recombinant antibody fragments consisting of only the variable light chain (VL) and variable heavy chain (VH) covalently connected to one another by a polypeptide linker. Either VL or VH may be the NH2-terminal domain. The polypeptide linker may be of variable length and composition so long as the two variable domains are bridged without serious steric interference. Typically, the linkers are comprised primarily of stretches of glycine and serine residues with some glutamic acid or lysine residues interspersed for solubility.

Diabodies are dimeric scFvs. The components of diabodies typically have shorter peptide linkers than most scFvs, and they show a preference for associating as dimers.

An Fv fragment is an antibody fragment which consists of one VH and one VL domain held together by noncovalent interactions. The term dsFv is used herein to refer to an Fv with an engineered intermolecular disulfide bond to stabilize the VH-VL pair.

A F(ab')$_2$ fragment is an antibody fragment essentially equivalent to that obtained from immunoglobulins (typically IgG) by digestion with an enzyme, e.g., with ficin or pepsin. The fragment may be recombinantly produced.

A Fab fragment is an antibody fragment essentially equivalent to that obtained by reduction of the disulfide bridge or bridges joining the two heavy chain pieces in the F(ab')2 fragment. The Fab' fragment may be obtained by digestion of antibodies, e.g., with ficin or papain in the presence of a reducing agent, or may be recombinantly produced. The heavy chain segment of the Fab fragment is also referred to as the Fd fragment.

The first primer may be conjugated to an antibody or an antibody fragment by any suitable method. Some exemplary methods of conjugation are described in detail herein, and additional suitable methods will be apparent to the skilled artisan based on this disclosure. In some embodiments, the strategy to link a nucleic acid molecule, e.g., a DNA primer, to an antibody is analogous to a strategy that is suitable to covalently link a nucleic acid, e.g., DNA, to other proteins, e.g., to target proteins. For example, a nucleic acid molecule (e.g., a DNA molecule) modified with a 5' carboxylate may be activated using EDC/sNHS, purified, e.g., by gel filtration using a G-25 spin column, and incubated overnight with an antibody. The resulting nucleic acid:antibody conjugate can then be separated from unreacted nucleic acid molecules by centrifugation in a spin column with MWCO 100,000 or by any other suitable method. In some embodiments, the antibody may be a commercially available antibody. In some embodiments, the antibody may first be purified, e.g., to remove any sodium azide from the storage solution. This may be achieved by dialysis against a suitable buffer, e.g., PBS. The purified antibody may then be concentrated, e.g., by using a spin column with MWCO 100,000.

In some embodiments, the binding moiety of the first primer comprises a ligand or a receptor domain. The use of ligand or receptor domains is particularly useful if the target molecule is known or suspected to have some binding affinity to the ligand or receptor domain. For example, if the target molecule is known to bind to a specific receptor in vivo or in vitro, ISID may be used to identify the specific receptor domain mediating the binding under native conditions, or to elucidate minimal binding requirements or pathological disruptions of target:receptor interactions by employing mutated receptor domains. ISID can thus also be used to model the mechanics of target:ligand interactions in the context of mutations known to cause diseases or disorders, e.g., mutations in receptor domains or in ligand domains that are associated with pathological states.

In some embodiments, the binding moiety of the first primer covalently binds the target molecule. This covalent binding typically involves a chemical reaction between the binding moiety and a reactive moiety of the target molecule that results in the formation of a covalent bond. For example, in some embodiments, the target molecule comprises a reactive tag, such as a self-labeling protein tag. In some embodiments, the binding moiety of the first primer reacts with the reactive tag of the target molecule, thus covalently binding the first primer to the target molecule. In some embodiments, the reactive tag is a self-labeling protein tag. Suitable self-labeling protein tags are well known to those of skill in the art and exemplary suitable self-labeling tags include SNAP-tags, CLIP-tags, and Halo-tags.

Self-labeling protein tags allow for highly specific covalent labeling of proteins under physiological conditions. Self-labeling tags typically comprise a reactive moiety that reacts with a small compound to form a covalent bond. In some embodiments, a target molecule, e.g., a target protein, is expressed as a fusion with a self-labeling tag and contacted with a first primer conjugated to a reactive moiety. The reaction of self-labeling tag and reactive moiety of the first primer results in the formation of a covalent bond between the primer and the protein, and thus the formation of a primer-linked target protein.

In the SNAP-tag, CLIP-tag, and Halo-tag systems, the target protein is expressed as a fusion with the respective tag, and the fusion protein is conjugated to the first primer labeled by a self-labeling tag based on the DNA repair protein O6-alkylguanine-DNA-alkyltrasferase(SNAP and CLIP tags) or a modified haloalkane dehalogenase (Halo tag). Labeling strategies, methods, and reagents for the use of these and other self-labeling tags are well known to those of skill in the art and include, without limitation, those described in Hinner et al., (2010) How to obtain labeled proteins and what to do with them. Curr Opin Biotechnol 21: 766-776; Keppler et al., (2003) A general method for the covalent labeling of fusion proteins with small molecules in vivo. Nat Biotechnol 21: 86-89; and Gautier et al., (2008) An engineered protein tag for multiprotein labeling in living cells. Chem Biol 15: 128-136; the entire contents of each of which are incorporated herein by reference.

Additional suitable strategies for covalently attaching a first primer to a target molecule will be apparent to those of skill in the art. Such additional strategies may, for example, and without limitation, include the use of click chemistry handles conjugated to the first primer and the target molecule, or the use of additional tags, such as ACP-tags or MCP-tags to conjugate the first primer to the target molecule. ACP-tags and MCP-tags can be used to effect covalent post-translational conjugation via modification by a phosphopantetheinyl transferase. Additional suitable strategies for conjugating the first primer to a target molecule may include, in some embodiments, the use of intein-mediated protein ligation or of expressed protein ligation. The IPL reaction allows the ligation of a synthetic peptide or a protein with an N-terminal cysteine residue to the thioester on the C-terminus of a polypeptide through a native peptide bond. See, e.g., Evans et al., (1998) Protein Sci. 7, 2256-2264; and Muir et al. (1998) Proc. Natl. Acad. Sci. USA 95, 6705-6710; the entire contents of each of which are incorporated herein by reference. In such embodiments, the first primer could be synthesized or generated to be conjugated to an appropriate peptide that can serve as a substrate for intein-mediated protein ligation.

In some embodiments, the method further comprises contacting the nucleic acid templates of the library contacted with the target molecule and the first primer with a 3'-exonuclease. The term 3'-exonuclease refers to any enzyme that exhibits 3'4→5'-exonuclease activity. As explained in more detail elsewhere herein, the use of a 3'-exonuclease may result in the digest of unpaired complementary region sequences, e.g., sequences of nucleic acid tags that are linked to ligands or target molecules that have not found a binding partner in and ISID experiment. These sequences identifying unbound molecules are of no interest for identifying binding partners, but may interfere with the amplification of sequences from bound molecules and produce false positive reads. Accordingly, the use of a 3'-exonuclease is particularly useful in embodiments, where a reduction of false positive reads is desirable, which is typically the case when complex samples such as crude cell lysates are employed.

In some embodiments, the contacting with the 3'-exonuclease is effected before or simultaneously with primer extension. For example, exposure to 3'-exonuclease may conveniently be achieved by using a DNA polymerase for primer extension that exhibits 3'-exonuclease activity. For example, the Klenow fragment of DNA Polymerase I of *E. coli* exhibits 3'-exonuclease activity (but not the 5'-exonuclease activity of the DNA Pol I holoenzyme), making it a suitable DNA polymerase for primer extension. For example, in some embodiments, a nucleic acid template conjugated to a ligand and contacted with the target molecule and the first primer is contacted with Klenow fragment of DNA polymerase I under conditions suitable for primer extension and for the Klenow fragment to exhibit its 3'-exonuclease activity. If a polymerase is used for primer extension that does not exhibit 3'-exonuclease activity, the respective sample may be treated with an enzyme or enzyme domain exhibiting 3'-exonuclease activity but no primer extension activity. Suitable polymerases and 3'-exonuclease domains and enzymes, e.g., mutants of DNA polymerase I having no exonuclease activity or having only 3'-exonuclease but no polymerase activity are well known to those of skill in the art, and additional suitable enzymes and enzyme domains will be apparent to the skilled artisan based on the instant disclosure.

Primer extension of the paired duplex nucleic acid molecules that formed a hairpin upon target:ligand interaction results in the generation of a double-stranded nucleic acid construct that comprises sequence tags identifying the respective ligand and target. These identifying sequences can be amplified by PCR. In embodiments, where a plurality of ligand:target pairs is evaluated or screened for, the various nucleic acid molecules (e.g., the nucleic acid template conjugated to the ligand and the first primer conjugated to the target) may comprise universal PCR primer binding sites, so that all sequences stemming from ligand:target pairs can be amplified in a single PCR reaction with a single primer or primer pair.

ISID methods may also comprise identifying the ligand or the target or both of a given target:ligand complex by determining the sequence of the respective sequence tag(s), e.g., the sequence tag that identifies the ligand and/or the sequence tag that identifies the target molecule. Determining the sequence of a sequence tag typically involves sequencing a PCR amplicon comprising the sequence tag. In ISID applications, where a plurality of ligand:target interactions are evaluated, a heterogeneous population of PCR amplicons will be generated that can either be isolated and sequenced separately, or that can be sequences in parallel by using parallel sequencing techniques. Suitable sequencing techniques are well known to those of skill in the art and the disclosure is not limited in this respect.

A variety of sequence configurations may be used for the nucleic acid templates and primers employed in ISID methods. For example, in some embodiments, the first primer hybridization site is between about 5 and about 16 nucleotides long. The skilled artisan will understand that, in some embodiments, the first primer hybridization site should be designed to exhibit a $T_m$ that allows efficient intramolecular priming under the specific reaction conditions employed, but does not allow efficient intermolecular priming under those conditions. Strategies and methods for designing primer sites to suit these criteria are well known to those of skill in the art. For example, in some embodiments, the first primer hybridization site is 5, 6, 7, 8, 9, or 10 nucleotides long.

In some embodiments, the second and the third primer hybridization site are the same nucleic acid sequence, which allows PCR amplification of sequence tags with a single primer. Accordingly, in some embodiments, the PCR primer complementary to the second primer hybridization site and the PCR primer complementary to the third primer hybridization site are the same nucleic acid sequence. In some embodiments, the second and the third primer hybridization site are different nucleic acid sequences. In such embodiments, a pair of different PCR primers will be required for PCR amplification. In some embodiments, the first primer hybridization site and the third primer hybridization site overlap or are identical. In some embodiments, the sequence tag, e.g., the sequence identifying the ligand or the target molecule, is about 5 to about 30 nucleotides long.

In some embodiments, the candidate ligand is selected from the group consisting of a peptides, nucleic acids, and small organic compounds. In some embodiments, the target molecule is selected from the group consisting of proteins, receptors, receptor ligands, nucleic acids, enzyme substrates, metabolites, and signaling molecules. In some embodiments, the target molecule is a human protein. In some embodiments, the target molecule is a protein associate with a disease or disorder. In some embodiments, the target molecule is associated with a pathological state in a human subject.

In some embodiments, the binding between the candidate ligand and the target molecule is characterized by a $K_D<10^{-5}$, $K_D<10^{-6}$, a $K_D<10^{-7}$, a $K_D<10^{-8}$, a $K_D<10^{-9}$, a $K_D<10^{-10}$, a $K_D<10^{-11}$, or a $K_D<10^{-12}$. As explained in more detail elsewhere herein, ISID technology can be used to detect ligand:target interactions of various affinities, e.g., of an affinity characterized by a $K_D<10^{-5}$, a $K_D<10^{-6}$, a $K_D<10^{-7}$, a $K_D<10^{-8}$, a $K_D<10^{-9}$, a $K_D<10^{-10}$, a $K_D<10^{-11}$, or a $K_D<10^{-12}$.

In some embodiments, the conditions suitable for hybridization of the nucleic acid sequence complementary to the first primer hybridization site to the first primer hybridization site and primer extension are conditions not allowing for efficient primer site hybridization and primer extension of first primer not connected to a nucleic acid template by a candidate ligand:target molecule interaction characterized by a $K_D<10^{-6}$, a $K_D<10^{-7}$, a $K_D<10^{-8}$, a $K_D<10^{-9}$, a $K_D<10^{10}$, a $K_D<10^{-11}$, or a $K_D<10^{-12}$.

Suitable PCR methods, reagents, and primers will be apparent to those of skill in the art based on this disclosure. In some embodiments, the PCR is quantitative, real-time PCR. In some embodiments, the PCR is semi-quantitative endpoint PCR. In some embodiments, the PCR comprises 15-32 cycles, wherein each cycle comprises: a denaturation step of 0.1-20 minutes incubation at 85-110° C.; an annealing step of 0.1-20 minutes incubation at 37-78° C.; and an elongation step of 0.1-20 minutes incubation at 62-85° C. In some embodiments, the PCR comprises 15-32 cycles, wherein each cycle comprises a denaturation step of 0.5 minutes incubation at 95° C.; an annealing step of 0.5 minutes incubation at 58° C.; and an elongation step of 0.5 minutes incubation at 72° C. It will be apparent to the skilled artisan that PCR conditions will depend on the specific primer design, length of amplicon, and polymerase employed. Exemplary suitable methods and strategies are described herein and additional suitable methods will be apparent to the skilled artisan. The disclosure is not limited in this respect.

Kits

Some aspects of this disclosure provide kits for in situ interaction determination (ISID). The kits provided herein are typically housed in container in which the components of the kit are packaged. In addition to the listed kit components, the kits will typically also comprise instructions for use of the included components. In some embodiments, the kit comprises (i) a first primer, comprising a sequence complementary to a first primer hybridization site of a nucleic acid template; a second primer hybridization site, and a binding moiety; (ii) a second primer complementary to the second primer hybridization site; and (iii) a third primer complementary to a third priming site of the nucleic acid template. In some embodiments, the binding moiety comprises a ligand, an antibody or antibody fragment, or a reactive moiety. In some embodiments, the reactive moiety reacts with a self-labeling tag to form a covalent bond between the first primer and the tag. In some embodiments, the kit further comprises (iv) a 3' exonuclease, for example, a DNA polymerase having 3'-exonuclease activity. In some embodiments, the kit further comprises a PCR buffer; a nucleotide mix; and/or a thermophilic polymerase.

Some of the embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

EXAMPLES

Materials and Methods

Unless otherwise noted, chemical reagents were purchased from Sigma-Aldrich. Water was purified with a Milli-Q purification system. Modified DNA oligonucleotides were synthesized on a PerSeptive Biosystems Expedite 8909 DNA synthesizer. Standard DNA oligonucleotides were purchased from Integrated DNA Technologies. All reagents and phosphoramidites for DNA synthesis were purchased from Glen Research. All oligonucleotides were synthesized and deprotected according to manufacturer's protocols. Oligonucleotides were purified by reverse-phase high-pressure liquid chromatography (HPLC, Agilent 1200) using a C18 stationary phase (Eclipse-XDB C18, 5 µm, 9.4×200 mm) and an acetonitrile/100 mM triethylammonium acetate gradient. Oligonucleotide concentrations were quantitated by UV spectroscopy using a Nanodrop ND1000 spectrophotometer. Non-commercial oligonucleotides were characterized by LC/ESI-MS; reverse-phase separation was performed on an Alliance 2695 (Waters) HPLC system using a UPLC BEH C18 column (1.7 µm, 2.1×50 mm) stationary phase and 6 mM aqueous triethylammonium bicarbonate/MeOH mobile phase interfaced to a Q-Tof Micro mass spectrometer (Waters). Alternately, modified oligonucleotides were characterized using an equivalent column and mobile phase interfaced with a Waters Acquity ultra-performance LC (UPLC) quadrupole TOF Premier instrument.

Synthesis of C40-azidohexanyl-rapamycin

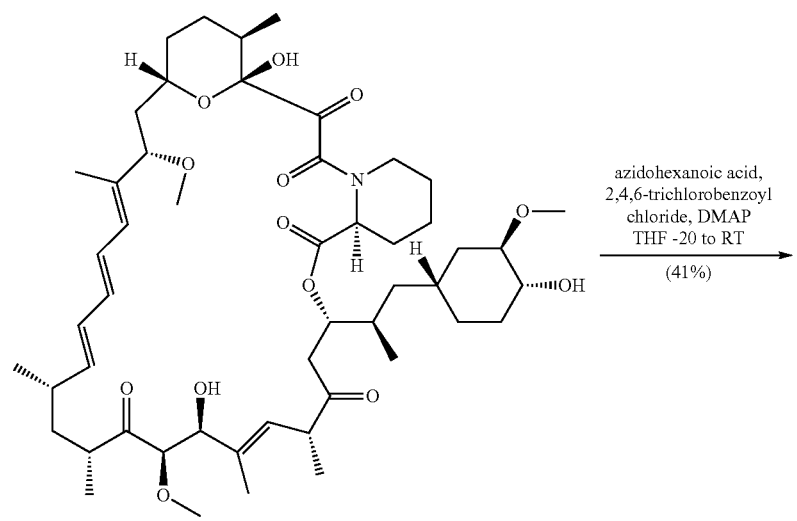

azidohexanoic acid,
2,4,6-trichlorobenzoyl
chloride, DMAP
THF -20 to RT (41%)

-continued

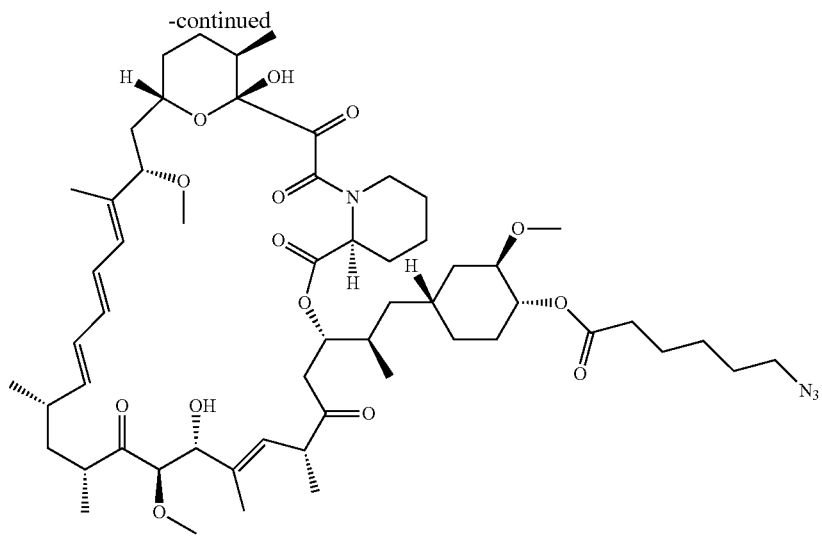

To an oven dried, sealed, 2-dram vial was added 700 μL dry THF and 20 μL azidohexanoic acid. The solution was cooled to −18° C. for 10 min before the addition of 25 μL dry triethylamine and 22 μL 2,4,6-trichlorobenzoyl chloride. The resulting mixture was stirred at −18° C. for 80 min. Rapamycin (LC Labs) (127.8 μmol) and DMAP (168 μmol) were dissolved in 600 μL dry THF and were added dropwise. The reaction was warmed to room temperature and stirred for 3 hours before diluting with 1 mL saturated sodium bicarbonate. The reaction mixture was then extracted with ethyl acetate three times. The combined organic layers were washed with brine, dried over sodium sulfate, concentrated, and directly subjected to silica gel chromatography (3:2 hexanes/ethyl acetate). TLC $R_f$=0.3 (3:2 ethyl acetate:hexanes). $^1$H NMR (CDCl$_3$, 400 MHz): δ 6.35 (m, 2H), 6.14 (dd, 1H, J=9.9 Hz, 15 Hz), 5.96 (d, 1H, J=10.4 Hz), 5.54 (dd, 1H, J=8.8 Hz, 15 Hz), 5.4 (d, 1H, J=10 Hz), 5.28 (d, 1H, J=5 Hz), 5.16 (dd, 1H, J=6 Hz, 10.4 Hz), 4.66 (m, 1H), 4.17 (d, 1H, J=5.2 Hz), 3.85 (m, 1H), 3.72 (d, 1H, J=5.9 Hz), 3.66 (m, 1H), 3.57 (d, 1H, J=12.5 Hz), 3.37 (s, 1H), 3.36 (s, 3H), 3.33 (s, 1H), 3.32 (s, 3H), 3.25 (m, 3H), 3.16 (m, 1H), 3.14 (s, 3H), 2.72 (m, 1H), 2.68 (d, 1H, J=5.5 Hz), 2.57 (dd, 1H, J=6.5 Hz, 16.9 Hz), 2.29-2.35 (m, 4H), 2.10 (d, 1H, J=11.7 Hz), 2.04 (s, 1H), 1.98 (m, 3H), 1.83 (m, 1H), 1.80 (m, 1H), 1.74 (m, 3H), 1.70-1.20 (m, 23H), 1.14 (d, 1H, J=6.7 Hz), 1.10 (d, 3H, J=6.7 Hz), 1.05 (d, 3H, J=6.5 Hz), 0.98 (d, 3H, J=6.5 Hz), 0.95 (d, 3H, J=6.6 Hz), 0.91 (d, 3H, J=6.8 Hz), 0.82 (m, 1H). LCMS expected (M+OH) 1069.64, observed 1069.4.

Synthesis of Ligand-DNA Conjugates by Amine Acylation

To 215 μL DMSO was added 1.25 μmol of a carboxylate-containing small molecule (biotin, desthiobiotin, iminobiotin, 4-carboxy benzene sulfonamide (CBS), and Gly-Leu-CBS (GLCBS)[4] (100 mM in DMSO), 3.3 μmol N-hydroxysulfosuccinimide (sNHS) (333 mM in 2:1 DMSO:water), 1.2 μmol 1-ethyl-3-[3-dimethylaminopropyl]carbodiimide (EDC) (100 mM in anhydrous DMSO). This mixture was stirred at room temperature for 30 min before addition of 5-10 nmol 3'-amine-modified DNA, and 50 μL 500 mM TEA/HCl, pH 10. The resulting mixture was stirred 8-16 hours before the DNA was recovered by ethanol precipitation and purified by reverse phase HPLC.

Synthesis of Peptide-DNA Conjugates (Bad, Bak, BakL78A)

To 22.2 μL water was added 10 nmol 3'-dithiol modified DNA (17.8 μL in water), 5 μL of 500 mM HEPES pH 8, and 5 μL of 1M dithiothreitol (DTT in water). The mixture was incubated at room temperature for 30 min. 3'-thiol-modified DNA was purified by size exclusion with an illustra MicroSpin G-25 column (GE Healthcare) and eluted in 50 μL water.

To the reduced 3'-thiol-modified DNA was added 14.2 μL 10×PBS, 7 μL of 50 mM EDTA, 150 nmol of Bad BH3 peptide (103-127), Bak BH3 peptide (72-87), or BakL78A (72-87) peptide (Anaspec) (15 μL in water), and 75 nmol SM(PEG)$_2$ (Pierce) (0.75 μL in DMSO). The mixture was incubated overnight at room temperature before the DNA was recovered by ethanol precipitation. The resulting peptide-DNA conjugate was purified by reverse phase HPLC.

Synthesis of 3'-Propargyl-Modified DNA

To 90 μL DMSO was added 33 nmol 3'-amine-modified DNA (125 μL in water), 4 μmol propargyl-NHS (Click Chemistry Tools) (40 μL in DMSO), and 50 μL of 500 mM TEA/HCl pH 10. The reaction was stirred overnight prior to ethanol precipitation and reverse phase HPLC purification of the resulting propargyl-modified DNA.

Synthesis of Rapamycin-DNA Conjugate Using a Cu(I)-Promoted Azide-Alkyne Cycloaddition To 200 μL DMSO was added 6 nmol 3'-propargyl-modified DNA (25 μL in water), 20 μL of 100 mM sodium phosphate buffer pH 7.5, 500 nmol C-40-rapamycin-hexylazide (5.7 μL in DMSO), and 200 nmol 1:3 Cu-TBTA (80 μL in 1:3 water:DMSO). Nitrogen was bubbled through the resulting solution for 10 min prior to the addition of 1 mmol triscarboxyethylphosphine (TCEP) (2 μL in water). The reaction was sealed with parafilm and stirred overnight prior to DNA recovery by ethanol precipitation and purification of the rapamycin-DNA conjugate by reverse phase HPLC.

Synthesis of Benzylguanine-Modified DNA.

To 200 µL DMSO was added 1.25 µmol BG-GLA-NHS (New England Biolabs) (12.5 µL in DMSO), 10 nmol 3'-amine-modified DNA (64 µL in water), 50 µL of 500 mM Triethylamine/HCl pH 10. The mixture was stirred at room temperature overnight before ethanol precipitation of DNA and purification of the DNA-BG conjugate by reverse phase HPLC.

TABLE 1

List of modified DNA oligonucleotides, expected and observed masses, and their sequences.
Oligonucleotide Sequences and LC/MS Characterization

| name | expected mass (Da) | observed mass (Da) | sequence | SEQ ID NO: |
|---|---|---|---|---|
| 1a | 10590.05 | 10588.0 | (5'carboxy)(sp18)CGGCGATCGTGAAGGAGGCTAGCCTGAGTG AG | 11 |
| 2a-amine | 13718.96 (+DMT) | 13720.4 | TGGATCGTGATGACTGTCCCGACAAGCATACGTATCTCACT (sp18)(sp18)(3'aminoC6) | 12 |
| 2a-GLCBS | 13771.9 | 13770.1 | TGGATCGTGATGACTGTCCCGACAAGCATACGTATCTCACT (sp18)(sp18)(3'aminoC6)(GLCBS) | 13 |
| 2b-biotin | 13833.41 | 13831.4 | TGGATCGTGATGACTGTCCCGACAAGCATACGTATCTCACT (sp18)(sp18)(3'biotinTEG) | 14 |
| 2b-desthiobiotin | 14103.36 (+DMT) | 14102.0 | TGGATCGTGATGACTGTCCCGACAAGCATACGTATCTCACT (sp18)(sp18)(3'desthiobiotinTEG) | 15 |
| 2c-GLCBS | 13796.95 | 13795.2 | TGGATCGTGATGACTGTCCCGACAAGGATCCGTATCTCACT (sp18)(sp18)(3'aminoC6)(GLCBS) | 16 |
| 2d-amine | 13443.95 | 13441.7 | TGGATCGTGATGACTGTCCCGACAACCATGGGTATCTCACT (sp18)(sp18)(3'aminoC6) | 17 |
| 2d-desthiobiotin | 13640.2 | 13636.0 | TGGATCGTGATGACTGTCCCGACAACCATGGGTATCTCACT (sp18)(sp18)(3'aminoC6)(desthiobiotin | 18 |
| 2e | 13363.9-13524.0 | 13441.7 (spread) | TGGATCGTGATGACTGTCCCGACAATNNNNAGTATCTCACT (sp18)(sp18)(3'aminoC6) | 19 |
| 2a-CBS | 13601.95 | 13599.3 | TGGATCGTGATGACTGTCCCGACAAGCTTACGTATCTCACT (sp18)(sp18)(3'aminoC6)(CBS) | 20 |
| 2f-iminobiotin | 13653.28 | 13650.7 | TGGATCGTGATGACTGTCCCGACAAGCATACGTATCTCACT (sp18)(sp18)(3'aminoC6)(iminobiotin) | 21 |
| 1b-cooh | 10629.15 | 10660.4 | (5'carboxy)(sp18)CGGCGATCGTGAAGGAGGANNNNTTGAGTG AG | 22 |
| 3a-biotin | 14720.81 (+DMT) | 14722.0 | TGGATCGTGATGACTGTCCCGACAAGCATACGTATCTCACTC A(sp18)(sp18)(3'biotinTEG) | 23 |
| 3b-amine | 14046.35 | 14045.0 | TGGATCGTGATGACTGTCCCGACAACCATGGGTATCTCACTC A(sp18)(sp18)(3'aminoC6) | 24 |
| 3b-desthiobiotin | 14242.35 | 14243.0 | TGGATCGTGATGACTGTCCCGACAACCATGGGTATCTCACTC A(sp18)(sp18)(3'aminoC6)(desthiobiotin) | 25 |
| 4a-amine | 14659.55 (+DMT) | 14661.0 | TGGATCGTGATGACTGTCCCGACAAGCATACGTATCTCACTC AG(sp18)(sp18)(3'aminoC6) | 26 |
| 4a-desthiobiotin | 14555.55 | 14556.0 | TGGATCGTGATGACTGTCCCGACAAGCATACGTATCTCACTC AG(sp18)(sp18)(3'aminoC6)(desthiobiotin) | 27 |
| 5a-amine | 14319.45 | 14318.0 | TGGATCGTGATGACTGTCCCGACAAGCATACGTATCTCACTC AGT(sp18)(3'aminoC6) | 28 |
| 5b-biotin | 15045.21 | 15041.0 | TGGATCGTGATGACTGTCCCGACAAGCATACGTATCTCACTC AGT(sp18)(sp18)(3'biotinTEG) | 29 |
| 6a-amine | 15252.95 (+DMT) | 15255.0 | TGGATCGTGATGACTGTCCCGACAAGCATACGTATCTCACTC AGTC(sp18)(3'aminoC6) | 30 |
| 6a-desthiobiotin | 15148.95 | 15149.0 | TGGATCGTGATGACTGTCCCGACAAGCATACGTATCTCACTC AGTC(sp18)(sp18)(3'aminoC6)(desthiobiotin) | 31 |
| 4b-amine | 14675.55 (+DMT) | 14678.0 | TGGATCGTGATGACTGTCCCGACAACCATGGGTATCTCACTC A(sp18)(sp18)(3'aminoC6) | 32 |
| 4b-GLCBS | 14728.55 | 14728.0 | TGGATCGTGATGACTGTCCCGACAACCATGGGTATCTCACTC A(sp18)(sp18)(3'aminoC6)(GLCBS) | 33 |

TABLE 1 -continued

List of modified DNA oligonucleotides, expected and observed masses, and their sequences.
Oligonucleotide Sequences and LC/MS Characterization

| name | expected mass (Da) | observed mass (Da) | sequence | SEQ ID NO: |
|---|---|---|---|---|
| 3c-amine | 14346.35 (+DMT) | 14346.0 | TGGATCGTGATGACTGTCCCGACAAACCGGTGTATCTCACTC A(sp18)(sp18)(3'aminoC6) | 34 |
| 3d-amine | 14345.35 (+DMT) | 14347.0 | TGGATCGTGATGACTGTCCCGACAACAATTGGTATCTCACTC A(sp18)(sp18)(3'aminoC6) | 35 |
| 3e | 14346.35 (+DMT) | 14332.0 | TGGATCGTGATGACTGTCCCGACAATNNNNAGTATCTCACTC A(sp18)(sp18)(3'aminoC6) | 36 |
| 3f-amine | 14346.35 (+DMT) | 14348.0 | TGGATCGTGATGACTGTCCCGACAACAGCTGGTATCTCACTC A(sp18)(sp18)(3'aminoC6) | 37 |
| 3c-CBS | 14229.35 | 14231.0 | TGGATCGTGATGACTGTCCCGACAAACCGGTGTATCTCACTC A(sp18)(sp18)(3'aminoC6)(CBS) | 38 |
| 3d-iminobiotin | 14270.65 | 14270.0 | TGGATCGTGATGACTGTCCCGACAACAATTGGTATCTCACTC A(sp18)(sp18)(3'aminoC6)(iminobiotin) | 39 |
| 3f-GLOBS | 14399.35 | 14398.0 | TGGATCGTGATGACTGTCCCGACAACAGCTGGTATCTCACTC A(sp18)(sp18)(3'aminoC6)(GLCBS) | 40 |
| 3g-GLCBS | 14398.35 | 14397.0 | TGGATCGTGATGACTGTCCCGACAAGAATTCGTATCTCACTC A(sp18)(sp18)(3'aminoC6)(GLCBS) | 41 |
| 4b-desthiobiotin | 14570.55 | 14570.0 | TGGATCGTGATGACTGTCCCGACAAGAATTCGTATCTCACTC AG(sp18)(sp18)(3'aminoC6)(desthiobiotin) | 42 |
| 3h-dithiol | 14067.17 (+DMT) | 14068.0 | TGGATCGTGATGACTGTCCCGACAAGCTAGCGTATCTCACTC A(sp18)(3'thiolC3) | 43 |
| 3h-Bad | 17072.64 | 17166.0 | TGGATCGTGATGACTGTCCCGACAAGCTAGCGTATCTCACTC A(sp18)(3'thiolC3)(SMPEG2)(Bad) | 44 |
| 1c-amine | 10546 | 10546.0 | (5'amino5)(sp18)CGGCGATCGTGAAGGAGGAGTACTTGAGTG AG | 45 |
| 3c-propargyl | 14155 | 14159.0 | TGGATCGTGATGACTGTCCCGACAAACCGGTGTATCTCACTC A(sp18)(sp18)(3'aminoC6)(propargyl) | 46 |
| 3c-rapamycin | 15213 | 15215.1 | TGGATCGTGATGACTGTCCCGACAAACCGGTGTATCTCACTC A(sp18)(sp18)(3'aminoC6)(propargyl)(rapamycin) | 47 |
| 3i-dithiol | 14411.47 (+DMT) | 14414.0 | TGGATCGTGATGACTGTCCCGACAACTGCAGGTATCTCACTC A(sp18)(sp18)(3'thiolC3) | 48 |
| 3i-BakL78A | 16014.44 | 16017.0 | TGGATCGTGATGACTGTCCCGACAACTGCAGGTATCTCACTC A(sp18)(sp18)(3'thiolC3)(SM(PEG)2)(BakL78A) | 49 |
| 3h-Bak | 15712.14 | 15711.5 | TGGATCGTGATGACTGTCCCGACAAGCTAGCGTATCTCACTC A(sp18)(3'thiolC3)(SM(PEG)2)(Bak) | 50 |
| 1d-cooh | 10630.15 | 10589.0 | (5'carboxy)(sp18)CGGCGATCGTGAAGGAGGGCATGCTGAGTG AG | 51 |
| 1e-cooh | 10630.15 | 10629.0 | (5'carboxy)(sp18)CGGCGATCGTGAAGGAGGCTCGAGTGAGTG AG | 52 |
| 1c-amine | 10891.34 | 10889.0 | (5'amino5)(sp18)(sp 18)CGGCGATCGTGAAGGAGGAGTACTTG AGTGAG | 53 |
| 1c-BG | 11256.76 | 11259.0 | (benzylguanine)(5'amino5)(sp18)(sp18)CGGCGATCGTGAAGGA GGAGTACTTGAGTGAG | 54 |
| 1f-cooh | 10630.15 | 10629.0 | (5'carboxy)(sp18)CGGCGATCGTGAAGGAGGGTCGACTGAGTG AG | 55 |
| 1g-BG | 11256.72 | 11257.0 | (benzylguanine)(5'amino5)(sp18)(sp18)CGGCGATCGTGAAGGA GGACCGGTTGAGTGAG | 56 |
| 1a-BG | 11216.72 | 11216.5 | (benzylguanine)(5'amino5)(sp18)(sp18)CGGCGATCGTGAAGGA GGCTAGCCTGAGTGAG | 57 |

TABLE 1 -continued

List of modified DNA oligonucleotides, expected and observed masses, and their sequences.
Oligonucleotide Sequences and LC/MS Characterization

| name | expected mass (Da) | observed mass (Da) | sequence | SEQ ID NO: |
|---|---|---|---|---|
| 1b BG | 10893.42 | 10976.5 (wide) | (benzylguanine)(5'amino5)(sp18)CGGCGATCGTGAAGGAGGAN NNNTTGAGTGAG | 58 |
| 1d-BG | 10872.42 | 10874.5 | (benzylguanine)(5'amino5)(sp18)CGGCGATCGTGAAGGAGGCA TGCCTGAGTGAG | 59 |
| 3g-CBS | 14228.35 | 14228.0 | TGGATCGTGATGACTGTCCCGACAAGAATTCGTATCTCACTC A(sp18)(sp18)(3'aminoC6)(CBS) | 60 |
| 3j-Bad | 17114.72 | 17134.0 | TGGATCGTGATGACTGTCCCGACAAGCATGCGTATCTCACTC A(sp18)(3'C6dithiol)(SM(PEG)2)(Bad) | 61 |
| 3b-CBS | 14229.35 | 14230.0 | TGGATCGTGATGACTGTCCCGACAACCATGGGTATCTCACTC A(sp18)(sp18)(3'aminoC6)(CBS) | 62 |
| 7a-glutarate | 11471.67 | 11471.0 | GGCTAATCCGTACGATAGGCATGCATGAGTGGGA(spacer) (spacer)(3'aminoC3)(glutarate) | 63 |
| 8a-amine | 16620.8 | 16617.4 | (5'amino5)CCCTGTACACAGCTCAAAGTTGCTGAAATGATCGT ATGCTAAACCATCCCACTC | 64 |
| 8b-GLCBS | 16915.8 | 16915.9 | (GLCBS)(5'amino5)CCCTGTACACTTCCTCAAGTTGCTGAAATG ATCGTATGCTAAACCATCCCACTC | 65 |

Synthesis of Target-DNA Conjugates and Antibody-DNA Conjugates

Activation of DNA and conjugation of protein targets or antibodies were performed as previously reported.[4] Antibodies were first dialyzed overnight at 4° C. against PBS using a Slide-A-Lyzer MINI dialysis cartridge (Pierce) with 10,000 MWCO. DNA-antibody conjugates were separated from excess unreacted DNA by repeated ultrafiltration using an Amicon microspin column with a 100,000 MWCO filter. The anti-streptavidin antibody (#ab10020) and anti-CAII antibody (#ab7001) were purchased from Abcam. The Penta-His Antibody (#34660) was purchased from Qiagen.

Primer Extension Reactions for Antibody-Mediated ISID.

An extension mixture was prepared as a master mix containing a total of 13 µL per reaction including 10× NEB Buffer 2 (2 µL), dNTPs (660 pmol each), DNA-linked antibody (0.2 pmol in 0.2-2 µL PBS), with or without 0.2 pmol target protein (2 µL in PBS). The master mix was aliquoted for each sample and warmed to 37° C. for 5 min before addition of 0.2 pmol of the appropriate DNA-linked ligand (2 µL in water). The mixture was incubated at 37° C. for 15 min prior to addition of a DNA polymerase in 5 µL NEB Buffer 2. Extensions with Klenow exo⁻ used 2.5 U enzyme. Where noted, these reactions were supplemented with 2 U Exo I or were performed with 2.5 U Klenow Fragment, 2.5 U DNA Polymerase I, 0.5 U T4 DNA with 0.5 µg BSA, or 5 U phi29 DNA with 0.5 µg BSA. After addition of polymerase and/or exonuclease, the reaction was incubated 15 min at 37° C. prior to heat inactivation of the enzyme(s) at 75° C. for 20 min.

In cases where recombinant SA or CAII was added to HeLa lysate at 0.01% wt, the protein content of the HeLa cell lysate was first estimated using the Modified Lowry Assay Kit (Thermo Scientific). HeLa cell lysate replaced water in the primer extension reaction mixture, and was added in volumes of 5.7-8.5 µL, with a maximum weight of 60 µg total protein added.

ISID Experiments with SNAP-Tagged Targets.

A primer extension reaction mixture was prepared as a master mix containing a total of 13 µL per reaction containing HEK-293T cell lysate (8.85 µL) previously transfected with vectors encoding SNAP-tag or SNAP/target fusions (see below), 10×NEB Buffer 2 (1.5 µL), dNTPs (660 pmol each), and 0.2 pmol DNA-BG (2 µL in water). This mixture was incubated at 37° C. for 15 min before aliquoting and addition of 0.2 pmol of the corresponding DNA-linked ligand(s) (2 µL in water). The resulting mixture was incubated at 37° C. for 15 min prior to the addition of 0.5 U T4 DNA polymerase (5 µL in NEB Buffer 2 supplemented with 0.5 µg BSA). Primer extension proceeded for 15 min at 37° C. before heat inactivation for 20 min at 75° C.

Quantitative PCR (qPCR) Analysis of Primer Extension Reactions.

Each 25 µL qPCR reaction contains 12.5 µL per reaction 2×SYBR Green iQ Supermix (Bio-Rad), 1 pmol Primer A: 5'-TGGATCGTGATGACTGTCC-3' (1 µL in water, SEQ ID NO: 66), 1 pmol Primer B: 5'-CGGCGATCGTGAAGGAG-3' (1 µL in water, SEQ ID NO: 67) and 1 µL primer extension product. Quantitative PCR was performed on a CFX-96 Real-Time System with a C1000 Thermocycler (Bio-Rad). PCR conditions: 5 min at 95° C., followed by 40 cycles of [30 sec at 95° C., 30 sec at 50° C., 30 sec at 72° C.].

Enrichment Factor Experiments

To investigate the ability of given affinity reagents and polymerases to enrich sequences corresponding to known target-ligand interactions, primer extension reactions were performed on mixtures of binding and non-binding DNA-linked small molecules linked to sequences with different restriction sites. These mixtures were subjected to primer extension reactions with samples containing the target protein or on a sample lacking target protein or containing a non-target protein as a negative control. To minimize the effect of PCR bias and reduce mutations introduced in PCR,[5]

an analytical qPCR was performed to determine the appropriate number of amplification cycles for each sample. Then one microliter of the primer extension product was subjected to PCR for the appropriate number of cycles before digestion with the corresponding restriction enzyme for one hour at 37° C. The digested samples were analyzed by PAGE (10% TBE, 200V, 30 min), stained with SYBRGold and imaged using an AlphaImager.

Competitive IDPCR.

Primer extension reactions were described as above using CAII covalently labeled with 7a-glutarate. Glutarate-linked DNA was prepared by stirring 20 nmol 3'-amine linked DNA (40 µL in water) with 40 µL 1M KHPO$_4$ pH 7.1, 140 µL water, 2 mmol glutaric anhydride (10.4 µL in DMSO) and 390 µL DMSO overnight at room temperature. The resulting glutarate-linked DNA was purified by ethanol purification and characterized by LC/MS. After conjugation to CAII, as described above, the DNA-CAII was used in an IDPCR experiment with 8a-amine as a negative control or 8b-GL-CBS. The reactions were conducted either without additives or with 0.2 pmol, 2 pmol, or 20 pmol added αCAII polyclonal antibody (2 µL in PBS) (Abcam) or with 0.2 pmol, 2 pmol, or 20 pmol added GLCBS (2 µL in 10% DMSO). The primer extension reactions were analyzed by qPCR as described above.

Model Library×Library IDPCR.

The extension experiments were performed with a target protein sample comprised of 0.2 pmol of a 1:1:256 mixture of 1d-SA:1e-CAII:1b-GST or with a control containing 0.2 pmol of a 1:1:256 mixture of 1d:1e:1b, but lacking target proteins. The ligand mixture contained 0.2 pmol of a 1:1:1:1:256 mixture of 2b-biotin:2d-desthiobiotin:2c-GLCBS:2a-CBS:2e.

In the series investigating the concentration of Klenow exo$^-$, either 2.5 U, 0.1 U, 0.004 U or 0.00016 U Klenow exo$^-$ was added and incubated for 15 min. In the series of selections exploring extension temperature, the primer extension master mix was incubated at the given temperature, 33° C. or 41° C. on a thermocycler prior to addition of the DNA-ligand mixture and after addition of Klenow exo$^-$. In the set with a smaller amount of dNTPs, 20 pmol each were added to the primer extension mixture. When the concentration of the model libraries were varied, the ratio of the DNA-ligand mixture and the DNA-target mixture were held constant and 2 fmol, 20 fmol, 0.2 pmol, 2 pmol, or 20 pmol of each mixture was added to the primer extension mixture. Unless otherwise noted, the primer extension mixtures contain 12.5 nM Klenow exo$^-$, 10 nM DNA-target, 10 nM DNA-ligand and 33 µM dNTPs at 37° C.

TABLE 2

Illumina sequencing compatible primers used to prepare samples for model selections with varied primer extension conditions. SEQ ID NOs: 68-75.

| name | forward primer sequence |
|---|---|
| llumA1 | AATGATACGGCGACCACCGAGATCTACACTCTTTCCCT ACACGACGCTCTTCCGATCTTAGCAGCGGCGATCGTGA AGGAG |
| llumA2 | AATGATACGGCGACCACCGAGATCTACACTCTTTCCCT ACACGACGCTCTTCCGATCTGATGGACGGCGATCGTGA AGGAG |
| llumA3 | AATGATACGGCGACCACCGAGATCTACACTCTTTCCCT ACACGACGCTCTTCCGATCTTTTCTCGCGGCGATCGTGA AGGAG |

TABLE 2 -continued

Illumina sequencing compatible primers used to prepare samples for model selections with varied primer extension conditions. SEQ ID NOs: 68-75.

| name | |
|---|---|
| llumA4 | AATGATACGGCGACCACCGAGATCTACACTCTTTCCCT ACACGACGCTCTTCCGATCTTCTACCCGGCGATCGTGA AGGAG |
| llumA5 | AATGATACGGCGACCACCGAGATCTACACTCTTTCCCT ACACGACGCTCTTCCGATCTGTACCTCGGCGATCGTGA AGGAG |
| | reverse primer sequence |
| llumTLibB1 | CAAGCAGAAGACGGCATACGAGCTCTTCCGATCTTTAG GGTGGATCGTGATGACTGTCCC |
| llumTLibB2 | CAAGCAGAAGACGGCATACGAGCTCTTCCGATCTTGAG ACTGGATCGTGATGACTGTCCC |
| llumTLibB3 | CAAGCAGAAGACGGCATACGAGCTCTTCCGATCTCACT CATGGATCGTGATGACTGTCCC |

To prepare the samples for high throughput sequencing, a PCR reaction was performed for each selection using a pair of Illumina compatible primers (see Table 4). Samples were amplified for the number of cycles required to reach the top of the linear range in qPCR. Products of these PCR reactions were cleaned up by gel purification using a 3% agarose gel and a gel extraction kit (Qiagen). The picoGreen QuantIT kit (Invitrogen) was used to measure the concentration of DNA in the purified samples. Samples were pooled and the concentration of the pooled sample was measured using qPCR compared to a sample of known concentration. The samples were analyzed on an Illumina HiSeq (Partners Center for Personalized Genomic Medicine), and the resulting sequences were analyzed using an in-house MATLAB script.

Comparing Primer Extension with Various Polymerases Using Model Library×Library IDPCR.

Primer extension reactions were performed as described above. For the selections using 6-nt complementary regions, 0.2 pmol of mixture of 1:1:1:1:1:256 containing 2b-biotin:2d-desthiobiotin:2f-iminobiotin:2c-GLCBS:2e was added as the DNA-ligand model library. For the selections using 8-nt complementary regions, 0.2 pmol of a 1:1:1:1:1:256 mixture of 3a-biotin:3b-desthiobiotin:3d-iminobiotin:3f-GLCBS:3c-CBS:3e was added. The model DNA-target library consisted of 0.2 pmol of a 1:1:256 mixture of 1d-SA:1e-CAII:1b-GST. Negative control model selections lacking targets were conducted using a 0.2 pmol of a 1:1:256 mixture of 1d:1e:1b.

TABLE 3

Illumina sequencing compatible primers used to prepare samples for model different DNA polymerases. SEQ ID NOs: 76-88.

| name | forward primer sequence |
|---|---|
| llumA1 | AATGATACGGCGACCACCGAGATCTACACTCTTTCCCTACAC GACGCTCTTCCGATCTTAGCAGCGGCGATCGTGAAGGAG |
| llumA2 | AATGATACGGCGACCACCGAGATCTACACTCTTTCCCTACAC GACGCTCTTCCGATCTGATGGACGGCGATCGTGAAGGAG |
| llumA3 | AATGATACGGCGACCACCGAGATCTACACTCTTTCCCTACAC GACGCTCTTCCGATCTTTTCTCGCGGCGATCGTGAAGGAG |
| llumA6 | AATGATACGGCGACCACCGAGATCTACACTCTTTCCCTACAC GACGCTCTTCCGATCTATGGCTCGGCGATCGTGAAGGAG |

TABLE 3 -continued

Illumina sequencing compatible primers used to prepare samples for model different DNA polymerases. SEQ ID NOs: 76-88.

| name | |
|---|---|
| llumA8 | AATGATACGGCGACCACCGAGATCTACACTCTTTCCCTACAC GACGCTCTTCCGATCTTGCGATCGGCGATCGTGAAGGAG |
| llumA10 | AATGATACGGCGACCACCGAGATCTACACTCTTTCCCTACAC GACGCTCTTCCGATCTCGATCACGGCGATCGTGAAGGAG |
| llumA11 | AATGATACGGCGACCACCGAGATCTACACTCTTTCCCTACAC GACGCTCTTCCGATCTCTCACCCGGCGATCGTGAAGGAG |
| llumA12 | AATGATACGGCGACCACCGAGATCTACACTCTTTCCCTACAC GACGCTCTTCCGATCTCTCACCCGGCGATCGTGAAGGAG |
| llumA14 | AATGATACGGCGACCACCGAGATCTACACTCTTTCCCTACAC GACGCTCTTCCGATCTTGTCTGCGGCGATCGTGAAGGAG |
| llumA15 | AATGATACGGCGACCACCGAGATCTACACTCTTTCCCTACAC GACGCTCTTCCGATCTGACATCCGGCGATCGTGAAGGAG |
| llumA17 | AATGATACGGCGACCACCGAGATCTACACTCTTTCCCTACAC GACGCTCTTCCGATCTAGTCCTCGGCGATCGTGAAGGAG |
| llumA20 | AATGATACGGCGACCACCGAGATCTACACTCTTTCCCTACAC GACGCTCTTCCGATCTAGACGACGGCGATCGTGAAGGAG |
| reverse primer sequence | |
| llumB | CAAGCAGAAGACGGCATACGAGCTCTTCCGATCTTGGATCGT GATGACTGTCCC |

Primer extensions on the model library with 6-nt complementary regions were conducted with either 5 U Klenow exo⁻, 5 U Klenow exo⁻ and 2 U Exo I, 5 U Klenow Fragment, or 5 U DNA polymerase I. Primer extensions on the model library with 8-nt complementary regions were conducted with 5 U DNA polymerase I or 0.5 U T4 DNA polymerase. The primer extension products were subjected to qPCR and subsequent PCR with a pair of Illumina sequencing-compatible primers (see Table 5). The resulting PCR products were either gel purified by 3% agarose gel (TBE, 100V, 40 min) and cleaned up with the Qiagen gel extraction kit or PAGE purified (10% TBE, 200V, 25 min). Gels were stained with SYBRGold (Invitrogen). DNA was eluted from PAGE gel fragments by incubating at 37° C. for 4 hours in 10 mM Tris-HCL pH 8 and cleaned up using the Qiagen PCR cleanup kit. Purified PCR products were quantified using the picoGreen Quant-iT kit (Invitrogen) and pooled. The samples were pooled to an overall concentration of 2 nM and the concentration was verified by qPCR using primers complementary to the Illumina adapters and a reference sample of known concentration. The pooled sample was prepared and sequenced on a MiSeq using a 50-cycle sequencing kit (Illumina) according to manufacturer's protocols. The resulting DNA sequences were analyzed using an in-house MATLAB script.

Model Library×Library ISID with SNAP-tagged Target Protein.

Previously transfected HEK-293T cells were lysed as described below by passing through a G-22 needle 20 times before centrifugation for 3 min at 20,000 g. The resulting cleared lysate (8.85 µL) was incubated with 10×NEB Buffer 2 (1.5 µL), dNTPs (660 pmol each, 0.66 µL), and 2 pmol DNA-BG (2 µL in water). This mixture was incubated at 37° C. for 30 min before quenching with SNAP Cell Block (NEB), (200 pmol, 2 µL in 10% DMSO) for 15 min. The cell lysate previously transfected with SNAP-CA was labeled with 1g-BG; SNAP-Bcl-xL with 1a-BG; SNAP-FKBP with 1c-BG; FRB-SNAP with 1d-BG and SNAP with 1b-BG. The labeled, quenched lysates were pooled at a 1:1:1:256 ratio of SNAP-CA:SNAP-Bcl-xL:SNAP-FKBP:SNAP. To 8.85 µL of pooled lysate was added 2 pmol (2 µL in water) DNA-linked ligand model library containing a 1:1:1:1:1: 256 ratio of 3j-Bad:3h-Bak:3i-BakL78A:3d-CBS:3f-GL-CBS:3c-rapamycin:3e. After a 15 min incubation at 37° C. to allow equilibration of binding, 0.5 U T4 DNA polymerase+0.5 µg BSA in 4 µL NEB Buffer 2 was added and incubated for 15 min at 37° C. The primer extension reaction was inactivated by heating to 75° C. for 20 min.

To prepare samples for high throughput sequencing, adapters compatible with Illumina paired end sequencing were installed in two sequential PCR steps. An analytical qPCR was performed in a 25 µL reaction volume with a final concentration of 1× Q5 buffer, 200 µM each dNTPs, 0.5 µM each primer, 1.25 µL 10×SYBR Green I (Invitrogen), 0.25 U Q5 Hot Start DNA polymerase (NEB), and 1 µL of the ISID primer extension product (Primers: 5'-TGGAGTTCA-GACGTGTGCTCTTCCGATCTTGGATCGTGATGACTG TCCC-3' (SEQ ID NO: 89) and 5'-ACACTCTTTCCCTA-CACGACGCTCTTCCGATCTNN NNATCGGCGATCGT-GAAGGAG-3' (SEQ ID NO: 90) or 5'-ACACTCTTTC-CCTACAC GACGCTCTTCCGATCTNNNNGATCGGCGATCGT-GAAGGAG-3' (SEQ ID NO: 91)). PCR Conditions: 30 sec at 95° C., followed by 40 cycles of [10 sec at 95° C., 10 sec at 65° C., 20 sec at 72° C.]. The samples were prepared in 50 µL PCR reactions, stopping at the $C_T$ value of each sample. Primers were removed using a PCR Cleanup Kit (Qiagen). The resulting samples were diluted 1:100 and 1 µL was used as a template for the $2^{nd}$ qPCR and PCR (Primers: 5'-AATGATACGGCGACCACCGAGATCTACACAT-TACTCGACACTCTTTC CCTACACGAC-3' (SEQ ID NO: 92) or 5'-AATGATACGGCGACCACCGAGATC-TACA CTCCGGAGAACACTCTTTCCCTACACGAC-3' (SEQ ID NO: 93) or 5'-AATGATAC GGCGACCACCGA-GATCTACACCGCTCATTACACTCTTTCCCTACAC-GAC-3' (SEQ ID NO: 94) and 5'-CAAGCAGAAGACG-GCATACGAGATGTGCGGACGTGACTGGA GTTCAGACGTGTGCT-3' (SEQ ID NO: 95) or 5'-CAAGCAGAAGACGGCATACGAGA TTACGTACG-GTGACTGGAGTTCAGACGTGTGCT-3' (SEQ ID NO: 96) or 5'-CAAGC AGAAGACGGCATACGAGA-TATATCAGTGTGACTGGAGTTCAGACGTGTGCT-3' (SEQ ID NO: 97)). The products of the $2^{nd}$ PCR were purified by PAGE (5% Criterion TBE (Bio-Rad), 200V, 40 min, stained with SYBR Gold (Invitrogen)). DNA was eluted from excised bands by incubating with 150 µL 10 mM Tris, pH 7.5 overnight in a 37° C. shaker. Eluted DNA was purified with a PCR Cleanup Kit (Qiagen), and quantified using the Quant-iT picoGreen kit (Invitrogen). The pooled samples were further quantified by qPCR using a Library Quantification Kit (Kapa Bioscience). The samples were sequenced on an Illumina MiSeq using a 50-bp sequencing kit.

USER Cloning.

PCR was performed separately on the target vector and insert using deoxyuracil containing primers with 1 µL Pfu Turbo Cx DNA Polymerase (Agilent) and 0.2 µL Taq DNA Polymerase (New England Biolabs). The resulting PCR product was purified using a PCR cleanup kit (Qiagen). The resulting insert (0.2 pmol) and vector (0.2 pmol) were incubated in a 10 µL reaction with 15 U DpnI and 0.75 U USER Enzyme (New England Biolabs) at 37° C. for one hour. The digested insert and vector were then heated to 80° C. for two min and cooled to 25° C. at a rate of 0.25° C./sec. The assembled vector was directly transformed into the NEB Turbo (New England Biolabs) or Mach 1 (Invitrogen) cloning strain.

Construction of CAII Plasmids.

The pACA plasmid was a kind gift of Carol Fierke. USER cloning was used to insert a His$_6$-tag at the N-terminus of CAII using these primers 5'ATGCACCATCACCACCAU-CACGCC-CATCACTGGGGGTAC-3' (SEQ ID NO: 98) and 5'ATGGTGGTGATGGUGCATGGTATATCTCCT-TCTTAAAGTTAAAC-3' (SEQ ID NO: 99) and at the C-terminus of CAII using these primers 5'ACCATCTTAAT-GATGATGATGAUGATGTTTGAAGGAAGCTTT-GATTTGCCTGTT C-3' (SEQ ID NO: 100) and 5'ACCAATCATCATCATCATTAAGATGGUC-CCATAGTC TGTATCCAA-3' (SEQ ID NO: 101).

To generate constructs for site specific labeling of CAII with maleimide-modified DNA, first, site-directed mutagenesis was performed to generate a CAII-His$_6$/C206S mutant using these primers: 5'CCCTCCTCTTCTGGAAAGCGT-GACCTGGATTGTGC-3' (SEQ ID NO: 102) and 5'GCA-CAATCCAGGTCACGCTTTCCAGAAGAGGAGG-3' (SEQ ID NO: 103). The CAII-His$_6$/C206S vector served as the basis for further site-directed mutagenesis, used to generate constructs with D19C using these primers: 5'CCT-GAGCACTGGCATAAGTGTTTCCCCATTGC-CAAGGGAGAG-3' (SEQ ID NO: 104) and 5'CTCTCCCT-TGGCAATGGGGAAACACTTATGCCAGTGCTCAGG-3' (SEQ ID NO: 105); D52C using 5'CCCTGAAGCCCCTGTCTGTTTCCTATTGT-CAAGCAAC TTCCCTGAGG-3' (SEQ ID NO: 106) and 5'CCTCAGGGAAGTTGCTTGACAATAGG AAACA-GACAGGGGCTTCAGGG-3' (SEQ ID NO: 107); K213C using 5'GTGACCTGGATTGTGCTCTGTGAAC-CCATCAGCGTCAGC-3' (SEQ ID NO: 108) and 5'GCT-GACGCTGATGGGTTCACAGAGCACAATCCAGGT-CAC (SEQ ID NO: 109); K252C using 5'GGCGCCCAGCTCAGCCACTGTGTAACAG-GCAAATCAA-3' (SEQ ID NO: 110) and 5'TTGATTTGC-CTGTTACACAGTGGCTGAGCTGGGCGCC-3' (SEQ ID NO: 111). Site-directed mutagenesis was performed either by amplification with Pfu Turbo DNA polymerase (Agilent) or by using a QuikChange kit (Agilent).

A CMVSport6.1 mammalian expression vector expressing human CAII was obtained from OpenBiosystems. A His$_6$-tag was added to the C-terminus of CAII using the same primers as above.

Construction of BclxL Plasmids.

A His$_6$-tag was added to the N-terminus of Bcl-xL of the pGEX-2T-Bcl-xL plasmid by USER cloning using these primers 5' ACTCATCATCACCATCAUCACCAGAG-CAACCGGGAGCTGGTGG-3' (SEQ ID NO: 112) and 5' ATGATGGTGATGATGAGUCCGGGGGGATCCACGC-3' (SEQ ID NO: 113). The His$_6$-tag was added to the C-terminus of Bcl-xL by USER cloning using these primers: 5'ACCACCACCACCACUGAGATCTCCGGGGGAAT-TCATCGTG-3' (SEQ ID NO: 114) and 5'-AGTGGTGAT-GATGGUGGTGGTGGTTGAAGCGTTCCTG-3'(SEQ ID NO: 115).

His$_6$-Bcl-xL was cloned from the pGEX-2T-Bcl-xL plasmid using the primers, 5'ATGCATCATCACCATCAUCACCA-GAGCAACCGGG-3' (SEQ ID NO: 116) and 5'AGAC-TATGGGACCATCUCAGCGGTTGAAGCGTTCCTGC-3' (SEQ ID NO: 117) and was cloned into the CMVSport6.1 backbone that was previously linearized with these primers 5'AGATGGTCCCATAGTCUGTATCCAAATAAT-GAATCTTCGGGTG-3' (SEQ ID NO: 118) and 5'ATGATGGTGATGATGCAUGGTCGCGCTGGCGGTC-3' (SEQ ID NO: 119).

Construction of FKBP and FRB Vectors.

A pcDNA2-FKBPmyc plasmid was obtained from Carolyn Bertozzi via Addgene (plasmid #20211).[6] A Kozak sequence and start codon was added to the FKBPmyc vector by re-ligating the vector after PCR-based linearization with these primers that were phosphorylated prior to PCR: 5'-CCATGGGAGTGCAGGTGGAAACC-3' (SEQ ID NO: 120) and 5'-TGGCCTGTGCTGGATATCTGCAG-3' (SEQ ID NO: 121). FKBP was cloned out of this vector using these primers 5'-ATCCAGAGGAGUGCAGGTGGAAAC-CATCT-3' (SEQ ID NO: 122) and 5'-ATTCTAGTCTACA-GAUCCTCTTCTGAGATGAGTTTTTGTTC-3' (SEQ ID NO: 123) and was then assembled into a pGEX-2T vector previously amplified with 5'-ACTCCTCTGGAUC-CACGCGGAACCAGATC-3' (SEQ ID NO: 124) and 5'-ATCTGTAGACTAGAAUTCATCGTGACTGACT-GACGATCTG-3' (SEQ ID NO: 125).

A plasmid expressing GST-FRB was obtained from Jie Chen via Addgene (plasmid #26607).[7] FRB was cloned out of the pGEX vector using these primers 5'-AGTCTATG-GAG-CUGATCCGAGTGGCCATC-3' (SEQ ID NO: 126) and 5'-AGTCTACTGCTTUGAGATTCGTCGGAACA-CATG-3' (SEQ ID NO: 127) and assembled into a pcDNA2 vector previously amplified with these primers 5'-AGCTC-CATAGACUCGAGCGGCCGC-3' (SEQ ID NO: 128) and 5'-CAAAGCAGTAGACUAGAGGGCCCGTTTAAAC-CCG-3' (SEQ ID NO: 129). A His$_6$-tag was added to the assembled pcDNA-FRB vector by re-ligating a linearized vector at the N-terminus of FRB by amplification with 5'-CACCATGGCGGCAGCGAGCTGATCCGAGTGGC-3' (SEQ ID NO: 130) and 5'-ATGATGGTGATGCATA-GACTCGAGCGGCCGC-3' (SEQ ID NO: 131). A Kozak sequence was added to pcDNA-His$_6$FRB by re-ligating the vector linearized with these primers: 5'-CACCATGGCG-GCTCTGAGCTGATCCGAGTGGCCATCC-3' (SEQ ID NO: 132) and 5'-GTGATGATGCAT-GGTGGCCGCCACT-GTGCTGG-3' (SEQ ID NO: 133).

Construction of SNAP-CAII and CAII-SNAP Vectors.

The pSNAPf vector was purchased from New England Biolabs. SNAP-CAII was generated by USER assembly of a PCR product of pSNAPf amplified with 5'-AGCTTCCT-TCAAATAAGCGUTTAAACTCGAGGTTAATTAAT-GAGCGG-3' (SEQ ID NO: 134) and 5'-ATTGATCCGC-CUGCAGGACC-3' (SEQ ID NO: 135) with a PCR product of the pACA vector amplified with 5'-CTTATTT-GAAGGAAGCUTTGATTTGCCTGTTCTTCAG-3' (SEQ ID NO: 136) and 5'-AGGCGGATCAAUGGCCCAT-CACTGGGGG-3' (SEQ ID NO: 137). CAII-SNAP was constructed by USER assembly of a pSNAPf PCR product amplified with 5'-AATTCACCGGUCTGTACAGATT-TAAATGC-3' (SEQ ID NO: 138) and 5'-AGCTTCCT-TCAAAGGAGGAUCAATGGACAAAGACTGCGAAAT-GAAGC-3' (SEQ ID NO: 139) with a pACA PCR product amplified with 5'-ATCCTCCTTTGAAGGAAGCUTT-GATTTGCCTGTTCTT-3' (SEQ ID NO: 140) and 5'-AC-CGGTGAATUCACCGCCACCATGGCCCAT-CACTGGGGG-3' (SEQ ID NO: 141).

Construction of SNAP-Bcl-xL, Bcl-xL-SNAP, SNAP-FRB, FRB-SNAP, SNAP-FKBP and FKBP-SNAP.

These vectors were assembled by restriction cloning using AgeI and AscI sites to clone upstream of the SNAP coding sequence and SbfI and XhoI sites to clone downstream of the SNAP coding sequence. To clone into the AgeI and AscI sites, the pSNAPf vector was first linearized using these primers: 5'-GTACAGACCGGTGAATTCACC-3' (SEQ ID NO: 142) and 5'-ATTTAAATGCTGGCGCGC-3' (SEQ ID NO: 143). To clone into the SbfI and XhoI sites the pSNAPf vector was first linearized with these primers: 5'-TAAACTCGAGGTTAATTAATGAGCGG-3' (SEQ ID NO: 144) and 5'-GATCCGCCTGCAGGAC-3' (SEQ ID NO: 145). Linearized vectors were gel purified prior to restriction digest. Bcl-xL was amplified from the CMVSport6.1-Bcl-xL vector with 5'-TATAACCGGTGCGGTT-GAAGCGTTCCTG-3' (SEQ ID NO: 146) and 5'-TTAAGGCGCGCCGGCCACCATGCAGAGCAAC-CGGGAGC-3' (SEQ ID NO: 147) to add AgeI and AscI sites. Bcl-xL was amplified from CMVSport6.1-Bcl-xL with 5'-TTAACCTGCAGGACAGAGCAACCGGGAGC-3' (SEQ ID NO: 148) and 5'-TATACTCGAGGCGGTT-GAAGCGTTCCTG-3' (SEQ ID NO: 149) to add SbfI and XhoI sites. FRB was amplified from the pcDNA-FRB vector with 5'-TATAGGCGCGCCGCCGCCACCATGGAG-3' (SEQ ID NO: 150) and 5'-TTAAACCGGTGCTGCCGC-CCTGC-3' (SEQ ID NO: 151) to add AgeI and AscI sites. Alternately, FRB was amplified from the pcDNA-FRB vector with 5'-TATACCTGCAGGAGCC-GCCACCATGGAG-3' (SEQ ID NO: 152) and 5'-TTAACTCGAGGCTGCCGC-CCTGC-3' (SEQ ID NO: 153) to add SbfI and XhoI sites. FKBP was amplified from the pcDNA-FKBPmyc vector with 5'-TTAAACCGGTTTCCAGTTTTAGAAGCTCCA-CATC-3' (SEQ ID NO: 154) and 5'-TATAGGCGCGCCGC-CACCATGGGAGTGC-3' (SEQ ID NO: 155) to add AgeI and AscI sites. FKBP was amplified from the pcDNA-FKBPmyc vector with 5'-TATACCTGCAGGAGCCAC-CATGG-GAGTGC-3' (SEQ ID NO: 156) and 5'-TTAACTCGAGTTCCAGTTTTAGAAGCTCCACATC-3' (SEQ ID NO: 157) to add SbfI and XhoI sites.

Protein Expression and Purification.

*E. Coli* BL21(DE3) (New England Biolabs) was transformed with the appropriate bacterial expression vector and plated on LB/Carb plates.

CAII was expressed according to a protocol kindly provided by Carol Fierke, described here. Fifteen milliliters overnight culture previously inoculated with a colony of *E. Coli* BL21(DE3) freshly transformed with pACA was used to inoculate 750 mL 2×YT medium supplemented with 3 g tryptone, 54 mL 5× M9 Minimal Salts, 15 mL 20% glucose, 150 µL 0.3M $ZnSO_4$, and 750 µL 100 mg/mL carbenicillin. The culture was grown in a 37° C. shaker until $OD_{600}$=0.8-1.0, when expression of CAII was induced by addition of 250 µL 1M IPTG. The culture was then transferred to a 30° C. shaker and grown for 4-5 hours. Cells were harvested by centrifugation at 5,000 g for 10 min and the cell pellet was stored at −80° C. $His_6$-tagged CAII was purified using Ni-NTA agarose (Qiagen) according to standard protocols.

Expression of pGEX-Bcl-xL was performed according to standard protocols. Expression of FRB from the pGEX-FRB vector and of FKBP from the pGEX-FKBP vector was performed as previously described.[8] GST-Bcl-xL, GST-FRB, GST-FKBP, and/or $His_6$-tagged derivates were purified according to standard protocols using GST-Bind Resin (Novagen). Overnight cleavage (18 hours) with thrombin (12 U)(EMDMillipore) at 4° C. was used to cleave the GST tag and elute from the glutathione resin. Purified proteins were separated from GST and thrombin by size exclusion chromatography using a Superdex 75 10/300 column (GE Healthcare) interfaced with an Akta FPLC (Amersham).

Tissue Culture.

HEK-293T cells (ATCC) and HeLa cells (ATCC) were maintained according to standard protocols in DMEM (high glucose, L-glutamine, pyruvate) supplemented with 10% fetal bovine serum (Gibco), penicillin, and streptomycin. Cultures were maintained at 37° C. with 70% humidity and an atmosphere of 5% $CO_2$ and were subcultured every 2-3 days.

General Protocol for Transfection.

One day prior to transfection, HEK-293T cells were seeded at a density of 250,000-500,000 cells per well in a 6-well plate that was pre-treated with 0.1% gelatin. According to manufacturer's protocols, at 70-90% confluency, the cells were transfected using 7.5 µL per well Lipofectamine 2000 (Invitrogen) with 2.5 µg per well plasmid DNA, using serum- and antibiotic-free DMEM during the transfection. Alternately, $1.5×10^6$ cells were seeded in a gelatinized 10-cm dish and transfected on the following day using 45 µL Lipofectamine 2000 complexed with 15 µg plasmid DNA.

Lysis.

Cells were harvested 48 hours after transfection. After rinsing with cold PBS, cells were removed from the plate by scraping in 1 mL PBS. Cells were pelleted by centrifugation for 4 min at 400 g. The supernatant was removed and the cell pellet was resuspended in 100-150 µL cold lysis buffer (10 mM Tris HCl, 137 mM NaCl, pH 7.5, 2 mM EDTA, 1 mM DTT, 1 µg/mL leupeptin, 1 mM PMSF). Alternately, a 10-cm plate was scraped in 5 mL PBS and the resulting cell pellet was resuspended in 500 µL cold lysis buffer. Resuspended cells were lysed either by 30 s sonication with a microtip probe sonicator or by passing 20 times through a syringe with a G-22 needle. Lysates were cleared by centrifugation at 20,000 g for 10 min at 4° C. The supernatant was either used directly or flash frozen in a dry ice/ethanol bath and stored at −80° C. Western blots used to verify expression were performed according to standard protocols.

REFERENCES FOR MATERIALS AND METHODS SECTION (1) Gitto, R.; Agnello, S.; Ferro, S.; De Luca, L.; Vullo, D.; Brydna, J.; Mader, P.; Supuran, C. T.; Chimirri, A. J. Med. Chem. 2010, 53, 2401; (2) a) Reznik, G. O.; Vajda, S.; Sano, T.; Cantor, C. R. Proc. Natl. Acad. Sci. USA 1998, 95, 13525. b) Torreggiani, A.; Fini, G. Biospectroscopy 1998, 4, 197; (3) Douglass, E. F., Jr.; Miller, C. J.; Sparer, G.; Shapiro, H.; Spiegel, D. A. J. Am. Chem. Soc. 2013, 135, 6092; (4) McGregor, L. M.; Gorin, D. J.; Dumelin, C. E.; Liu, D. R. J. Am. Chem. Soc. 2010, 132, 15522; (5) Kozarewa, I.; Ning, Z.; Quail, M. A.; Sanders, M. J.; Berriman, M.; Turner, D. J. Nat. Methods. 2009, 6, 291; (6) Czlapinski, J. L.; Schelle, M. W.; Miller, L. W.; Laughlin, S. T.; Kohler, J. J.; Cornish, V. W.; Bertozzi, C. R. J. Am. Chem. Soc. 2008, 130, 13186; (7) Vilella-Bach, M.; Nuzzi, P.; Fang, Y.; Chen, J. J. Biol. Chem. 1999, 274, 4266; (8) Banaszynski, L. A.; Liu, C. W.; Wandless, T. J. J. Am. Chem. Soc. 2005, 127, 4715.

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

Results

Figure 7A:
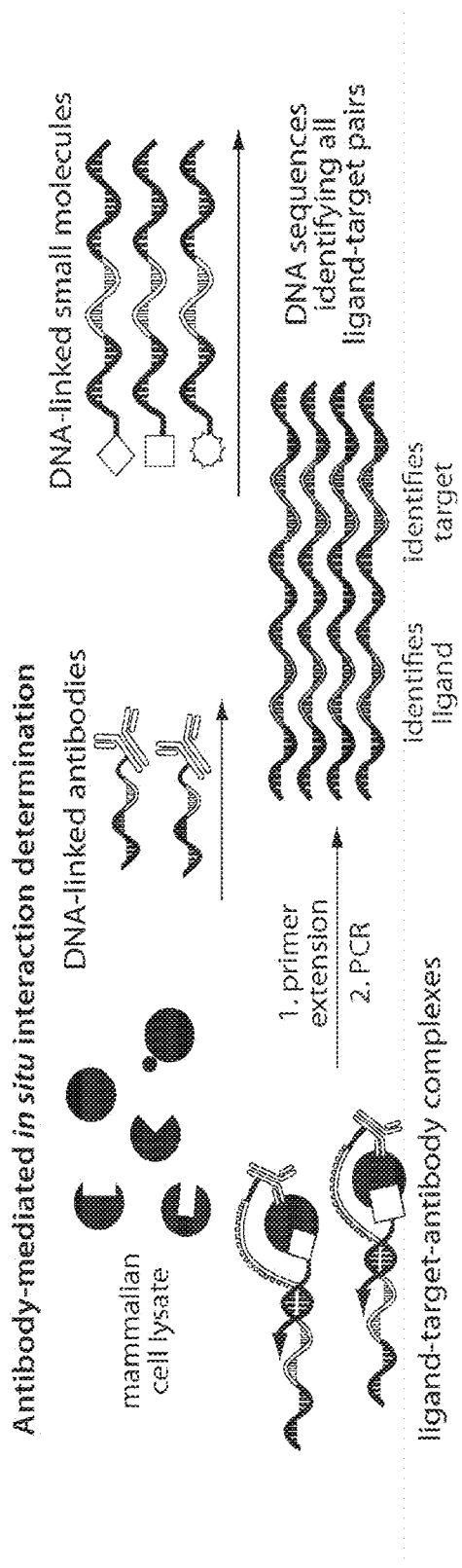
FIG. 7. A) Antibody-mediated in situ interaction determination (ISID) uses DNA-linked antibodies to recognize a target protein or epitope tag. B) A covalent bond can be formed between the target and identifying DNA strand in ISID by fusing the target to a self-labeling protein tag such as a SNAP-tag, CLIP-tag, or HaloTag. After primer extension and PCR, the resulting DNA encodes all ligand:target combinations.
Figure 7B:
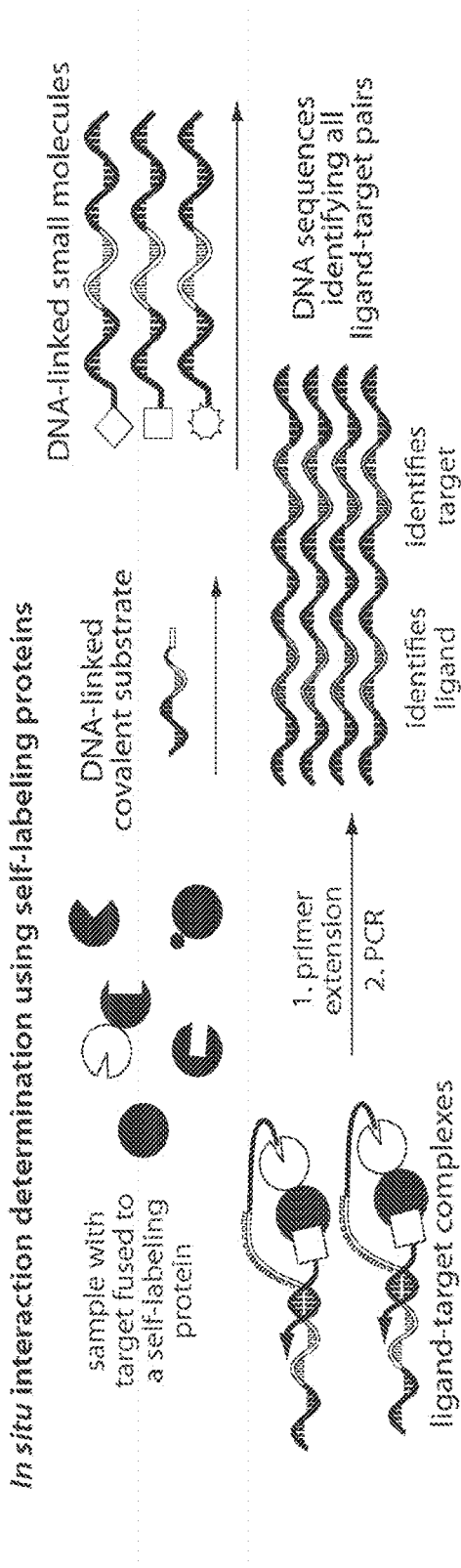

Pairs of DNA-linked antibodies have been used to measure the presence of proteins and protein-protein complexes by the proximity ligation assay[6] and the proximity extension assay.[7] Based on these concepts and on our previous development of interaction-dependent PCR (IDPCR),[3] it was speculated that formation of a ternary complex of a DNA-linked antibody, a protein target, and a DNA-linked small molecule could promote hybridization of the linked oligonucleotides and enable primer extension by a DNA polymerase in a manner that is dependent on binding of the ligand to the target (FIG. 7a). Such a system would offer the benefits of IDPCR, but without the significant limitation of requiring a purified target protein conjugated to a DNA oligonucleotide.

To test this hypothesis, quantitative PCR (qPCR) was used to compare the amount of primer extension product from reactions containing a DNA-linked anti-streptavidin antibody (DNA-αSA), streptavidin protein (SA), and a DNA-linked ligand. The DNA-linked ligand was varied among four small molecules: DNA-linked hexylamine (DNA-amine, no significant affinity for SA), DNA-linked Gly-Leu-carboxybenzene sulfonamide (DNA-GLCBS, no significant affinity for SA), and two ligands of SA: DNA-desthiobiotin ($K_d$=2 nM),[8] or DNA-biotin ($K_d$=40 pM).[9] Consistent with formation of an antibody:SA:biotin complex or an antibody:SA:desthiobiotin complex, samples containing DNA-αSA, SA, and either DNA-biotin or DNA-desthiobiotin were amplified much more quickly than those containing DNA-amine, containing DNA-GLCBS, or lacking SA, resulting in a qPCR cycle threshold ($C_T$) difference of five cycles ($\Delta C_T$=5, corresponding to a 32-fold difference in effective template availability) (FIG. 12). Together, these results demonstrate the ability of an antibody:protein:ligand ternary complex to trigger the selective amplification of a DNA sequence identifying the protein and ligand.

Because potential applications of ISID include selections on DNA-encoded chemical libraries, it was next investigated whether formation of a αSA:SA:biotin complex would result in selective amplification of the DNA sequence encoding SA:biotin when DNA-biotin was present in a mock library containing an excess of DNA-GLCBS. After ISID, restriction digestion and polyacrylamide gel electrophoresis (PAGE) of samples containing DNA-αSA, SA, and mixtures containing a 1:10, 1:100, or 1:1,000 ratio of DNA-biotin/DNA-GLCBS, it was found that the sequence corresponding to SA:biotin was enriched ~10-fold (FIG. 12). This relatively modest enrichment of the SA:biotin DNA sequence suggested that an improvement in the signal-to-noise ratio of ISID would be required to enable enrichment of sequences corresponding to interactions with affinities weaker than that of SA:biotin.

FIG. 12 illustrates in situ interaction determination with Klenow exo− and anti-streptavidin. A, B) Primer extension with Klenow exo− followed by qPCR reveals that samples with DNA-αSA, SA, and DNA-biotin or DNA-desthiobiotin were amplified more quickly than samples with DNA-amine, DNA-GLCBS, or with DNA-biotin but lacking SA. Error bars represent the standard deviation of three replicates. C) Mixtures of DNA-biotin/DNA-GLCBS were incubated with DNA-αSA in HeLa cell lysate with or without added streptavidin (0.01% wt) and were subjected to primer extension with Klenow exo−, followed by PCR and restriction digest, resulting in ~10-fold enrichment of the sequence corresponding to SA:biotin.

To optimize the effectiveness of ISID, key aspects of the primer extension step were investigated using the related and previously validated IDPCR system in which the purified target protein is covalently pre-conjugated to an identifiable DNA oligonucleotide.[3] In a series of model library× library experiments with 258 DNA-linked proteins and 260 DNA-linked ligands, parameters of the DNA extension step using the DNA polymerase Klenow exo− were systematically varied and it was found that varying primer extension conditions did not substantially improve enrichment factors for sequences corresponding to weaker interactions (FIGS. 13 and 14). A model library×library experiments was performed next using other mesophilic polymerases, and consistent with a previous report describing the ability of polymerases with 3'-exonuclease activity to increase the signal-to-noise ratio of the proximity extension assay,[7] it was found that IDPCR with T4 DNA polymerase and a complementary region of 8-nt or 9-nt resulted in 4.5- to 140-fold improvements in the enrichment of DNA sequences corresponding to ligand:target pairs with binding affinities ranging from 40 nM to 13 µM (FIGS. 15, 16 and 17).

Figure 8A:
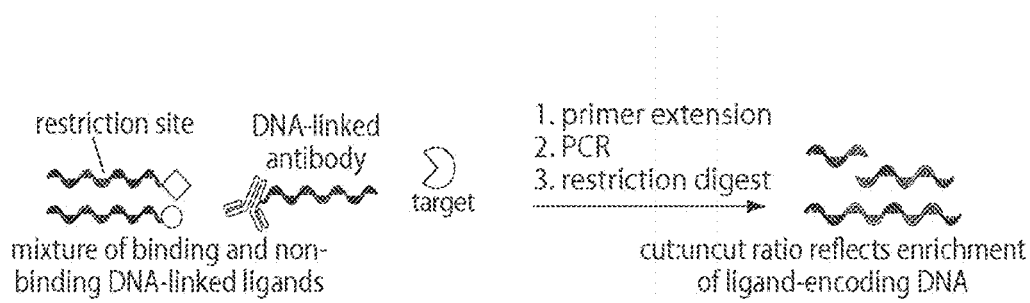
FIG. 8. A) The ability of ISID to enrich the sequence corresponding to a particular interaction is evaluated by incubating mixtures of binding and non-binding DNA-linked ligands with a target protein (here streptavidin, SA) and a DNA-linked antibody. After primer extension and PCR, a restriction digest is used to determine the fraction of the amplified sequences corresponding to the target:ligand interaction. B) ISID with DNA-αSA and 0.01% SA in HeLa lysate shows selective amplification of a sequence corresponding to SA:desthiobiotin in qPCR ($\Delta C_T$=4.7). C) ISID on a mock library containing mixtures of DNA-desthiobiotin and DNA-GLCBS shows ~1000-fold enrichment of a sequence corresponding to SA:desthiobiotin. D) When analyzed by qPCR, ISID with 0.01% carbonic anhydrase II (CAII) and DNA-αCAII in HeLa lysate shows rapid amplification of sequences corresponding to CA:GLCBS and CA:CBS, but not CA:desthiobiotin or CA:amine ($\Delta C_T$=4-5).
Figure 8B:
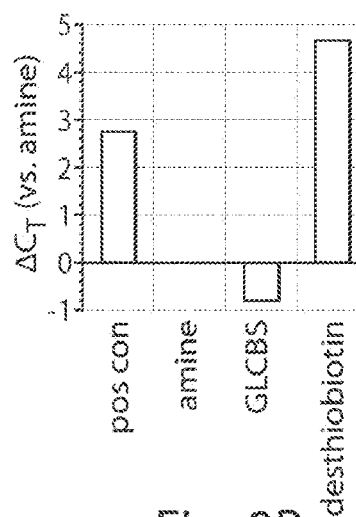
Figure 8C:
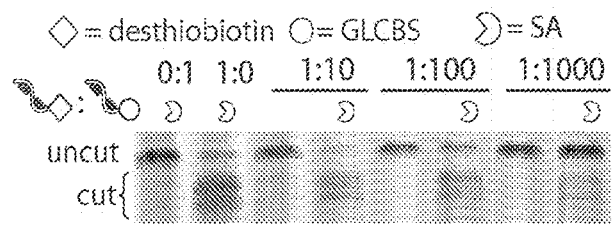

It was tested whether these improvements would apply to ISID and enable the enrichment of sequences corresponding to known binding interactions from a large excess of non-binding entities (FIG. 8a). Mixtures containing 1:10, 1:100, or 1:1,000 ratios of DNA-biotin/DNA-GLCBS were incubated with DNA-αSA and SA. Because the ability of ISID to detect protein:ligand binding in a complex mixture, such as a cell lysate, was of interest, HeLa cell lysate was also added to the solution so that SA was present at 0.01% weight (wt) relative to the total protein content of the HeLa cell lysate, an amount that is representative of the endogenous expression level of members of protein classes of interest such as MAP kinases, histone deacetylases, Ras-related proteins, and isocitrate dehydrogenases.10,11 After ISID, restriction digestion and PAGE analysis, ~1,000-fold enrichment of the sequence corresponding to SA:biotin was observed. Replacing Klenow exo− with T4 DNA polymerase and replacing a 6-nt complementary region with an 8-nt complementary region resulted in a 100-fold improvement in enrichment of the sequence encoding SA:biotin (FIGS. 8b, 8c, and 12).

Figure 8D:
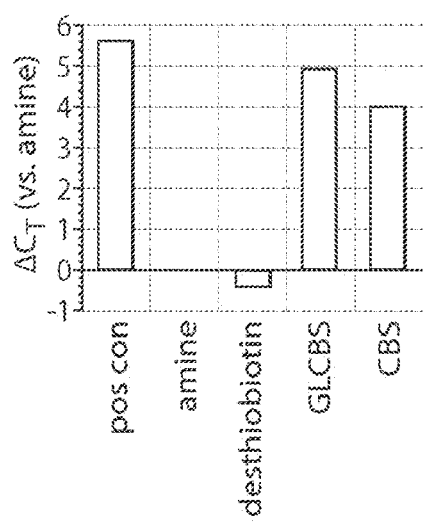
Figure 8E:
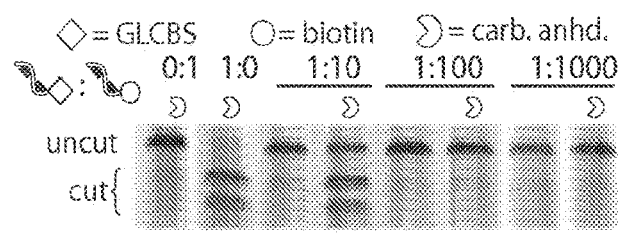

To determine whether ISID using T4 DNA polymerase could enrich DNA sequences corresponding to weaker ligand-target interactions, the interaction between carbonic anhydrase II (CAII) and its ligand GLCBS ($K_d$=40 nM)[12] was similarly studied and 10-fold enrichment of the sequence corresponding to CAII:GLCBS was observed (FIGS. 8d and 2e), despite the observation that the polyclonal antibody used to generate DNA-αCAII appears to partially compete for ligand binding, likely reducing the enrichment obtained by ISID using DNA-αCAII (FIG. 18). Together, these results demonstrate that for targets for which suitable antibodies exist, antibody-mediated ISID provides a selection-like method for the detection and reporting of small molecule-protein interactions from unpurified cell lysates in a single experiment.

Figure 9A:
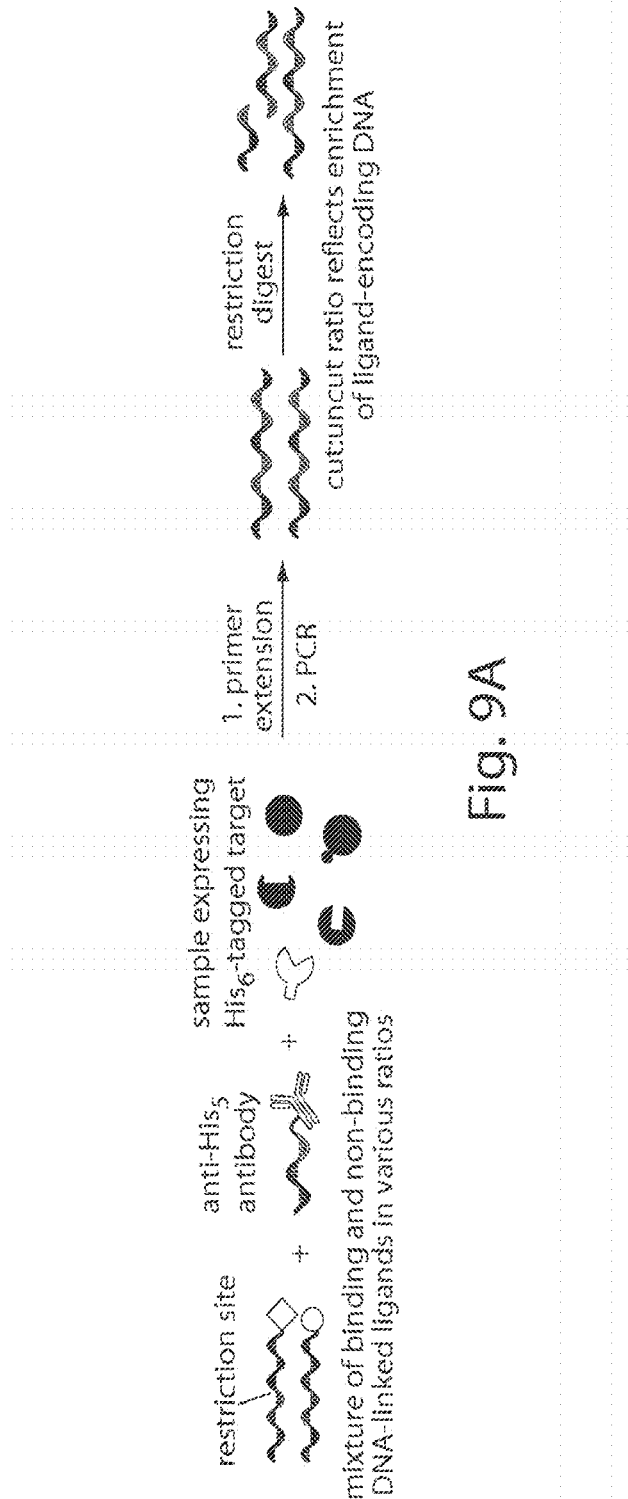

For some targets of interest, an antibody capable of selectively binding the target in solution without obscuring the ligand-binding site may be difficult to obtain. Because oligohistidine is a rare sequence among naturally occurring proteins,[13] it was hypothesized that an antibody against the His$_6$ epitope tag would be less likely to interfere with target protein function, including ligand binding. The ability of an anti-His$_6$ antibody (Qiagen, His$_6$:αHis $K_d$=10 nM)[14] linked to DNA (DNA-αHis) to participate in ISID with His$_6$-tagged target proteins was therefore investigated (FIG. 9a). ISID was performed with DNA-αHis and purified, C-terminally His$_6$-tagged CAII (CAII-His$_6$, 0.01% in HeLa cell lysate) and observed that using DNA-αHis resulted in 100-fold enrichment of DNA encoding CAII:GLCBS, representing a 10-fold improvement over the enrichment factor using DNA-αCAII (FIG. 19). These results demonstrate the feasibility of ISID mediated by an epitope tag-binding antibody instead of an antibody that directly binds the target protein's coding sequence.

Figure 9B:
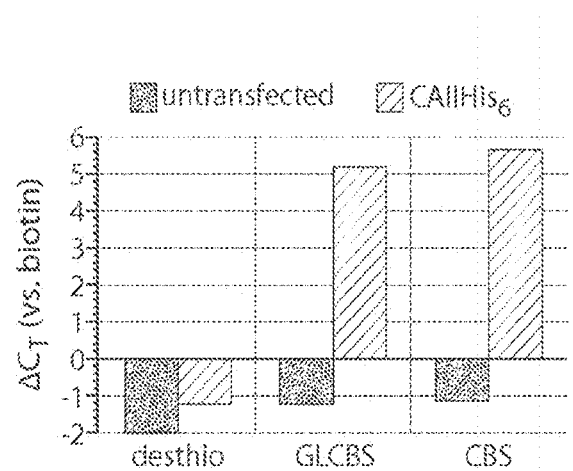
Figure 9C:
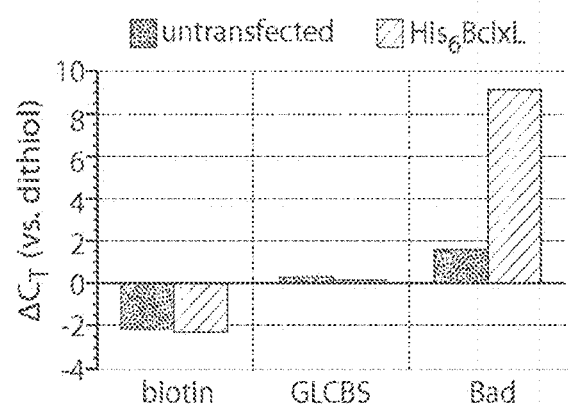
Figure 9D:
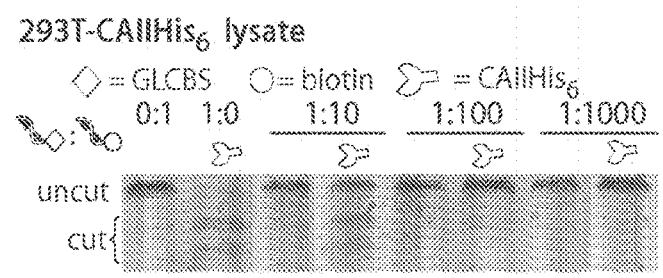
Figure 9E:
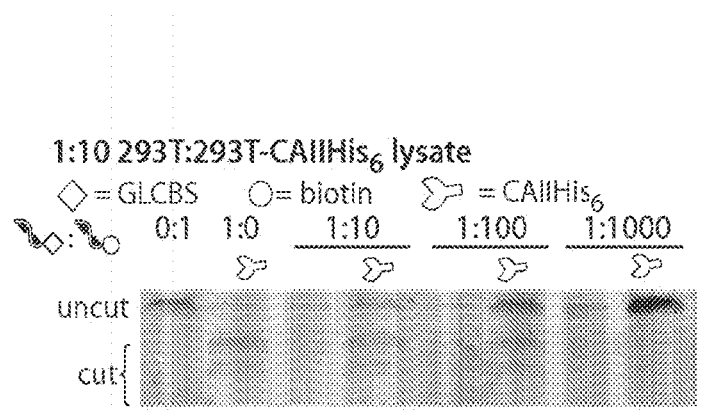
Figure 9F:
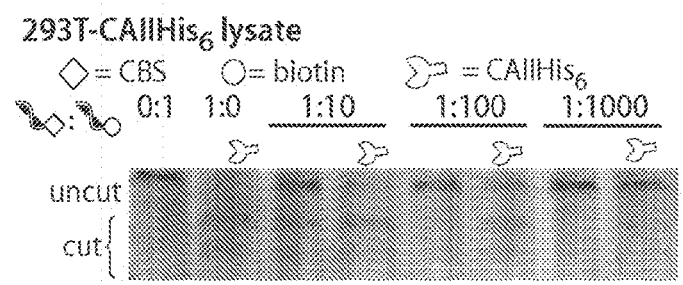

To assess the compatibility of ISID with unpurified, genetically encoded targets, HEK-293T cells were transiently transfected with a plasmid expressing CAII-His$_6$. An ISID enrichment experiment was performed in the resulting cell lysate using DNA-αHis and observed ~10-fold enrichment of the sequence corresponding to CAII:GLCBS (FIGS. 9b and 3d). When ISID was performed similarly using mixtures of DNA-CBS/DNA-biotin, ~100-fold enrichment of the sequence corresponding to CAII:CBS was observed (FIG. 9f). Enrichment by antibody-mediated ISID depends on formation of a ternary complex of DNA-antibody:target:ligand-DNA. According to a recent model of three-body binding,[15] for αHis-mediated ISID (His:αHis $K_d$=10 nM), a target protein concentration of 30 nM is optimal for CAII:GLCBS ($K_d$=40 nM),[12] but the optimal target concentration is 190 nM for CAII:CBS ($K_d$=3.2 μM).[16,15] By Western blot, it was determined that the concentration of CAII-His$_6$ in the 293T cell lysate was ~300 nM, corresponding to ~130 nM in the ISID assay (FIG. 20). Consistent with the model of three-body binding,[15] optimal ISID enrichment of the sequence corresponding to CAII:GLCBS (~100-fold) was observed when the 293T cell lysate transfected with a CAII-His$_6$ expression plasmid was diluted 1:10 into untreated 293T cell lysate (FIGS. 9e and 20). The enrichment of the sequence corresponding to CAII:CBS decreased to ~10-fold in this diluted lysate sample (FIG. 20).

FIG. 20 illustrates expression levels of CAII-His in 293T cell lysates. A) A Western blot probed with αHis was used to compare the concentration of CAII-His$_6$ in previously transfected 293T cell lysate to a purified CAII-His$_6$ standard, demonstrating that the concentration of CAII-His$_6$ in transfected cell lysate was greater than 200 nM. The blot was. B) Diluting the 293T cell lysate previously transfected with CAII-His$_6$ into untransfected lysate at a ratio of 1:100, approximating 3 nM expression of CAII-His$_6$, resulted in ~10-fold enrichment of the sequence corresponding to CA:GLCBS. C) Diluting CAII-His$_6$ transfected lysate 1:10 into untransfected lysate, approximating 30 nM CAII-His$_6$ expression, resulted in only weak enrichment of a sequence corresponding to CA:CBS. Together, these results are consistent with predictions made using a recent description of three-body binding.[3]

Figure 9G:
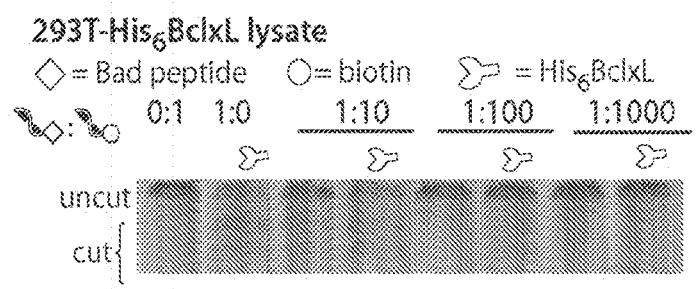

ISID using DNA-αHis also resulted in ~100-fold enrichment of a sequence corresponding to Bcl-xL:Bad ($K_d$=0.6 nM)[17] when performed in lysates of 293T cells transfected with a plasmid expressing His$_6$-Bcl-xL (truncated C-terminus, amino acids 1 to 212) (FIG. 9g). Taken together, these results suggest that ISID using the DNA-αHis antibody can enrich sequences corresponding to ligand:target combinations for unpurified targets in cell lysates.

Covalent protein-DNA linkages offer several potential advantages during ISID compared to non-covalent antibody-target or antibody-tag associations. It was hypothesized that formation of a covalent bond between a target protein and its identifying DNA might increase the stability of the DNA-target entity and the sensitivity of ISID for weaker small molecule-target binding interactions. In principle, replacing non-covalent antibody-target binding with a covalent linkage can be accomplished by expressing the target protein as a fusion to a self-labeling protein domain such as SNAP-tag,[18,19] CLIP-tag,[20] or HaloTag.[21] Moreover, the use of a small molecule-reactive tag removes the requirement for a non-covalent ternary complex to form, and therefore reduces the assay's dependence on target protein concentration.[15]

Finally, the small size of self-labeling proteins compared to antibodies (~30 kDa vs.~150 kDa) suggests that the former are less likely to obscure ligand-binding sites or disrupt native protein-protein interactions. Self-labeling proteins have been used successfully in protein-ligand binding assays[19,20] and in linking target proteins to DNA.[22] It was therefore hypothesized that self-labeling proteins expressed as fusions to target proteins might serve as effective reagents for linking targets to DNA during ISID.

Figure 10A:
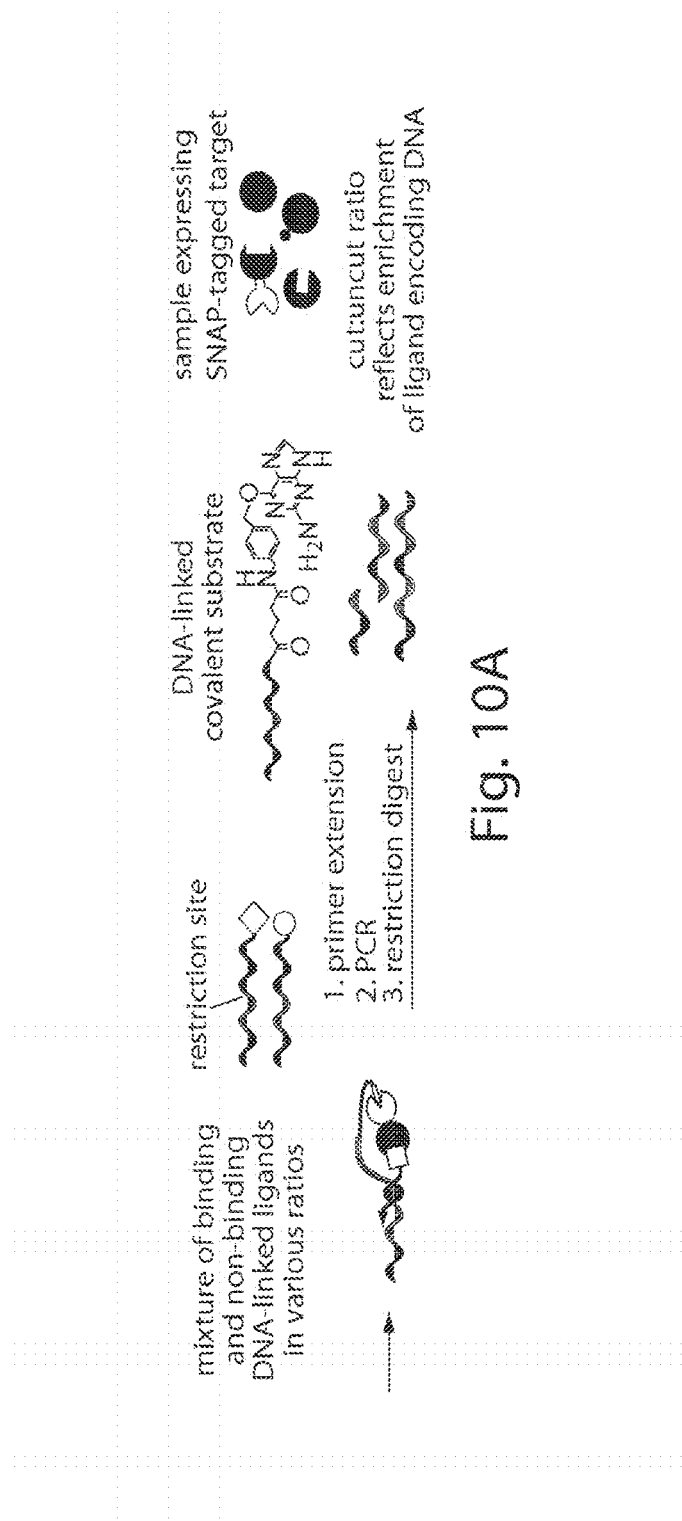

293T cells were transiently transfected with vectors expressing N- or C-terminally SNAP-tagged CAII (SNAP-CAII or CAII-SNAP). The resulting lysates were individually incubated with a SNAP substrate, $O^6$-benzylguanine (BG), linked to DNA (DNA-BG) for 15 minutes before incubation with mixtures of DNA-GLCBS/DNA-desthiobiotin or DNA-CBS/DNA-desthiobiotin. After ISID and restriction digestion, ~100-fold enrichment for the sequences encoding CAII:GLCBS and CAII:CBS was observed in samples expressing SNAP-CAII or CAII-SNAP, but not in untreated samples or samples expressing SNAP-tag alone (FIGS. 10b, 10d, and 21).

Similarly, ISID performed on 293T cell lysate expressing SNAP-Bcl-xL or Bcl-xL-SNAP with DNA-BG and mixtures of DNA-Bak/DNA-BakL78A/DNA-biotin resulted in ~100-fold enrichment of a sequence corresponding to Bcl-xL:Bak ($K_d$=340 nM)[23] but no enrichment of the DNA sequence encoding an interaction between Bcl-xL and the closely related negative control peptide BakL78A ($K_d$=270 μM)[23]. (FIGS. 10c, 10e, and 21). Collectively, these results demonstrate the ability of protein targets fused to self-labeling domains to participate in ISID. In contrast to our results with αHis-mediated ISID, it was noticed that both N- and C-terminally SNAP-tagged proteins resulted in roughly equivalent enrichment levels of DNA encoding known ligand-target pairs, suggesting that the SNAP-tag also offers increased generality compared to the His$_6$-tag:αHis approach.

FIG. 21 illustrates target compatibility with N- and C-terminal SNAP-tag fusions. A) ISID with 293T cell lysate expressing SNAP-CAII or CAII-SNAP resulted in ~100-fold enrichment of a sequence corresponding to GLCBS:CA. B) ISID with 293T cell lysate expressing with SNAP, FRB-SNAP, or FRB-SNAP and FKBP resulted in slightly stronger enrichment of the sequence corresponding to FRB:rapamycin in cells transfected with both FRB-SNAP and FKBP. C) ISID with 293T cell lysate expressing SNAP-Bcl-xL resulted in ~100-fold enrichment of a sequence corresponding to Bak:Bcl-xL, but no enrichment of a sequence corresponding to BakL78A:Bcl-xL, demonstrating that ISID selectively enriches DNA sequences conjugated to binding ligands over those conjugated to closely related molecules. D) When ISID was performed on lysate from 293T cells expressing SNAP, SNAP-Bcl-xL, or Bcl-xL-SNAP, samples containing SNAP-tagged Bcl-xL and DNA-linked Bad or Bak were amplified much more rapidly than samples containing SNAP alone or DNA-linked BakL78A ($\Delta C_T$=7-8 cycles). Together, these results suggest that the SNAP-tag approach enables ISID that is less dependent on target-tag orientation than His$_6$-tag approach.

The ability of ISID to evaluate ligand-protein binding in complex mixtures enables the detection of interactions that require exogenous factors. For example, the interaction of rapamycin with FRB, the rapamycin-binding domain of mTOR, is substantially increased in the presence of another rapamycin binding protein, FKBP; the $K_d$ of rapamycin:FRB is 26 μM, while the $K_d$ of FKBP•rapamycin:FRB is 12 nM.[24] It was investigated whether the FKBP-dependent modulation in the strength of the FRB:rapamycin interaction could be detected by ISID. Azide-linked rapamycin[24] was conjugated to DNA using the Cu(I)-catalyzed azide-alkyne cycloaddition reaction.[25]

Figure 10F:
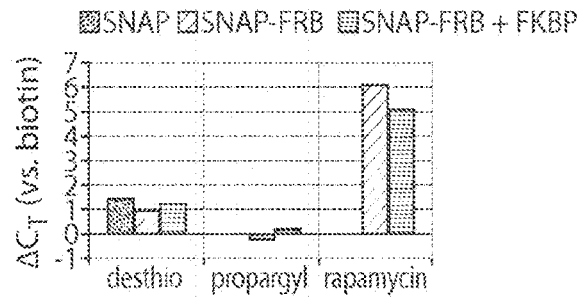
Figure 10G:
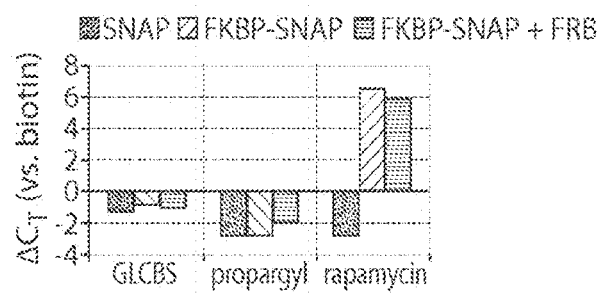
Figure 10H:
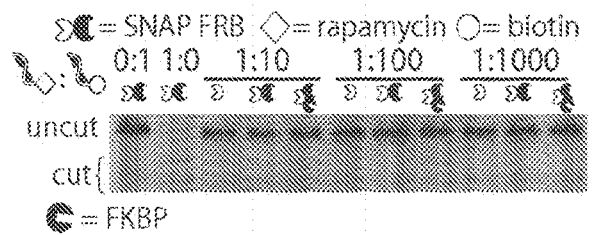
Figure 10I:
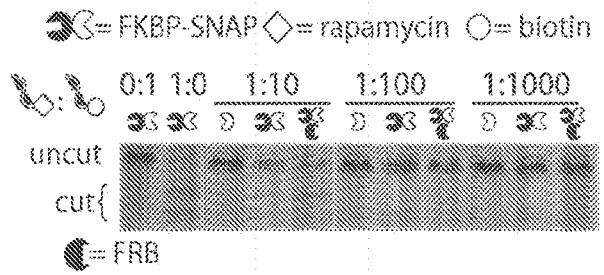

When ISID was performed using 293T cell lysates overexpressing SNAP, SNAP-FRB, or SNAP-FRB and FKBP, ~10-fold enrichment of the sequence corresponding to FRB:rapamycin in the sample overexpressing SNAP-FRB was observed, and a ~100-fold enrichment in the sample overexpressing SNAP-FRB and FKBP (FIGS. 10f and 10h). Similar results were obtained with recombinant, pre-conjugated DNA-FRB (FIG. 22). The rapamycin•FRB complex also has a higher affinity for FKBP ($K_d$~100 fM) than rapamycin alone ($K_d$~0.2 nM).[24] 293T cell lysate overexpressing FRB and FKBP-SNAP also showed ~10-fold greater enrichment for a sequence encoding FKBP:rapamycin than a sample overexpressing FKBP-SNAP alone (FIGS. 10g and 10i). Together these results demonstrate that ISID results can reflect the influence of accessory proteins on the target affinity of small-molecule ligands.

FIG. 22 illustrates that preincubating DNA-linked small molecules with FKBP increases enrichment for DNA-FRB. A) Pre-incubation of DNA-linked ligands with 100 nM, or 1 µM FKBP (final concentration: 10 nM or 100 nM FKBP with 10 nM DNA-linked ligand) resulted in a small increase $\Delta C_T$ value of rapamycin as compared to an IDPCR reaction with DNA-FRB, but lacking added FKBP. B) Although the difference in $\Delta C_T$ values was small, a ~10-fold increase in enrichment for the sequence corresponding to FRB:rapamycin was observed for a sample in which the mixture of DNA-rapamycin/DNA-desthiobiotin was preincubated with FKBP (each at 10 nM final concentration), suggesting that the signal obtained in IDPCR on directly linked targets can respond to the influence of accessory proteins.

Because a key advantage of ISID is the ability to simultaneously assay all interactions between combined libraries of targets and ligands in a single solution, the ability of ISID to selectively enrich known target:ligand interactions from a model library containing 262 DNA-linked ligands (comprising DNA-linked GLCBS, CBS, rapamycin, Bad, Bak, BakL78A and hexylamine linked to a set of 256 DNA sequences) and 259 DNA-linked targets was next tested. To generate a library of 259 DNA-linked targets, lysates from 293T cells previously transfected with vectors encoding SNAP-FKBP, SNAP-CA, SNAP-Bcl-xL, or SNAP were individually incubated with BG linked to unique DNA sequences (in the case of SNAP-FKBP, SNAP-CA, or SNAP-Bcl-xL) or to a library of 256 sequences (in the case of SNAP alone), quenched with a free BG derivative, and pooled to obtain an equimolar ratio of the 259 DNA-linked targets. As a control, aliquots of the same lysates were separately incubated with DNA sequences lacking conjugated BG.

Both samples were incubated with the library of DNA-linked ligands and processed by primer extension, PCR, and high-throughput DNA sequencing using conditions identified in previous experiments (FIGS. 13 and 17). The number of sequence counts for each protein:ligand sequence from the sample treated with DNA-BG was divided by the corresponding number of counts from the sample treated with DNA alone and observed enrichment factors from 68.9 to 328.7 for sequences corresponding to all five known ligand-target binding interactions including FKBP:rapamycin, CAII:GLCBS, CAII:CBS, Bcl-xL:Bad, and Bcl-xL:Bak (FIG. 11). The mean enrichment for all 67,858 possible ligand:target sequences was 1.5. Strong enrichment of the sequences corresponding to all of the known target:ligand interactions was observed, despite the fact that the corresponding dissociation constants vary over four orders of magnitude ($K_d$~0.2 nM-3.2 µM). No sequences corresponding to any presumed non-binding interactions were enriched greater than 31-fold and only 21 presumed false-positive sequences had enrichment factors greater than 20, a signal level less than one-third that of the weakest bona fide positive (Table 1 and 2).

TABLE 4

Enrichment factors for known target:ligand pairs from model selection with a library of DNA-linked small molecules and a library of cell lysates expressing SNAP-target fusions. Letter labels coincide with those on FIG. 11B.

| interaction | enrichment factor |
|---|---|
| A: FKBP + rapamycin | 100.6 |
| B: BclxL + Bad | 237.7 |
| C: BclxL + Bak | 68.9 |
| BclxL + BakL78A | 3.9 |
| D: CAII + GLCBS | 178.3 |
| E: CAII + CBS | 328.7 |
| mean | 1.5 |

TABLE 5

Sequences not known to correspond to a target:ligand pair are presumed false positives. Only one such presumed false positive had an enrichment factor greater than 30.

| enrichment factor | presumed false positives |
|---|---|
| 1.45 | 20360 |
| 5 | 2859 |
| 10 | 450 |
| 20 | 21 |
| 30 | 1 |

FIG. 13 illustrates a model library×library selection. Aspects of the primer extension in model library×library experiments were systematically investigated to identify primer extension conditions enabling enrichment of weaker interactions. A model library of protein targets containing DNA-SA, DNA-CAII and a 256-fold excess of DNA-GST linked to 256 different DNA sequences was incubated with a model small molecule library containing DNA-biotin, DNA-desthiobiotin, DNA-GLCBS and DNA-CBS with a 256-fold excess of DNA-hexylamine linked to 256 different DNA sequences. Enrichment factors for matching protein-ligand interactions are shown above. The mean enrichment of all sequences was generally less than 1.5. A) It was hypothesized that increasing the concentration of the combined target and ligand libraries would increase the fraction of bound targets and ligands but also increase intermolecular hybridization of DNA sequences not tethered by a noncovalent complex. Conversely, decreasing library concentrations would decrease protein-ligand binding and non-specific hybridization. It was found that a combined library concentration of 10 nM or 100 nM for each library resulted in the largest enrichment factors. B) Decreasing the concentration of dNTPs in the primer extension mixture decreased enrichment of lower affinity protein-ligand interactions. C) It was questioned whether higher temperatures during the primer extension reaction would decrease background signal due to intermolecular DNA hybridization or whether lower temperatures would increase signal by increasing the apparent $K_d$ of protein-ligand interactions. It was found that performing extension reactions at 37° C. resulted in the largest enrichment factors for known protein-ligand interactions. D) Enrichment of lower affinity target-ligand combinations improved as the concentration of Klenow exo⁻ was increased. Taken together, these results demonstrate that IDPCR experiments performed with 10 nM or 100 nM library concentration, 12.5 nM Klenow exo–, and 33 µM dNTPs at 37° C. resulted in the best enrichment factors for lower affinity ligand-target interactions.

FIG. 14 illustrates the effect of site of target labeling. It was investigated whether the site of DNA conjugation on the target protein affects the signal-to-noise ratio of IDPCR experiments on directly linked proteins. After removing the endogenous cysteine from CAII, generating CAII (C206S), and several clones with a single cysteine added at a solvent-exposed position[1] were generated (C206S/D19C), (C206S/D52C), (C206S/K213C), (C206S/K252C). The double mutants were expressed and purified before reduction with TCEP-agarose (Pierce) and labeling with DNA-amine using the SM(PEG)$_2$ heterobifunctional crosslinker (Pierce). After reaction, DNA-CAII conjugates were purified by size exclusion chromatography using a Superdex 75 10/300 column (GE Healthcare) on an Akta FPLC (Amersham). The resulting purified DNA-CAII conjugates were used in IDPCR experiments comparing the $\Delta C_T$ of DNA-GLCBS and DNA-amine. The position of DNA modification on carbonic anhydrase did not appear to strongly influence the $\Delta C_T$ value. Error bars represent standard deviation of three replicates.

FIG. 15 illustrates ISID with 6 nt complementary region and various polymerases. A) Complementary regions of library members not participating in binding and annealing interactions can be degraded by 3'-exonucleases, preventing them from contributing to background signal. B) The ability of Exo I and DNA polymerases with 3'-exonuclease activity to perform ISID on samples containing DNA-αSA, SA, and DNA-amine, DNA-GLCBS, or DNA-biotin with complementary regions of 6 bp was investigated. The signal-to-noise ratio of ISID using a 6-bp complementary region was not improved by 3'-exonuclease activity.

FIG. 16 illustrates optimization of ISI with 8 nt complementary region. The ability of polymerases with 3'-exonulcease activity to perform ISID with complementary regions longer than 6 bp was investigated. A) Using DNA sequences with an 8-bp complementary region, it was found that T4 DNA polymerase produced the largest $\Delta C_T$ values in ISID reactions performed with SA, DNA-αSA, and DNA-desthiobiotin or DNA-amine. B) Further increasing the 3'-exonuclease activity by adding Exo I to primer extension reactions with T4 DNA polymerase did not have a strong impact on the $\Delta C_T$ values. C) ISID reactions performed with Klenow exo⁻, 25 U Exo I, and 8-bp complementary regions recapitulated the results with T4 DNA polymerase, suggesting that the exonuclease activity of T4 DNA polymerase is responsible for the increased signal-to-noise ratio. D) While ISID using T4 DNA polymerase resulted in equivalent $\Delta C_T$ values with both 8-bp and 9-bp complementary regions, samples with longer complementary regions had lower $\Delta C_T$ values. Error bars represent the standard deviation of three replicates. Each of the three bars corresponds to a set of three replicates performed on a different day. Together these results suggest that the signal-to-noise ratio of ISID experiments is determined by the combination of complementary region length, DNA polymerase activity, and 3'-exonuclease activity.

FIG. 17 illustrates library×library screens with various polymerases. A series of library×library model selections were performed on combined model libraries of 261 DNA-linked small molecules, including DNA-linked biotin, desthiobiotin, iminobiotin, imino-biotin (SA-iminobiotin $K_d$=13 µM),[2] GLCBS and CBS, and 258 DNA-linked proteins, including SA and CA with either a 6-nt or 8-nt complementary region. Primer extension was performed with Klenow exo⁻, Klenow exo⁻ and Exo I, Klenow, DNA polymerase I, or T4 DNA polymerase on samples containing DNA-linked small molecules and DNA-linked proteins or DNA lacking linked proteins, as a control. After high throughput sequencing, enrichment factors for each of the known protein:ligand pairs was calculated and normalized to the enrichment in the results with Klenow exo⁻. Of the conditions tested, it was found that using model libraries with an 8-nt complementary region and performing the primer extension reaction with T4 DNA polymerase resulted in the largest increase in enrichment (4.5- to 140-fold) for protein:ligand pairs with affinities from 40 nM to 13 µM.

FIG. 18 illustrates competition of antibody with ligand binding. A) To investigate whether a polyclonal antibody against CAII (αCAII) competes with ligand binding, free αCAII or free GLCBS were added to an IDPCR reaction with DNA-CAII and DNA-GLCBS or DNA-amine. B) Addition of excess free GLCBS or free polyclonal αCAII result in similar decreases in the $\Delta C_T$ value between samples with DNA-GLCBS and DNA-amine, suggesting that the polyclonal antibody for CAII competes with ligand binding.

FIG. 19 illustrates ISID with DNA-linked antibodies and ligands. A) ISID experiments were performed on samples containing DNA-αHis, with recombinant His$_6$-CAII or CAII-His$_6$ or without added protein and with DNA-biotin, DNA-iminobiotin, DNA-GLCBS, or DNA-CBS. It was found that DNA from samples containing DNA-αHis, CAII-His$_6$ and DNA-GLCBS or DNA-CBS was amplified more quickly in qPCR than samples lacking CAII or containing His$_6$-CAII ($\Delta C_T$=2-3 cycles). Error bars represent the standard deviation of three replicates. B) ISID was next used with recombinant His$_6$-Bcl-xL and Bcl-xL-His$_6$. It was found that DNA from a sample containing DNA-αHis, His$_6$-Bcl-xL and DNA-Bad was more rapidly amplified than DNA from samples with Bcl-xL-His$_6$ or another DNA-linked small molecule ($\Delta C_T$=3 cycles). Error bars represent the standard deviation of three replicates. C) To investigate whether ISID using DNA-αHis and a His$_6$-tagged target enables enrichment of sequences corresponding to known binding ligands in cell lysate, recombinant CAII-His$_6$ was added to HeLa cell lysate (0.01% wt) and incubated with DNA-αHis and mixtures of DNA-GLCBS/DNA-biotin. An enrichment factor of about 100-fold was observed for the sequence corresponding to GLCBS:CA. This enrichment factor is about 10-fold greater than that from an ISID experiment performed with DNA-αCAII and CAII in HeLa cell lysate (0.01% wt) (FIG. 8).

When a similar ISID experiment was performed with 260 DNA-linked targets, including both SNAP-FKBP and FRB-SNAP, all of the known interactions except for that of FRB:rapamycin were observed, likely due to both the relatively weak affinity of rapamycin for FRB ($K_d$=26 µM),[24] and the relatively low expression level of FRB-SNAP (FIG. 23). In an ISID experiment containing FRB-SNAP but lacking SNAP-FKBP, 23.4-fold enrichment of the sequence corresponding to rapamycin:FRB was observed, with only three presumed false positive sequences enriched as strongly (FIG. 23). FIG. 23 illustrates a library×library experiment including FRB-SNAP. A) An ISID experiment containing 259 DNA-linked targets including SNAP-Bcl-xL, FRB-SNAP, and SNAP-CAII, together with 262 DNA-linked ligands, revealed strong enrichment of all known target: ligand interactions with affinities from 9 nM to 23 µM. A: BclxL:Bad, B: BclxL:Bak, C: FRB:rapamycin, D: CAII: GLCBS, E: CAII:CBS. B) Only three presumed false positives were enriched as strongly as the sequence corresponding to FRB:rapamycin. C) A western blot of lysates used in library×library ISID was stained with an anti-SNAP antibody (NEB), and demonstrates that the expression level of FRB-SNAP was substantially lower than expression of the other SNAP-tagged target proteins. Together, these results validate the ability of ISID to identify interactions between combined libraries of small molecules and SNAP-tagged target proteins in crude cell lysates.

Figure 11C:
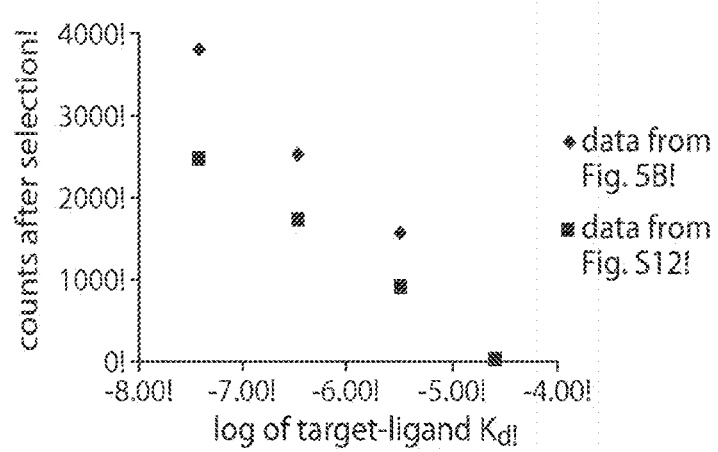

The relationship between target-ligand affinity and sequence counts following ISID should be governed by several factors including concentrations of individual library members, differences in the expression levels of SNAP-tagged targets, and differences in the extent to which both DNA-linked ligands and SNAP-tagged targets are obscured by factors present in the cell lysate. For example, 293T cells have been shown to natively express CAII,[26] BclxL,[27] FK506 binding proteins,[28] and mTor,[29] and these untagged targets may compete for ligand binding. Despite these potential complications, for interactions with affinities between Kd=40 nM to 26 µM, a surprisingly strong relationship between log(Kd) and the number of counts observed after selection was noted (FIGS. 11c and 24). In principle, this relationship can be used to estimate the detection limit of the ISID assay (here 30-60 µM; see FIG. 24b) and to infer the affinities of newly detected interactions.

FIG. 24 illustrates library×library raw sequence counts and relationship to $K_D$. A) Sequence counts after selection were plotted for all five known target-ligand interactions queried in the selections shown in FIGS. 11B and 23. B) A linear relationship was observed when the sequence counts for the ligand-target interactions with $K_d$~40 nM-26 µM were plotted against the logarithm of their affinities. Because the concentration of each library member in the 'selection' was 0.4 nM, it is possible that ligand-target pairs with Kd~0.2-0.6 nM (e.g., FKBP:rapamycin and BclxL:Bad) do not fit the linear trend because they reached binding saturation. Equations fit from this data could be used to estimate the limit of detection of ISID (x-intercept, here 30-60 µM) or to estimate the affinity of new interactions. C,D) Although the relationship between affinity and enrichment factor is not as linear as that between affinity and sequence counts, plotting the enrichment factor is useful in distinguishing true binding events from presumed false positives. In particular, plotting enrichment factors corrects for the DNA sequence bias in PCR and/or high throughput sequencing that likely causes the disproportionate number of counts observed for particular sequences in both the selection (D) and negative control samples (C).

Figure 24A:
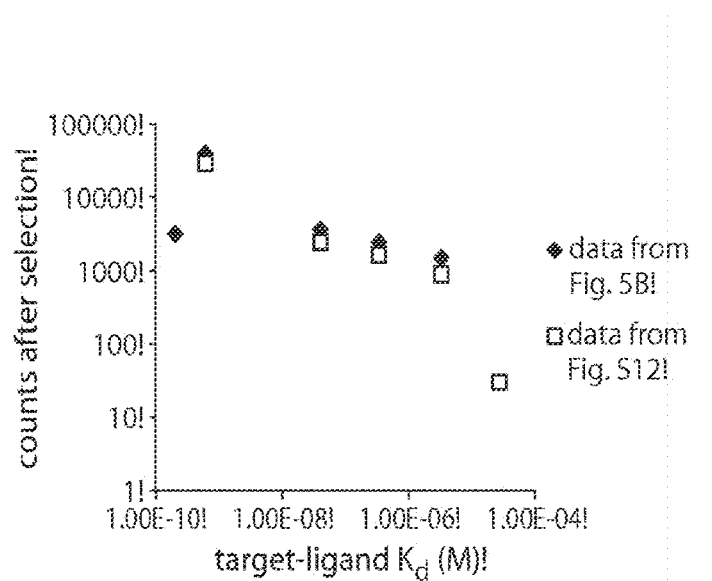
Figure 24B:
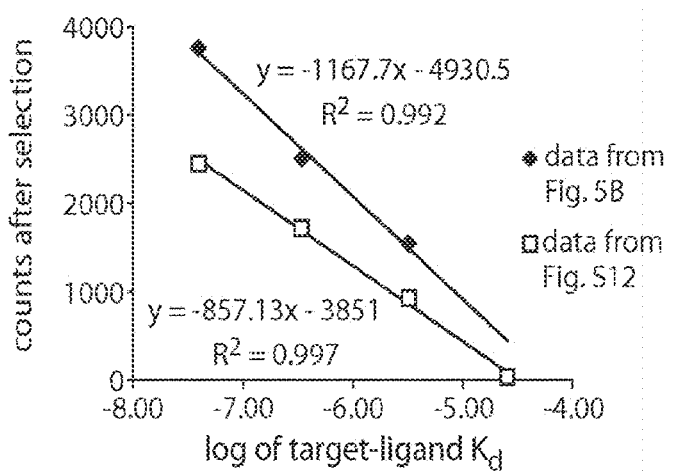
Figure 24C:
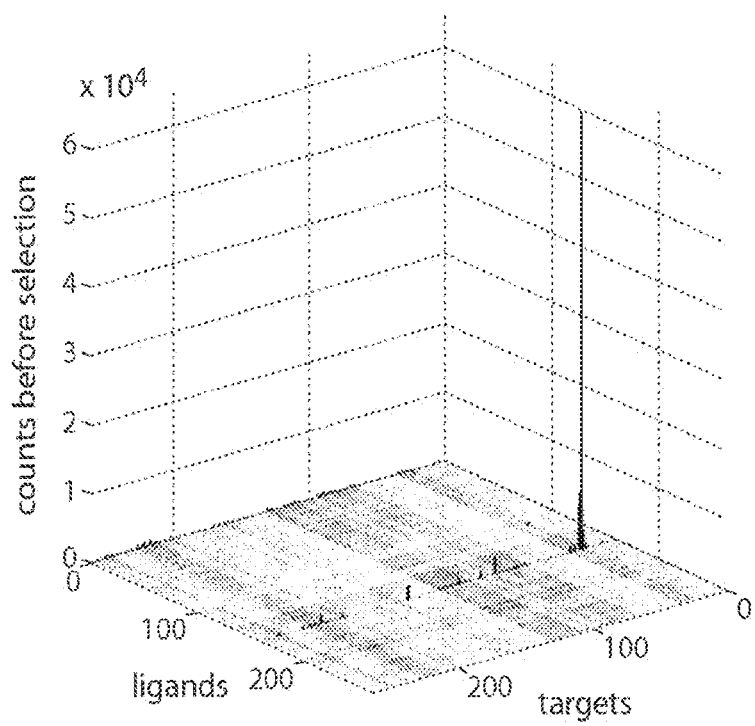
Figure 24D:
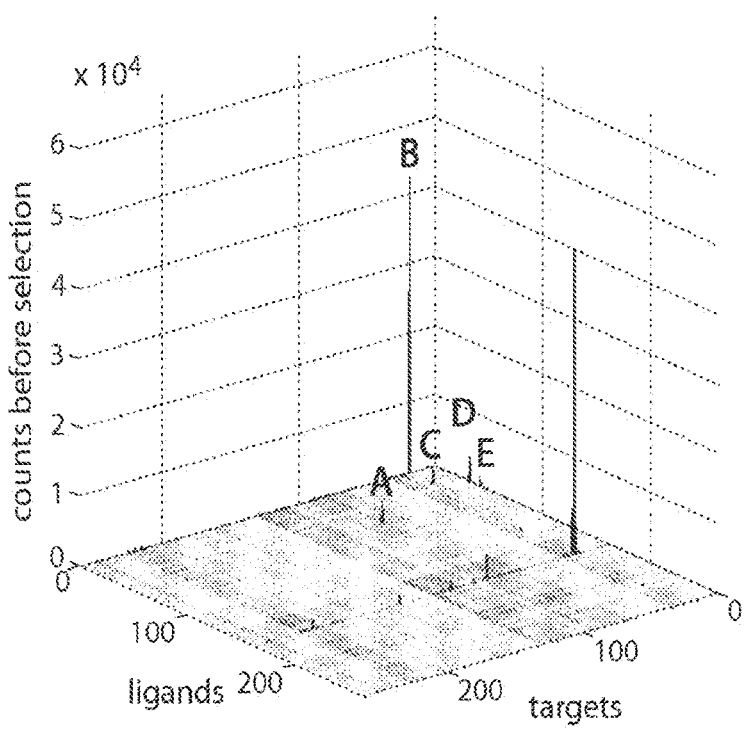

The relationship between affinity and enrichment factor was less strong than that between affinity and sequence counts. Enrichment factor values also depend on the number of sequence counts in the negative control sample, which are generally smaller (despite 12-18-fold sequence coverage) and more susceptible to variation caused by DNA sequence bias and sampling stochasticity during PCR or high throughput sequencing. Plotting enrichment factors is, however, an effective way to distinguish true binding events from presumed false positives by eliminating sequences likely amplified due to PCR bias (FIG. 24c, d). Interactions with $K_d$~0.2-0.6 nM did not follow the linear trend (FIG. 24a). A plausible explanation for this observation is that the concentration of each library member during ISID is 0.4 nM, and thus interactions with affinities in this range (here, FKBP:rapamycin and Bcl-xL:Bad) could approach binding saturation.

Discussion

ISID is a method for rapidly evaluating potential small molecule-target interactions from mixtures in a single solution that is compatible with unpurified targets in biological samples. The ability to identify ligand:target pairs from complex samples including cell lysates offers significant advantages compared to other methods for evaluating DNA-encoded chemical libraries. Samples in cell lysates are able to undergo native post-translational modification and interact with accessory proteins and metabolites in ways that better reflect their relevant biological environment. Because ISID is compatible with crude cell lysates, difficult-to-purify, poorly soluble, intrinsically unstable, and aggregation-prone targets may also be compatible with this method, without requiring truncation or other strategies used to promote heterologous expression. The ability of ISID to selectively amplify DNA sequences corresponding to interactions between $His_6$-tagged or SNAP-tagged target proteins and their ligands in cell lysates was demonstrated, and it was also shown that ISID results reflect the ability of accessory proteins to modulate ligand-target affinity. In addition, the ability of ISID to selectively enrich DNA sequences corresponding to known ligand:target interactions with affinities from 0.2 nM to 26 µM from a library of SNAP-target expressing cell lysates and a library of DNA-linked small molecules was demonstrated. Moreover, a relationship between sequence counts and ligand-target identity was observed, suggesting that ISID sequencing results may be able to not only identify new interactions but also estimate their affinities. ISID provides a general and highly efficient strategy to evaluate DNA-encoded libraries under conditions in which purified protein targets are unavailable or differ in important ways from their native cellular counterparts.

REFERENCES (1) reviewed in: a) Kleiner, R. E.; Dumelin, C. E.; Liu, D. R. Chem. Soc. Rev. 2011, 40, 5707. b) Mannocci, L.; Leimbacher, M.; Wichert, M.; Scheuermann, J.; Neri, D. Chem. Commun. 2011, 47, 12747. c) Clark, M. A. Curr. Opin. Chem. Biol. 2010, 14, 396.

(2) a) Buller, F.; Steiner, M.; Frey, K.; Mircsof, D.; Scheuermann, J.; Kalisch, M.; Buhlmann, P.; Supuran, C. T.; Neri, D. ACS Chem. Biol. 2011, 6, 336. b) Kleiner, R. E.; Dumelin, C. E.; Tiu, G. C.; Sakurai, K.; Liu, D. R. J. Am. Chem. Soc. 2010, 132, 11779. c) Clark, M. A.; Acharya, R. A.; Arico-Muendel, C. C.; Belyanskaya, S. L.; Benjamin, D. R.; Carlson, N. R.; Centrella, P. A.; Chiu, C. H.; Creaser, S. P.; Cuozzo, J. W.; Davie, C. P.; Ding, Y.; Franklin, G. J.; Franzen, K. D.; Gefter, M. L.; Hale, S. P.; Hansen, N. J.; Israel, D. I.; Jiang, J.; Kavarana, M. J.; Kelley, M. S.; Kollmann, C. S.; Li, F.; Lind, K.; Mataruse, S.; Medeiros, P. F.; Messer, J. A.; Myers, P.; O'Keefe, H.; Oliff, M. C.; Rise, C. E.; Satz, A. L.; Skinner, S. R.; Svendsen, J. L.; Tang, L.; van Vloten, K.; Wagner, R. W.; Yao, G.; Zhao, B.; Morgan, B. A. Nat. Chem. Biol. 2009, 5, 647. d) Wrenn, S. J.; Weisinger, R. M.; Halpin, D. R.; Harbury, P. B. J. Am. Chem. Soc. 2007, 129, 13137.

(3) McGregor, L. M.; Gorin, D. J.; Dumelin, C. E.; Liu, D. R. J. Am. Chem. Soc. 2010, 132, 15522.

(4) a) Inglese, J.; Johnson, R. L.; Simeonov, A.; Xia, M.; Zheng, W.; Austin, C. P.; Auld, D. S. Nat. Chem. Biol.

2007, 3, 466. b) Scott, D. E.; Coyne, A. G.; Hudson, S. A.; Abell, C. Biochemistry 2012, 51, 4990.
(5) Good, M. C.; Zalatan, J. G.; Lim, W. A. Science 2011, 332, 680.
(6) a) Fredriksson, S.; Gullberg, M.; Jarvius, J.; Olsson, C.; Pietras, K.; Gustafsdottir, S. M.; Ostman, A.; Landegren, U. Nat. Biotechnol. 2002, 20, 473. b) Soderberg, O.; Gullberg, M.; Jarvius, M.; Ridderstrale, K.; Leuchowius, K. J.; Jarvius, J.; Wester, K.; Hydbring, P.; Bahram, F.; Larsson, L. G.; Landegren, U. Nat. Methods 2006, 3, 995. c) Hammond, M.; Nong, R. Y.; Ericsson, O.; Pardali, K.; Landegren, U. PLoS One 2012, 7, e40405. d) Gustafsdottir, S. M.; Wennstrom, S.; Fredriksson, S.; Schallmeiner, E.; Hamilton, A. D.; Sebti, S. M.; Landegren, U. Clin. Chem. 2008, 54, 1218.
(7) Lundberg, M.; Eriksson, A.; Tran, B.; Assarsson, E.; Fredriksson, S. Nucleic Acids Res. 2011, 39, e102.
(8) Dumelin, C. E.; Scheuermann, J.; Melkko, S.; Neri, D. Bioconjugate Chem. 2006, 17, 366.
(9) Green, N. M. Methods Enzymol. 1990, 184, 51.
(10) Schwanhausser, B.; Busse, D.; Li, N.; Dittmar, G.; Schuchhardt, J.; Wolf, J.; Chen, W.; Selbach, M. Nature 2011, 437, 337.
(11) Wang, F.; Travins, J.; DeLaBarre, B.; Penard-Lacronique, V.; Schalm, S.; Hansen, E.; Straley, K.; Kernytsky, A.; Liu, W.; Gliser, C.; Yang, H.; Gross, S.; Artin, E.; Saada, V.; Mylonas, E.; Quivoron, C.; Popovici-Muller, J.; Saunders, J. O.; Salituro, F. G.; Yan, S.; Murray, S.; Wei, W.; Gao, Y.; Dang, L.; Dorsch, M.; Agresta, S.; Schenkein, D. P.; Biller, S. A.; Su, S. M.; de Botton, S.; Yen, K. E. Science 2013, 340, 622.
(12) Mincione, F.; Starnotti, M.; Menabuoni, L.; Scozzafava, A.; Casini, A.; Supuran, C. T. Bioorg. Med. Chem. Lett. 2001, 11, 1787.
(13) Fritze, C. E.; Anderson, T. R. Methods Enzymol. 2000, 327, 3.
(14) Qiagen 2002; Vol. 2013.
(15) Douglass, E. F., Jr.; Miller, C. J.; Sparer, G.; Shapiro, H.; Spiegel, D. A. J. Am. Chem. Soc. 2013, 135, 6092.
(16) West, G. M.; Tang, L.; Fitzgerald, M. C. Anal. Chem. 2008, 80, 4175.
(17) Petros, A. M.; Nettesheim, D. G.; Wang, Y.; Olejniczak, E. T.; Meadows, R. P.; Mack, J.; Swift, K.; Matayoshi, E. D.; Zhang, H.; Thompson, C. B.; Fesik, S. W. Protein Sci. 2000, 9, 2528.
(18) Mollwitz, B.; Brunk, E.; Schmitt, S.; Pojer, F.; Bannwarth, M.; Schiltz, M.; Rothlisberger, U.; Johnsson, K. Biochemistry 2012, 51, 986.
(19) Chidley, C.; Haruki, H.; Pedersen, M. G.; Muller, E.; Johnsson, K. Nat. Chem. Biol. 2011, 7, 375.
(20) Haruki, H.; Gonzalez, M. R.; Johnsson, K. PLoS One 2012, 7, e37598.
(21) Encell, L. P.; Friedman Ohana, R.; Zimmerman, K.; Otto, P.; Vidugiris, G.; Wood, M. G.; Los, G. V.; McDougall, M. G.; Zimprich, C.; Karassina, N.; Learish, R. D.; Hurst, R.; Hartnett, J.; Wheeler, S.; Stecha, P.; English, J.; Zhao, K.; Mendez, J.; Benink, H. A.; Murphy, N.; Daniels, D. L.; Slater, M. R.; Urh, M.; Darzins, A.; Klaubert, D. H.; Bulleit, R. F.; Wood, K. V. Curr. Chem. Genomics 2012, 6, 55.
(22) a) Niemeyer, C. M. Angew. Chem. Int. Ed. Engl. 2010, 49, 1200. b) Sacca, B.; Meyer, R.; Erkelenz, M.; Kiko, K.; Arndt, A.; Schroeder, H.; Rabe, K. S.; Niemeyer, C. M. Angew. Chem. Int. Ed. Engl. 2010, 49, 9378.
(23) Sattler, M.; Liang, H.; Nettesheim, D.; Meadows, R. P.; Harlan, J. E.; Eberstadt, M.; Yoon, H. S.; Shuker, S. B.; Chang, B. S.; Minn, A. J.; Thompson, C. B.; Fesik, S. W. Science 1997, 275, 983.
(24) Banaszynski, L. A.; Liu, C. W.; Wandless, T. J. J. Am. Chem. Soc. 2005, 127, 4715.
(25) El-Sagheer, A. H.; Brown, T. Chem. Soc. Rev. 2010, 39, 1388.
(26) Sterling, D.; Brown, N. J.; Supuran, C. T.; Casey, J. R. Am. J. Physiol. Cell Physiol. 2002, 283, C1522.
(27) Pradhan, A. K.; Mohapatra, A. D.; Nayak, K. B.; Chakraborty, S. PLoS One 2011, 6, e25370.
(28) Gelman, J. S.; Sironi, J.; Berezniuk, I.; Dasgupta, S.; Castro, L. M.; Gozzo, F. C.; Ferro, E. S.; Fricker, L. D. PLoS One 2013, 8, e53263.
(29) Sarbassov, D. D.; Ali, S. M.; Sengupta, S.; Sheen, J. H.; Hsu, P. P.; Bagley, A. F.; Markhard, A. L.; Sabatini, D. M. Molecular cell 2006, 22, 159.

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the invention encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A method for determination of an in situ interaction between a candidate ligand and a target molecule, the method comprising:
(i) providing a plurality of nucleic acid templates, wherein each nucleic acid template comprises:
a first primer hybridization site;
a sequence tag;
a second primer hybridization site; and
a candidate ligand;
wherein the candidate ligand of any specific nucleic acid template is identified by its sequence tag;
(ii) contacting the nucleic acid templates with a target molecule and with a first primer comprising:
a sequence complementary to the first primer hybridization site,
a third primer hybridization site, and
a binding moiety that binds to the target molecule;
(iii) incubating the nucleic acid templates contacted with the target molecule and the first primer under conditions suitable for the candidate ligand and the binding moiety to bind to the target molecule;
(iv) incubating the nucleic acid templates contacted with the target molecule and the first primer under conditions suitable for the first primer bound to the nucleic acid template via a [candidate ligand]:[target molecule]:[binding moiety] interaction to hybridize with the first primer hybridization site of the nucleic acid template it is bound to for primer extension;
(v) contacting the nucleic acid templates contacted with the target molecule and the first primer with a PCR primer complementary to the second primer hybridization site and a PCR primer complementary to the third primer hybridization site, or a PCR primer complementary to the second and the third primer hybridization site; and
(vi) performing a polymerase chain reaction (PCR) to amplify a nucleic acid template sequence tag identifying a candidate ligand able to bind to the target molecule;
wherein the target molecule of (ii) is contacted with the nucleic acid templates of (i) in the presence of accessory molecules and metabolites that are present in a cell expressing the target molecule.

2. The method of claim 1, wherein the target molecule is a protein.

3. The method of claim 1, wherein the binding moiety of step (ii) binds to the target molecule via a non-covalent interaction.

4. The method of claim 3, wherein the binding moiety of step (ii) comprises an antibody or an antigen-binding antibody fragment.

5. The method of claim 3, wherein the binding moiety of step (ii) comprises a ligand or a receptor domain.

6. The method of claim 1, wherein the binding moiety covalently binds the target molecule.

7. The method of claim 6, wherein the target molecule comprises a reactive tag, and wherein the binding moiety reacts with the reactive tag thus covalently binding the first primer to the target molecule.

8. The method of claim 7, wherein the reactive tag is a self-labeling tag.

9. The method of claim 1, further comprising contacting the nucleic acid templates contacted with the target molecule and the first primer with a 3'-exonuclease.

10. The method of claim 1, wherein step (iv) comprises contacting the nucleic acid templates contacted with the target molecule and the first primer with a polymerase.

11. The method of claim 1 further comprising:
(vii) identifying the nucleic acid template sequence tag amplified in step (vi).

12. The method of claim 11 further comprising:
(viii) identifying the candidate ligand associated with the sequence tag identified in step (vii) by the nucleic acid sequence of the sequence tag.

13. The method of claim 1 further comprising:
(ix) identifying the first primer sequence tag amplified in step (vi).

14. The method of claim 13 further comprising:
(x) identifying the candidate binding molecule associated with the sequence tag identified in step (ix).

15. The method of claim 1, wherein the second and the third primer hybridization site are the same nucleic acid sequence.

16. The method of claim 1, wherein the PCR primer complementary to the second primer hybridization site and the PCR primer complementary to the third primer hybridization site are the same nucleic acid sequence.

17. The method of claim 1, wherein the second and the third primer hybridization site are different nucleic acid sequences.

18. The method of claim 1, wherein the first primer hybridization site and the third primer hybridization site overlap or are identical.

19. The method of claim 1, wherein the candidate ligand is selected from the group consisting of peptides, nucleic acids, and small organic compounds.

20. The method of claim 1, wherein the binding between the candidate ligand and the target molecule is characterized by a $K_D<10^{-6}$.

21. The method of claim 1, wherein the conditions suitable for hybridization of the nucleic acid sequence complementary to the first primer hybridization site to the first primer hybridization site and primer extension are conditions not allowing for efficient primer site hybridization and primer extension of first primer not connected to a nucleic acid template by a candidate ligand:target molecule interaction characterized by a $K_D<10^{-6}$.

22. A method for determination of an in situ interaction between a candidate ligand and a target molecule, the method comprising:
(i) providing a plurality of nucleic acid templates, wherein each nucleic acid template comprises:
a first primer hybridization site;
a sequence tag;
a second primer hybridization site; and
a candidate ligand;
wherein the candidate ligand of any specific nucleic acid template is identified by its sequence tag;
(ii) contacting the nucleic acid templates with a target molecule and with a first primer comprising:
a sequence complementary to the first primer hybridization site,
a third primer hybridization site, and
a binding moiety that binds to the target molecule;
(iii) incubating the nucleic acid templates contacted with the target molecule and the first primer under conditions suitable for the candidate ligand and the binding moiety to bind to the target molecule;
(iv) incubating the nucleic acid templates contacted with the target molecule and the first primer under conditions suitable for the first primer bound to the nucleic acid template via a [candidate ligand]: [target molecule]:[binding moiety] interaction to hybridize with the first primer hybridization site of the nucleic acid template it is bound to for primer extension;

(v) contacting the nucleic acid templates contacted with the target molecule and the first primer with a PCR primer complementary to the second primer hybridization site and a PCR primer complementary to the third primer hybridization site, or a PCR primer complementary to the second and the third primer hybridization site; and (vi) performing a polymerase chain reaction (PCR) to amplify a nucleic acid template sequence tag identifying a candidate ligand able to bind to the target molecule;

wherein the target molecule of (ii) is contacted with the nucleic acid templates of (i) in a cell lysate or in the presence of a cell lysate.

23. The method of claim 22, wherein the target molecule is a protein.

24. The method of claim 22, wherein the binding moiety of step (ii) binds to the target molecule via a non-covalent interaction.

25. The method of claim 22, wherein the binding moiety of step (ii) comprises an antibody or an antigen-binding antibody fragment.

26. The method of claim 22, wherein the binding moiety of step (ii) comprises a ligand or a receptor domain.

27. The method of claim 22, wherein the binding moiety covalently binds the target molecule.

28. The method of claim 27, wherein the target molecule comprises a reactive tag, and wherein the binding moiety reacts with the reactive tag thus covalently binding the first primer to the target molecule.

29. The method of claim 28, wherein the reactive tag is a self-labeling tag.

30. The method of claim 22, further comprising contacting the nucleic acid templates contacted with the target molecule and the first primer with a 3'-exonuclease.

31. The method of claim 22, wherein step (iv) comprises contacting the nucleic acid templates contacted with the target molecule and the first primer with a polymerase.

32. The method of claim 22 further comprising:
(vii) identifying the nucleic acid template sequence tag amplified in step (vi).

33. The method of claim 32 further comprising:
(viii) identifying the candidate ligand associated with the sequence tag identified in step (vii) by the nucleic acid sequence of the sequence tag.

34. The method of claim 22 further comprising:
(ix) identifying the first primer sequence tag amplified in step (vi).

35. The method of claim 34 further comprising:
(x) identifying the candidate binding molecule associated with the sequence tag identified in step (ix).

36. The method of claim 22, wherein the second and the third primer hybridization site are the same nucleic acid sequence.

37. The method of claim 22, wherein the PCR primer complementary to the second primer hybridization site and the PCR primer complementary to the third primer hybridization site are the same nucleic acid sequence.

38. The method of claim 22, wherein the second and the third primer hybridization site are different nucleic acid sequences.

39. The method of claim 22, wherein the first primer hybridization site and the third primer hybridization site overlap or are identical.

40. The method of claim 22, wherein the candidate ligand is selected from the group consisting of peptides, nucleic acids, and small organic compounds.

41. The method of claim 22, wherein the binding between the candidate ligand and the target molecule is characterized by a $K_D<10^{-6}$.

42. The method of claim 22, wherein the conditions suitable for hybridization of the nucleic acid sequence complementary to the first primer hybridization site to the first primer hybridization site and primer extension are conditions not allowing for efficient primer site hybridization and primer extension of first primer not connected to a nucleic acid template by a candidate ligand:target molecule interaction characterized by a $K_D<10^{-6}$.

* * * * *

SEQUENCE LISTING

```
<160> NUMBER OF SEQ ID NOS: 157

<210> SEQ ID NO 1
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1

Gly Leu Asn Asp Ile Phe Glu Ala Gln Lys Ile Glu Trp His Glu
1               5                   10                  15

<210> SEQ ID NO 2
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 2

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 3
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 3

Asp Tyr Lys Asp Asp Asp Asp Lys
1               5

<210> SEQ ID NO 4
<211> LENGTH: 9
<212> TYPE: PRT
<213> ORGANISM: Artificial Sequence
```

```
<220> FEATURE:
<223> OTHER INFORMATION: Synthetic Polypeptide

<400> SEQUENCE: 4

Tyr Pro Tyr Asp Val Pro Asp Tyr Ala
1               5

<210> SEQ ID NO 5
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 5

Glu Gln Lys Leu Ile Ser Glu Glu Asp Leu
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 6

Lys Glu Thr Ala Ala Ala Lys Phe Glu Arg Gln His Met Asp Ser
1               5                   10                  15

<210> SEQ ID NO 7
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 7

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 8
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 8

Ser Leu Ala Glu Leu Leu Asn Ala Gly Leu Gly Gly Ser
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 9

Trp Ser His Pro Gln Phe Glu Lys
1               5
```

<210> SEQ ID NO 10
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 10

Gly Lys Pro Ile Pro Asn Pro Leu Leu Gly Leu Asp Ser Thr
1               5                   10

<210> SEQ ID NO 11
<211> LENGTH: 32
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: modified by /5'carboxy//sp18/

<400> SEQUENCE: 11
cggcgatcgt gaaggaggct agcctgagtg ag                                 32

<210> SEQ ID NO 12
<211> LENGTH: 41
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (41)..(41)
<223> OTHER INFORMATION: modified by /sp18//sp18//3'aminoC6/

<400> SEQUENCE: 12
tggatcgtga tgactgtccc gacaagcata cgtatctcac t                       41

<210> SEQ ID NO 13
<211> LENGTH: 41
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (41)..(41)
<223> OTHER INFORMATION: modified by /sp18//sp18//3'aminoC6/GLCBS/

<400> SEQUENCE: 13
tggatcgtga tgactgtccc gacaagcata cgtatctcac t                       41

<210> SEQ ID NO 14
<211> LENGTH: 41
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (41)..(41)
<223> OTHER INFORMATION: modified by /sp18//sp18//3'biotinTEG/

<400> SEQUENCE: 14
tggatcgtga tgactgtccc gacaagcata cgtatctcac t                       41

<210> SEQ ID NO 15

```
<211> LENGTH: 41
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (41)..(41)
<223> OTHER INFORMATION: modified by /sp18//sp18//3'biotinTEG//
      desthiobiotin/

<400> SEQUENCE: 15
tggatcgtga tgactgtccc gacaagcata cgtatctcac t                41

<210> SEQ ID NO 16
<211> LENGTH: 41
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (41)..(41)
<223> OTHER INFORMATION: modified by /sp18//sp18//3'aminoC6//GLCBS/

<400> SEQUENCE: 16
tggatcgtga tgactgtccc gacaaggatc cgtatctcac t                41

<210> SEQ ID NO 17
<211> LENGTH: 41
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (41)..(41)
<223> OTHER INFORMATION: modified by /sp18//sp18//3'aminoC6/

<400> SEQUENCE: 17
tggatcgtga tgactgtccc gacaaccatg ggtatctcac t                41

<210> SEQ ID NO 18
<211> LENGTH: 41
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (41)..(41)
<223> OTHER INFORMATION: modified by /sp18//sp18//3'aminoC6//
      desthiobiotin/

<400> SEQUENCE: 18
tggatcgtga tgactgtccc gacaaccatg ggtatctcac t                41

<210> SEQ ID NO 19
<211> LENGTH: 41
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (27)..(30)
<223> OTHER INFORMATION: n is a, c, g, or t
<220> FEATURE:
<221> NAME/KEY: misc_feature
<222> LOCATION: (41)..(41)
<223> OTHER INFORMATION: modified by /sp18//sp18//3'aminoC6/
```

<400> SEQUENCE: 19
tggatcgtga tgactgtccc gacaatnnnn agtatctcac t            41

<210> SEQ ID NO 20
<211> LENGTH: 41
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (41)..(41)
<223> OTHER INFORMATION: modified by /sp18//sp18//3'aminoC6//CBS/

<400> SEQUENCE: 20
tggatcgtga tgactgtccc gacaagctta cgtatctcac t            41

<210> SEQ ID NO 21
<211> LENGTH: 41
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (41)..(41)
<223> OTHER INFORMATION: modified by /sp18//sp18//3'aminoC6//
      iminobiotin/

<400> SEQUENCE: 21
tggatcgtga tgactgtccc gacaagcata cgtatctcac t            41

<210> SEQ ID NO 22
<211> LENGTH: 32
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: modified by /5'carboxy//sp18/
<220> FEATURE:
<221> NAME/KEY: misc_feature
<222> LOCATION: (20)..(23)
<223> OTHER INFORMATION: n is a, c, g, or t

<400> SEQUENCE: 22
cggcgatcgt gaaggaggan nnnttgagtg ag                      32

<210> SEQ ID NO 23
<211> LENGTH: 43
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (43)..(43)
<223> OTHER INFORMATION: modified by /sp18//sp18//3'biotinTEG/

<400> SEQUENCE: 23
tggatcgtga tgactgtccc gacaagcata cgtatctcac tca          43

<210> SEQ ID NO 24
<211> LENGTH: 43
<212> TYPE: DNA
<213> ORGANISM: Artificial Sequence

```
<220> FEATURE:
<223> OTHER INFORMATION: Synthetic Polynucleotide
<220> FEATURE:
<221> NAME/KEY: misc_feature
<222> LOCATION: (43)..(43)
<223> OTHER INFORMATION: modified by /sp18//sp18//3'aminoC6/

<400> SEQUENCE: 24
tggatcgtga tgactgtccc gacaaccatg ggtatctcac tca                 43

<210> SEQ ID NO 25
<211> LENGTH: 43
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (43)..(43)
<223> OTHER INFORMATION: modified by /sp18//sp18//3'aminoC6//
      desthiobiotin/

<400> SEQUENCE: 25
tggatcgtga tgactgtccc gacaaccatg ggtatctcac tca                 43

<210> SEQ ID NO 26
<211> LENGTH: 44
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (44)..(44)
<223> OTHER INFORMATION: modified by /sp18//sp18//3'aminoC6/

<400> SEQUENCE: 26
tggatcgtga tgactgtccc gacaagcata cgtatctcac tcag                44

<210> SEQ ID NO 27
<211> LENGTH: 44
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (44)..(44)
<223> OTHER INFORMATION: modified by /sp18//sp18//3'aminoC6//
      desthiobiotin/

<400> SEQUENCE: 27
tggatcgtga tgactgtccc gacaagcata cgtatctcac tcag                44

<210> SEQ ID NO 28
<211> LENGTH: 45
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (45)..(45)
<223> OTHER INFORMATION: modified by /sp18//3'aminoC6/

<400> SEQUENCE: 28
tggatcgtga tgactgtccc gacaagcata cgtatctcac tcagt               45

<210> SEQ ID NO 29
```

```
<211> LENGTH: 45
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (45)..(45)
<223> OTHER INFORMATION: modified by /sp18//sp18//3'biotinTEG/

<400> SEQUENCE: 29
tggatcgtga tgactgtccc gacaagcata cgtatctcac tcagt            45

<210> SEQ ID NO 30
<211> LENGTH: 46
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (46)..(46)
<223> OTHER INFORMATION: modified by /sp18//sp18//3'aminoC6/

<400> SEQUENCE: 30
tggatcgtga tgactgtccc gacaagcata cgtatctcac tcagtc           46

<210> SEQ ID NO 31
<211> LENGTH: 46
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (46)..(46)
<223> OTHER INFORMATION: modified by /sp18//sp18//3'aminoC6//
      desthiobiotin/

<400> SEQUENCE: 31
tggatcgtga tgactgtccc gacaagcata cgtatctcac tcagtc           46

<210> SEQ ID NO 32
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 32

Ala Pro Gly Phe Ala
1               5

<210> SEQ ID NO 33
<211> LENGTH: 43
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (43)..(43)
<223> OTHER INFORMATION: modified by /sp18//sp18//3'aminoC6//GLCBS/

<400> SEQUENCE: 33
tggatcgtga tgactgtccc gacaaccatg ggtatctcac tca              43

<210> SEQ ID NO 34
<211> LENGTH: 43
```

```
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (43)..(43)
<223> OTHER INFORMATION: modified by /sp18//sp18//3'aminoC6/

<400> SEQUENCE: 34
tggatcgtga tgactgtccc gacaaaccgg tgtatctcac tca        43

<210> SEQ ID NO 35
<211> LENGTH: 43
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (43)..(43)
<223> OTHER INFORMATION: modified by /sp18//sp18//3'aminoC6/

<400> SEQUENCE: 35
tggatcgtga tgactgtccc gacaacaatt ggtatctcac tca        43

<210> SEQ ID NO 36
<211> LENGTH: 43
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (27)..(30)
<223> OTHER INFORMATION: n is a, c, g, or t
<220> FEATURE:
<221> NAME/KEY: misc_feature
<222> LOCATION: (43)..(43)
<223> OTHER INFORMATION: modified by /sp18//sp18//3'aminoC6/

<400> SEQUENCE: 36
tggatcgtga tgactgtccc gacaatnnnn agtatctcac tca        43

<210> SEQ ID NO 37
<211> LENGTH: 43
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (43)..(43)
<223> OTHER INFORMATION: modified by /sp18//sp18//3'aminoC6/

<400> SEQUENCE: 37
tggatcgtga tgactgtccc gacaacagct ggtatctcac tca        43

<210> SEQ ID NO 38
<211> LENGTH: 43
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (43)..(43)
<223> OTHER INFORMATION: modified by /sp18//sp18//3'aminoC6//CBS/

<400> SEQUENCE: 38
```
tggatcgtga tgactgtccc gacaaaccgg tgtatctcac tca                   43

<210> SEQ ID NO 39
<211> LENGTH: 43
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (43)..(43)
<223> OTHER INFORMATION: modified by /sp18//sp18//3'aminoC6//
      iminobiotin/

<400> SEQUENCE: 39
tggatcgtga tgactgtccc gacaacaatt ggtatctcac tca                   43

<210> SEQ ID NO 40
<211> LENGTH: 43
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (43)..(43)
<223> OTHER INFORMATION: modified by /sp18//sp18//3'aminoC6//GLCBS/

<400> SEQUENCE: 40
tggatcgtga tgactgtccc gacaacagct ggtatctcac tca                   43

<210> SEQ ID NO 41
<211> LENGTH: 43
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (43)..(43)
<223> OTHER INFORMATION: modified by /sp18//sp18//3'aminoC6//GLCBS/

<400> SEQUENCE: 41
tggatcgtga tgactgtccc gacaagaatt cgtatctcac tca                   43

<210> SEQ ID NO 42
<211> LENGTH: 44
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (44)..(44)
<223> OTHER INFORMATION: modified by /sp18//sp18//3'aminoC6//
      desthiobiotin/

<400> SEQUENCE: 42
tggatcgtga tgactgtccc gacaagaatt cgtatctcac tcag                  44

<210> SEQ ID NO 43
<211> LENGTH: 43
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (43)..(43)
<223> OTHER INFORMATION: modified by /sp18//3'thiolC3/

```
<400> SEQUENCE: 43
tggatcgtga tgactgtccc gacaagctag cgtatctcac tca                              43

<210> SEQ ID NO 44
<211> LENGTH: 43
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (43)..(43)
<223> OTHER INFORMATION: modified by /sp18//3'thiolC3//SMPEG2//Bad/

<400> SEQUENCE: 44
tggatcgtga tgactgtccc gacaagctag cgtatctcac tca                              43

<210> SEQ ID NO 45
<211> LENGTH: 32
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: modified by /5'amino5//sp18/

<400> SEQUENCE: 45
cggcgatcgt gaaggaggag tacttgagtg ag                                          32

<210> SEQ ID NO 46
<211> LENGTH: 43
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (43)..(43)
<223> OTHER INFORMATION: modified by /sp18//sp18//3'aminoC6//propargyl/

<400> SEQUENCE: 46
tggatcgtga tgactgtccc gacaaaccgg tgtatctcac tca                              43

<210> SEQ ID NO 47
<211> LENGTH: 43
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (43)..(43)
<223> OTHER INFORMATION: modified by /sp18//sp18//3'aminoC6//propargyl//
     rapamycin/

<400> SEQUENCE: 47
tggatcgtga tgactgtccc gacaaaccgg tgtatctcac tca                              43

<210> SEQ ID NO 48
<211> LENGTH: 43
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
```

```
<222> LOCATION: (43)..(43)
<223> OTHER INFORMATION: modified by /sp18//sp18//3'thiolC3/

<400> SEQUENCE: 48
tggatcgtga tgactgtccc gacaactgca ggtatctcac tca            43

<210> SEQ ID NO 49
<211> LENGTH: 43
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (43)..(43)
<223> OTHER INFORMATION: modified by /sp18//sp18//3'thiolC3//SM(PEG)2//
      BakL78A/

<400> SEQUENCE: 49
tggatcgtga tgactgtccc gacaactgca ggtatctcac tca            43

<210> SEQ ID NO 50
<211> LENGTH: 43
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (43)..(43)
<223> OTHER INFORMATION: modified by /sp18//3'thiolC3//SM(PEG)2//Bak/

<400> SEQUENCE: 50
tggatcgtga tgactgtccc gacaagctag cgtatctcac tca            43

<210> SEQ ID NO 51
<211> LENGTH: 32
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: modified by /5'carboxy//sp18/

<400> SEQUENCE: 51
cggcgatcgt gaaggagggc atgctgagtg ag                         32

<210> SEQ ID NO 52
<211> LENGTH: 32
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: modified by /5'carboxy//sp18/

<400> SEQUENCE: 52
cggcgatcgt gaaggaggct cgagtgagtg ag                         32

<210> SEQ ID NO 53
<211> LENGTH: 32
<212> TYPE: DNA
<213> ORGANISM: Artificial Sequence
<220> FEATURE:
<223> OTHER INFORMATION: Synthetic Polynucleotide
```

```
<220> FEATURE:
<221> NAME/KEY: misc_feature
<222> LOCATION: (1)..(1)
<223> OTHER INFORMATION: modified by /5'amino5//sp18//sp18/

<400> SEQUENCE: 53
cggcgatcgt gaaggaggag tacttgagtg ag                                32

<210> SEQ ID NO 54
<211> LENGTH: 32
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: modified by /benzylguanine//5'amino5//sp18//
      sp18/

<400> SEQUENCE: 54
cggcgatcgt gaaggaggag tacttgagtg ag                                32

<210> SEQ ID NO 55
<211> LENGTH: 32
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: modified by /5'carboxy//sp18/

<400> SEQUENCE: 55
cggcgatcgt gaaggagggt cgactgagtg ag                                32

<210> SEQ ID NO 56
<211> LENGTH: 32
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: modified by /benzylguanine//5'amino5//sp18//
      sp18/

<400> SEQUENCE: 56
cggcgatcgt gaaggaggac cggttgagtg ag                                32

<210> SEQ ID NO 57
<211> LENGTH: 32
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: modified by /benzylguanine//5'amino5//sp18//
      sp18/

<400> SEQUENCE: 57
cggcgatcgt gaaggaggct agcctgagtg ag                                32

<210> SEQ ID NO 58
<211> LENGTH: 32
```

```
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: modified by /benzylguanine//5'amino5//sp18/
<220> FEATURE:
<221> NAME/KEY: misc_feature
<222> LOCATION: (20)..(23)
<223> OTHER INFORMATION: n is a, c, g, or t

<400> SEQUENCE: 58
cggcgatcgt gaaggaggan nnnttgagtg ag                                   32

<210> SEQ ID NO 59
<211> LENGTH: 32
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: modified by /benzylguanine//5'amino5//sp18/

<400> SEQUENCE: 59
cggcgatcgt gaaggaggca tgcctgagtg ag                                   32

<210> SEQ ID NO 60
<211> LENGTH: 43
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (43)..(43)
<223> OTHER INFORMATION: modified by /sp18//sp18//3'aminoC6//CBS/

<400> SEQUENCE: 60
tggatcgtga tgactgtccc gacaagaatt cgtatctcac tca                       43

<210> SEQ ID NO 61
<211> LENGTH: 43
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (43)..(43)
<223> OTHER INFORMATION: modified by /sp18//3'C6dithiol//SM(PEG)2//Bad/

<400> SEQUENCE: 61
tggatcgtga tgactgtccc gacaagcatg cgtatctcac tca                       43

<210> SEQ ID NO 62
<211> LENGTH: 43
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (43)..(43)
<223> OTHER INFORMATION: modified by /sp18//sp18//3'aminoC6//CBS/

<400> SEQUENCE: 62
```
tggatcgtga tgactgtccc gacaaccatg ggtatctcac tca        43

<210> SEQ ID NO 63
<211> LENGTH: 34
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (34)..(34)
<223> OTHER INFORMATION: modified by /spacer//spacer//3'aminoC6//
      glutarate/

<400> SEQUENCE: 63
ggctaatccg tacgataggc atgcatgagt ggga        34

<210> SEQ ID NO 64
<211> LENGTH: 54
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: modified by /5'amino5/

<400> SEQUENCE: 64
ccctgtacac agctcaaagt tgctgaaatg atcgtatgct aaaccatccc actc        54

<210> SEQ ID NO 65
<211> LENGTH: 54
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: modified by /GLCBS//5'amino5/

<400> SEQUENCE: 65
ccctgtacac ttcctcaagt tgctgaaatg atcgtatgct aaaccatccc actc        54

<210> SEQ ID NO 66
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 66
tggatcgtga tgactgtcc        19

<210> SEQ ID NO 67
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 67
cggcgatcgt gaaggag        17

<210> SEQ ID NO 68
<211> LENGTH: 81
<212> TYPE: DNA

<213> ORGANISM: Artificial Sequence
<220> FEATURE:
<223> OTHER INFORMATION: Synthetic Polynucleotide

<400> SEQUENCE: 68
aatgatacgg cgaccaccga gatctacact ctttccctac acgacgctct tccgatctta    60
gcagcggcga tcgtgaagga g                                               81

<210> SEQ ID NO 69
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 69
aatgatacgg cgaccaccga gatctacact ctttccctac acgacgctct tccgatctga    60
tggacggcga tcgtgaagga g                                               81

<210> SEQ ID NO 70
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 70
aatgatacgg cgaccaccga gatctacact ctttccctac acgacgctct tccgatcttt    60
ctcgcggcga tcgtgaagga g                                               81

<210> SEQ ID NO 71
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 71
aatgatacgg cgaccaccga gatctacact ctttccctac acgacgctct tccgatcttc    60
tacccggcga tcgtgaagga g                                               81

<210> SEQ ID NO 72
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 72
aatgatacgg cgaccaccga gatctacact ctttccctac acgacgctct tccgatctgt    60
acctcggcga tcgtgaagga g                                               81

<210> SEQ ID NO 73
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 73
caagcagaag acggcatacg agctcttccg atctttaggg tggatcgtga tgactgtccc    60

<210> SEQ ID NO 74
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 74
caagcagaag acggcatacg agctcttccg atcttgagac tggatcgtga tgactgtccc    60

<210> SEQ ID NO 75
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 75
caagcagaag acggcatacg agctcttccg atctcactca tggatcgtga tgactgtccc    60

<210> SEQ ID NO 76
<211> LENGTH: 8
<212> TYPE: PRT
<213> ORGANISM: Artificial Sequence
<220> FEATURE:
<223> OTHER INFORMATION: Synthetic Polynucleotide

<400> SEQUENCE: 76

Thr Gln Asp Pro Ser Arg Val Gly
1               5

<210> SEQ ID NO 77

<400> SEQUENCE: 77

000

<210> SEQ ID NO 78

<400> SEQUENCE: 78

000

<210> SEQ ID NO 79
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 79
aatgatacgg cgaccaccga gatctacact ctttccctac acgacgctct tccgatctat    60
ggctcggcga tcgtgaagga g                                              81

<210> SEQ ID NO 80
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 80
aatgatacgg cgaccaccga gatctacact ctttccctac acgacgctct tccgatcttg    60
cgatcggcga tcgtgaagga g                                              81

```
<210> SEQ ID NO 81
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 81
aatgatacgg cgaccaccga gatctacact ctttccctac acgacgctct tccgatctcg    60
atcacggcga tcgtgaagga g                                              81

<210> SEQ ID NO 82
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 82
aatgatacgg cgaccaccga gatctacact ctttccctac acgacgctct tccgatctgc    60
aatgcggcga tcgtgaagga g                                              81

<210> SEQ ID NO 83
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 83
aatgatacgg cgaccaccga gatctacact ctttccctac acgacgctct tccgatctct    60
cacccggcga tcgtgaagga g                                              81

<210> SEQ ID NO 84
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 84
aatgatacgg cgaccaccga gatctacact ctttccctac acgacgctct tccgatcttg    60
tctgcggcga tcgtgaagga g                                              81

<210> SEQ ID NO 85
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 85
aatgatacgg cgaccaccga gatctacact ctttccctac acgacgctct tccgatctga    60
catccggcga tcgtgaagga g                                              81

<210> SEQ ID NO 86
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 86
```

-continued aatgatacgg cgaccaccga gatctacact ctttccctac acgacgctct tccgatctag    60
tcctcggcga tcgtgaagga g    81

<210> SEQ ID NO 87
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 87
aatgatacgg cgaccaccga gatctacact ctttccctac acgacgctct tccgatctag    60
acgacggcga tcgtgaagga g    81

<210> SEQ ID NO 88
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 88
caagcagaag acggcatacg agctcttccg atcttggatc gtgatgactg tccc    54

<210> SEQ ID NO 89
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 89
tggagttcag acgtgtgctc ttccgatctt ggatcgtgat gactgtccc    49

<210> SEQ ID NO 90
<211> LENGTH: 56
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (34)..(37)
<223> OTHER INFORMATION: n is a, c, g, or t

<400> SEQUENCE: 90
acactctttc cctacacgac gctcttccga tctnnnnatc ggcgatcgtg aaggag    56

<210> SEQ ID NO 91
<211> LENGTH: 57
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (34)..(37)
<223> OTHER INFORMATION: n is a, c, g, or t

<400> SEQUENCE: 91
acactctttc cctacacgac gctcttccga tctnnnngat cggcgatcgt gaaggag    57

<210> SEQ ID NO 92
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 92
aatgatacgg cgaccaccga gatctacaca ttactcgaca ctctttccct acacgac    57

<210> SEQ ID NO 93
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 93
aatgatacgg cgaccaccga gatctacact ccggagaaca ctctttccct acacgac    57

<210> SEQ ID NO 94
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 94
aatgatacgg cgaccaccga gatctacacc gctcattaca ctctttccct acacgac    57

<210> SEQ ID NO 95
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 95
caagcagaag acggcatacg agatgtgcgg acgtgactgg agttcagacg tgtgct    56

<210> SEQ ID NO 96
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 96
caagcagaag acggcatacg agattacgta cggtgactgg agttcagacg tgtgct    56

<210> SEQ ID NO 97
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 97
caagcagaag acggcatacg agatatatca gtgtgactgg agttcagacg tgtgct    56

<210> SEQ ID NO 98
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 98
atgcaccatc accaccauca cgcccatcac tgggggtac    39

<210> SEQ ID NO 99
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 99
atggtggtga tggugcatgg tatatctcct tcttaaagtt aaac           44

<210> SEQ ID NO 100
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 100
accatcttaa tgatgatgat gaugatgttt gaaggaagct ttgatttgcc tgttc     55

<210> SEQ ID NO 101
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 101
accaatcatc atcatcatta agatgguccc atagtctgta tccaa            45

<210> SEQ ID NO 102
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 102
ccctcctctt ctggaaagcg tgacctggat tgtgc                35

<210> SEQ ID NO 103
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 103
gcacaatcca ggtcacgctt tccagaagag gagg                 34

<210> SEQ ID NO 104
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 104
cctgagcact ggcataagtg tttccccatt gccaagggag ag           42

<210> SEQ ID NO 105
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 105
ctctcccttg gcaatgggga aacacttatg ccagtgctca gg                    42

<210> SEQ ID NO 106
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 106
ccctgaagcc cctgtctgtt tcctattgtc aagcaacttc cctgagg               47

<210> SEQ ID NO 107
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 107
cctcagggaa gttgcttgac aataggaaac agacaggggc ttcaggg               47

<210> SEQ ID NO 108
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 108
gtgacctgga ttgtgctctg tgaacccatc agcgtcagc                        39

<210> SEQ ID NO 109
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 109
gctgacgctg atgggttcac agagcacaat ccaggtcac                        39

<210> SEQ ID NO 110
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 110
ggcgcccagc tcagccactg tgtaacaggc aaatcaa                          37

<210> SEQ ID NO 111
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 111
ttgatttgcc tgttacacag tggctgagct gggcgcc                          37

<210> SEQ ID NO 112

```
<210> SEQ ID NO 112
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 112
actcatcatc accatcauca ccagagcaac cgggagctgg tgg                43

<210> SEQ ID NO 113
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 113
atgatggtga tgatgagucc gggggatcc acgc                           34

<210> SEQ ID NO 114
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 114
accaccacca ccacugagat ctccggggga attcatcgtg                    40

<210> SEQ ID NO 115
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 115
agtggtgatg atgguggtgg tggttgaagc gttcctg                       37

<210> SEQ ID NO 116
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 116
atgcatcatc accatcauca ccagagcaac cggg                          34

<210> SEQ ID NO 117
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 117
agactatggg accatctcag cggttgaagc gttcctggc                     39

<210> SEQ ID NO 118
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 118
```

-continued agatggtccc atagtcugta tccaaataat gaatcttcgg gtg    43

<210> SEQ ID NO 119
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 119
atgatggtga tgatgcaugg tcgcgctggc ggtc    34

<210> SEQ ID NO 120
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 120
ccatgggagt gcaggtggaa acc    23

<210> SEQ ID NO 121
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 121
tggcctgtgc tggatatctg cag    23

<210> SEQ ID NO 122
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 122
atccagagga gugcaggtgg aaaccatct    29

<210> SEQ ID NO 123
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 123
attctagtct acagauccte ttctgagatg agtttttgtt c    41

<210> SEQ ID NO 124
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 124
actcctctgg auccacgcgg aaccagatc    29

<210> SEQ ID NO 125
<211> LENGTH: 40
<212> TYPE: DNA

<213> ORGANISM: Artificial Sequence
<220> FEATURE:
<223> OTHER INFORMATION: Synthetic Polynucleotide

<400> SEQUENCE: 125
atctgtagac tagaautcat cgtgactgac tgacgatctg   40

<210> SEQ ID NO 126
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 126
agtctatgga gcugatccga gtggccatc   29

<210> SEQ ID NO 127
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 127
agtctactgc ttugagattc gtcggaacac atg   33

<210> SEQ ID NO 128
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 128
agctccatag acucgagcgg ccgc   24

<210> SEQ ID NO 129
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 129
caaagcagta gacuagaggg cccgtttaaa cccg   34

<210> SEQ ID NO 130
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 130
caccatggcg gcagcgagct gatccgagtg gc   32

<210> SEQ ID NO 131
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 131
atgatggtga tgcatagact cgagcggccg c   31

<210> SEQ ID NO 132
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 132
caccatggcg gctctgagct gatccgagtg gccatcc                          37

<210> SEQ ID NO 133
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 133
gtgatgatgc atggtggccg ccactgtgct gg                               32

<210> SEQ ID NO 134
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 134
agcttccttc aaataagcgu ttaaactcga ggttaattaa tgagcgg               47

<210> SEQ ID NO 135
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 135
attgatccgc cugcaggacc                                             20

<210> SEQ ID NO 136
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 136
cttatttgaa ggaagcuttg atttgcctgt tcttcag                          37

<210> SEQ ID NO 137
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 137
aggcggatca auggcccatc actggggg                                    28

<210> SEQ ID NO 138
<211> LENGTH: 29
<212> TYPE: DNA
<213> ORGANISM: Artificial Sequence
<220> FEATURE:

<223> OTHER INFORMATION: Synthetic Polynucleotide

<400> SEQUENCE: 138
aattcaccgg uctgtacaga tttaaatgc                             29

<210> SEQ ID NO 139
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 139
agcttccttc aaaggaggau caatggacaa agactgcgaa atgaagc          47

<210> SEQ ID NO 140
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 140
atcctccttt gaaggaagcu ttgatttgcc tgttctt                    37

<210> SEQ ID NO 141
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 141
accggtgaat ucaccgccac catggcccat cactggggg                  39

<210> SEQ ID NO 142
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 142
gtacagaccg gtgaattcac c                                     21

<210> SEQ ID NO 143
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 143
atttaaatgc tggcgcgc                                         18

<210> SEQ ID NO 144
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 144
taaactcgag gttaattaat gagcgg                                26

```
<210> SEQ ID NO 145
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 145
gatccgcctg caggac                                                     16

<210> SEQ ID NO 146
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 146
tataaccggt gcggttgaag cgttcctg                                        28

<210> SEQ ID NO 147
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 147
ttaaggcgcg ccggccacca tgcagagcaa ccgggagc                             38

<210> SEQ ID NO 148
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 148
ttaacctgca ggacagagca accgggagc                                       29

<210> SEQ ID NO 149
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 149
tatactcgag gcggttgaag cgttcctg                                        28

<210> SEQ ID NO 150
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 150
tataggcgcg ccgccgccac catggag                                         27

<210> SEQ ID NO 151
<211> LENGTH: 23
<212> TYPE: DNA
<213> ORGANISM: Artificial Sequence
<220> FEATURE:
<223> OTHER INFORMATION: Synthetic Polynucleotide
```

```
<400> SEQUENCE: 151
ttaaaccggt gctgccgccc tgc                                          23

<210> SEQ ID NO 152
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 152
tatacctgca ggagccgcca ccatggag                                     28

<210> SEQ ID NO 153
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 153
ttaactcgag gctgccgccc tgc                                          23

<210> SEQ ID NO 154
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 154
ttaaaccggt ttccagtttt agaagctcca catc                              34

<210> SEQ ID NO 155
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 155
tataggcgcg ccgccaccat gggagtgc                                     28

<210> SEQ ID NO 156
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 156
tatacctgca ggagccacca tgggagtgc                                    29

<210> SEQ ID NO 157
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 157
ttaactcgag ttccagtttt agaagctcca catc                              34
```